US011939600B2

(12) United States Patent
Tachikawa et al.

(10) Patent No.: US 11,939,600 B2
(45) Date of Patent: Mar. 26, 2024

(54) COMPOSITIONS AND METHODS FOR TREATING PHENYLKETONURIA

(71) Applicant: Arcturus Therapeutics, Inc., San Diego, CA (US)

(72) Inventors: Kiyoshi Tachikawa, San Diego, CA (US); Carlos Gustavo Perez-Garcia, San Diego, CA (US); Padmanabh Chivukula, San Diego, CA (US); Hari Bhaskaran, San Diego, CA (US); Sean Christopher Daugherty, Petaluma, CA (US); Christian W. Cobaugh, Newton, MA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 968 days.

(21) Appl. No.: 16/617,462

(22) PCT Filed: May 31, 2018

(86) PCT No.: PCT/US2018/035476

§ 371 (c)(1),
(2) Date: Nov. 26, 2019

(87) PCT Pub. No.: WO2018/222925

PCT Pub. Date: Dec. 6, 2018

(65) Prior Publication Data

US 2020/0109375 A1 Apr. 9, 2020

Related U.S. Application Data

(60) Provisional application No. 62/513,363, filed on May 31, 2017.

(51) Int. Cl.
*C12N 9/02* (2006.01)
*A61K 31/7115* (2006.01)
*A61K 48/00* (2006.01)

(52) U.S. Cl.
CPC ........ *C12N 9/0071* (2013.01); *A61K 31/7115* (2013.01); *A61K 48/005* (2013.01); *C12Y 114/16001* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 8,093,367 B2 | 1/2012 | Kore et al. | |
| 8,158,601 B2 | 4/2012 | Chen et al. | |
| 8,304,529 B2 | 11/2012 | Kore et al. | |
| 9,149,506 B2 | 10/2015 | Chakraborty et al. | |
| 10,383,952 B2 | 8/2019 | Payne et al. | |
| 2011/0256175 A1 | 10/2011 | Hope et al. | |
| 2012/0027803 A1 | 2/2012 | Manoharan et al. | |
| 2012/0128760 A1 | 5/2012 | Manoharan et al. | |
| 2015/0110858 A1* | 4/2015 | DeRosa | A61K 9/1272 514/44 R |

FOREIGN PATENT DOCUMENTS

| | | |
|---|---|---|
| WO | 2009086558 A1 | 7/2009 |
| WO | 2009127060 A1 | 10/2009 |
| WO | 2010048536 A2 | 4/2010 |
| WO | 2010054406 A1 | 5/2010 |
| WO | 2010088537 A2 | 8/2010 |
| WO | 2010129709 A1 | 11/2010 |
| WO | 2011153493 A2 | 12/2011 |
| WO | WO-2013151666 A2 | 10/2013 |
| WO | 2015051169 A2 | 4/2015 |
| WO | 2015061491 A1 | 4/2015 |
| WO | 2015074085 A1 | 5/2015 |
| WO | 2016004318 A1 | 1/2016 |
| WO | 2016070166 A2 | 5/2016 |
| WO | WO-2017066797 A1 | 4/2017 |
| WO | 2018222925 A1 | 12/2018 |

OTHER PUBLICATIONS

Chica et al. Curr Opin Biotechnol. Aug. 2005; 16(4):378-84 (Year: 2005).*
Singh et al. Curr Protein Pept Sci. 2017, 18, 1-11 (Year: 2017).*
Accession BBY74290. Jun. 18, 2015. (Year: 2015).*
Li et al. (2016) "Effects of Chemically Modified Messenger RNA on Protein Expression", Bioconjugate Chemistry, 27(3):849-853.
The United States Patent and Trademark Office, International Search Report and Written Opinion for PCT/US2018/035476, Oct. 19, 2018, 14 pages.
Extended European Search Report for Application No. EP 18810366.7, dated Jan. 25, 2021, 7 pages.
Berge et al. (Jan. 1977) "Pharmaceutical Salts", Journal of Pharmaceutical Sciences, 66(1):1-19.
Gould, Philip L. (Nov. 1986) "Salt Selection for Basic Drugs", International Journal of Pharmaceutics, 33 (1-3):201-217.
Gustafsson et al. (Jul. 2004) "Codon Bias and Heterologous Protein Expression", Trends in Biotechnology, 22 (7):346-353.
Jemielity et al. (2003) "Novel "Anti-Reverse" Cap Analogs with Superior Translational Properties", RNA, 9(9):1108-1122.
Kozak, Marilyn (Nov. 1990) "Downstream Secondary Structure Facilitates Recognition of Initiator Codons by Eukaryotic Ribosomes", Proceedings of the National Academy of Sciences, 87(21):8301-8305.

(Continued)

*Primary Examiner* — Christian L Fronda
(74) *Attorney, Agent, or Firm* — MINTZ, LEVIN, COHN, FERRIS, GLOVSKY AND POPEO, P.C.

(57) ABSTRACT

This invention provides a range of translatable polynucleotide and oligomer molecules for expressing a human phenylalanine hydroxylase (PAH), or a fragment thereof having PAH activity. The polynucleotide and oligomer molecules are expressible to provide the human PAH or a fragment thereof having PAH activity. The molecules can be used as active agents to express an active polypeptide or protein in cells or subjects. The agents can be used in methods for ameliorating, preventing, delaying onset, or treating a disease or condition associated with phenylketonuria, decreased metabolism of phenylalanine, or increased levels of phenylalanine in a subject.

14 Claims, 7 Drawing Sheets

Specification includes a Sequence Listing.

(56) References Cited

OTHER PUBLICATIONS

Kozak, Marilyn (Jul. 1988) "Leader Length and Secondary Structure Modulate mRNA Function Under Conditions of Stress.", Molecular and Cellular Biology, 8(7):2737-2744.
Kozak, Marilyn (Oct. 25, 1991) "Structural Features In Eukaryotic mRNAs that Modulate the Initiation of Translation", Journal of Biological Chemistry, 266(30):19867-19870.
Kozak, Marilyn (Feb. 1989) "The Scanning Model for Translation: An Update", Journal of Cell Biology, 108(2):229-241.
Love et al. (Feb. 2, 2010) "Lipid-like Materials for Low-dose, In Vivo Gene Silencing", Proceedings of the National Academy of Sciences, 107(5):1864-1869.
Ozpolat et al. (Feb. 2014 and as Dec. 30, 2013 in epub) "Liposomal SIRNA Nanocarriers for Cancer Therapy", Advanced Drug Delivery Reviews, 66:110-116(16 pages).
Rodriguez-Gascon et al. (Apr. 10, 2014) "Development of Nucleic Acid Vaccines: Use of Self-Amplifying RNA In Lipid Nanoparticles", International Journal of Nanomedicine, 9:1833-1843.
Sercombe et al. (Dec. 1, 2015) "Advances and Challenges of Liposome Assisted Drug Delivery", Frontiers in Pharmacology, 6(286): 13 Pages.
Mllalobos et al. (Jun. 6, 2006) "Gene Designer: A Synthetic Biology Tool for Constructing Artificial DNA Segments", BMC Bioinformatics, 7:285(8 pages).

* cited by examiner

FIG. 1 PAH expression level in WT mice

FIG. 2 Liver PAH expression in vivo timecourse

FIG. 3 PAH expression in human primary hepatocytes

FIG. 4 PAH expression in treatment groups

FIG. 5 PAH Expression in Mouse and Human Liver Cells

COMPOSITIONS AND METHODS FOR TREATING PHENYLKETONURIA

CROSS-REFERENCE TO RELATED APPLICATIONS

This application claims priority to U.S. Provisional Application Ser. No. 62/513,363, filed May 31, 2017, which is herein incorporated by reference in its entirety for all purposes.

TECHNICAL FIELD OF THE INVENTION

This invention relates to the fields of molecular biology and genetics, as well as to biopharmaceuticals and therapeutics generated from translatable molecules. More particularly, this invention relates to methods, structures and compositions for molecules having the ability to be translated into active polypeptides or proteins, for use in vivo and as therapeutics.

DESCRIPTION OF TEXT FILE SUBMITTED ELECTRONICALLY

The contents of the text file submitted electronically herewith are incorporated herein by reference in their entirety: A computer readable format copy of the Sequence Listing (filename: ULPI_040_01WO_SeqList_ST25.txt, date recorded: May 29, 2018, file size: 89 kilobytes).

BACKGROUND OF THE INVENTION

Phenylketonuria (PKU) is an inherited disorder of phenylalanine (Phe) metabolism characterized by the appearance of phenylpyruvic acid in the urine. PKU is a metabolic disease characterized by an inability of the subject to process the essential amino acid phenylalanine (Phe) to tyrosine (Tyr) due to a deficiency of the enzyme phenylalanine hydroxylase (PAH). Without PAH, phenylalanine accumulates in the blood and body tissues. The excess phenylalanine is toxic to the central nervous system, and when left untreated, can result in mental retardation and other neurological deficits and symptoms.

Phenylketonuria (PKU) is caused by autosomal recessive defects in the phenylalanine hydroxylase (PAH) gene resulting in absence or low function of phenylalanine hydroxylase (PAH). Loss in PAH activity disables normal phenylalanine catabolism/tyrosine metabolism, causing toxic levels of phenylalanine to accumulate and damage the developing brain.

Early diagnosis can be important in treating phenylketonuria (PKU). A severe form of the disease, "classical" PKU, can be diagnosed within the first six months of life, using a heel prick-Guthrie test or ESI-MS/MS, and can result in developmental delay, seizure, and failure to thrive. When a strict diet is followed within the first few weeks of life, affected children can expect improved development and a normal life span. Newborn screening for PKU is carried out in most developed countries. However, despite the use of a low protein, low Phe diet, PKU may cause cognitive and neurodevelopment deficiencies.

Current treatments for PKU may only be effective in a small number of subjects. Specifically, the therapeutic saproterin provides a synthetic form of cofactor for PAH, but is only effective for PKU patients with a cofactor synthesis defect or in patients carrying a form of mutated PAH that can be overcome by overloading the system with cofactor. A more recent therapeutic known as pegvaliase has been developed which provides a cyanobacterium-derived enzyme called phenylalanine ammonia lyase (PAL). However, this approach does not correct the underlying genetic disorder (PAH deficiency) and will not reconstitute the natural pathway that is needed to address the neurocognitive defects associated with PKU.

Accordingly, there is an urgent need for molecules, structures and compositions having the ability to be translated to provide active PKU therapeutics. Such new molecules having functional cytoplasmic half-life for producing active PAH capable of converting phenylalanine to tyrosine can yield new therapeutic modalities.

What is needed are translatable molecules that have increased translational efficiency and/or half-life over native mRNA, to be used in methods and compositions for producing and delivering active PAH as medicine.

SUMMARY OF THE INVENTION

This invention provides methods and compositions for novel molecules having the ability to be translated, which can be used to provide one or more active polypeptides and proteins, or fragments thereof. More specifically, embodiments of this invention provide methods and compositions for translatable molecules to provide phenylalanine hydroxylase (PAH).

The translatable molecules of this invention can have functional cytoplasmic activity for producing PAH polypeptides or proteins. The peptides and proteins may be active for therapeutic modalities.

The translatable molecules of this invention can have long half-life, particularly in the cytoplasm of a cell. The translatable molecules can be expressible to provide a product that is active for ameliorating, preventing or treating a disease or condition associated with PAH. The disease or condition can be associated with undesirable modulation of protein concentration, or undesirable activity of a protein.

This disclosure provides a range of structures for translatable molecules for producing PAH polypeptides or proteins. In some embodiments, the translatable molecules can have an increased ability to be translated and/or an extended half-life over a native mRNA.

The translatable molecules of this invention can be used in medicines, and for methods and compositions for producing and delivering active polypeptides and proteins. The translatable molecules of this invention can be used to provide polypeptides or proteins in vitro, ex vivo, or in vivo.

Embodiments of this disclosure provide a range of novel polynucleotides for expressing a human phenylalanine hydroxylase (PAH), or a fragment thereof having PAH activity. The polynucleotides can include natural nucleotides and chemically modified nucleotides. The polynucleotides can be expressible to provide a human PAH or a fragment thereof having PAH activity.

In further aspects, this invention provides a range of novel translatable oligomers comprising one or more unlocked nucleic acid (UNA) monomers for expressing a human phenylalanine hydroxylase (PAH), or a fragment thereof having PAH activity. A translatable oligomer can contain one or more UNA monomers, along with natural nucleotides and chemically modified nucleotides. A translatable oligomer comprising one or more UNA monomers can be expressible to provide the human phenylalanine hydroxylase (PAH), or a fragment thereof having PAH activity.

In certain aspects, the translatable molecules of this invention can provide high-efficiency expression of a polypeptide or protein, or a fragment thereof. The expression can be in vitro, ex vivo, or in vivo.

In some embodiments, a molecule of this invention can have increased cytoplasmic half-life over a native, mature mRNA that encodes the same polypeptide or protein. The inventive molecules and compositions can provide increased functional cellular activity with respect to a native, mature mRNA.

In further aspects, a translatable molecule of this invention can provide increased activity as a drug agent providing a peptide or protein product, as compared to a native, mature mRNA. A translatable molecule of this invention may reduce the dose level required for efficacious therapy.

Embodiments of this invention include the following.

BRIEF DESCRIPTION OF THE DRAWINGS

FIG. 1 shows the relative expression of PAH in wild-type (hereinafter used interchangeably with "WT") C57BL/c mice for translatable molecules 513, 514, 517 and 520 at 8 hrs. The sequences 513, 514, 517 and 520 with tobacco etch virus (TEV) 5' UTR and *Xenopus* beta-globin (XBG) 3' UTR were synthesized and purified. The four molecules 513, 514, 517 and 520 were capped during transcription and synthesized with $N^1$-methylpseudouridine, so that 100% of uridines were replaced with $N^1$-methylpseudouridine. The synthesized translatable molecules 513, 514, 517 and 520 encoding PAH were each prepared in a liposomal formulation and intravenously injected into WT mice at 3 and 10 mg/kg. Mice livers were harvested, and the PAH expression was quantified using NIR Western Blot. The translatable molecules 513, 514, 517 and 520 had surprisingly increased translation efficiency as compared to reference human WT mRNA.

FIG. 2 shows the relative liver expression of PAH in WT mice post-dose of pooled translatable molecules 513, 514, 517 and 520, as compared to a human WT reference mRNA. The synthesized translatable molecules 513, 514, 517 and 520 encoding PAH were each prepared in a liposomal formulation and intravenously injected into WT mice.

FIG. 3 shows expression results for molecules 513, 514, 517, and 520 after transfection with 0.6 μg of the mRNA in human primary hepatocytes. Cell lysates were harvested at 24 h and 48 h. Quantitative Western Blot was performed to detect PAH by using an antibody specific for PAH. The data were compared to mock negative controls which had values of zero.

FIG. 4 shows expression results for pooled molecules 513, 514, 517, and 520 co-formulated and injected via IP in WT mice. The dose injected was 10 mpk, and livers were collected at different timepoints (8 h, 24 h, and 48 h) for analysis. Quantitative Western Blot was performed to detect PAH by using an antibody specific for PAH. The co-formulated variants yielded high expression versus PBS control.

DETAILED DESCRIPTION OF THE INVENTION

Figure 1:
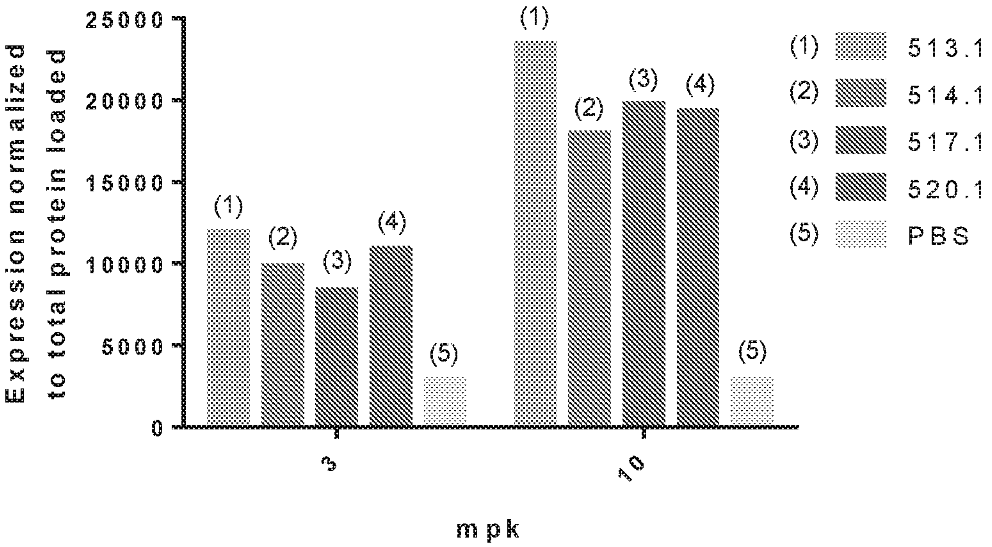
FIG. 1 shows the results of expressing human phenylalanine hydroxylase (PAH) in vivo using a translatable molecule of this invention.

This invention provides a range of novel agents and compositions to be used for therapeutic applications. The molecules and compositions of this invention can be used for ameliorating, preventing or treating disease associated with phenylketonuria (PKU) or reduced presence or function of phenylalanine hydroxylase (PAH) in a subject.

In some embodiments, this invention encompasses synthetic, purified, translatable polynucleotide molecules for expressing a human phenylalanine hydroxylase. The molecules may contain natural and chemically modified nucleotides, and encode the human phenylalanine hydroxylase (PAH), or a fragment thereof having PAH activity.

In certain embodiments, this disclosure includes synthetic, purified, translatable oligomer molecules comprising one or more UNA monomers for expressing a human phenylalanine hydroxylase (PAH), or a fragment thereof having PAH activity. A translatable oligomer may contain one or more UNA monomers, as well as natural and chemically-modified nucleotides. A translatable oligomer comprising one or more UNA monomers can be expressible to provide the human phenylalanine hydroxylase (PAH), or a fragment thereof having PAH activity.

As used herein, the term "translatable" may be used interchangeably with the term "expressible" and refers to the ability of polynucleotide, or a portion thereof, to be converted to a polypeptide by a host cell. As is understood in the art, translation is the process in which ribosomes in a cell's cytoplasm create polypeptides. In translation, messenger RNA (mRNA) is decoded by tRNAs in a ribosome complex to produce a specific amino acid chain, or polypeptide. Furthermore, the term "translatable" when used in this specification in reference to an oligomer, means that at least a portion of the oligomer, e.g., the coding region of an oligomer sequence (also known as the coding sequence or CDS), is capable of being converted to a protein or a fragment thereof.

As used herein, the term "monomer" refers to a single unit, e.g., a single nucleic acid, which may be joined with another molecule of the same or different type to form an oligomer. In some embodiments, a monomer may be an unlocked nucleic acid, i.e., a UNA monomer.

Meanwhile, the term "oligomer" may be used interchangeably with "polynucleotide" and refers to a molecule comprising at least two monomers and includes oligonucleotides such as DNAs and RNAs. In the case of oligomers containing RNA monomers and/or unlocked nucleic acid (UNA) monomers, the oligomers of the present invention may contain sequences in addition to the coding sequence (CDS). These additional sequences may be untranslated sequences, i.e., sequences which are not converted to protein by a host cell. These untranslated sequences can include a 5' cap, a 5' untranslated region (5' UTR), a 3' untranslated region (3' UTR), and a tail region, e.g., a polyA tail region. As described in further detail herein, any of these untranslated sequences may contain one or more UNA monomers—these UNA monomers are not capable of being translated by a host cell's machinery. In the context of the present invention, a "translatable oligomer", a "translatable molecule", "translatable polynucleotide", or "translatable compound" refers to a sequence that comprises a region, e.g., the coding region of an RNA (e.g., the coding sequence of human PAH or a codon-optimized version thereof), that is capable of being converted to a protein or a fragment thereof, e.g., the human PAH protein or a fragment thereof.

As used herein, the term "codon-optimized" means a natural (or purposefully designed variant of a natural) coding sequence which has been redesigned by choosing different codons without altering the encoded protein amino acid sequence increasing the protein expression levels (Gustafsson et al., *Codon bias and heterologous protein expression.* 2004, Trends Biotechnol 22: 346-53). Variables such as high codon adaptation index (CAI), LowU method, mRNA secondary structures, cis-regulatory sequences, GC content and many other similar variables have been shown to somewhat correlate with protein expression levels (Villalobos et al., *Gene Designer: a synthetic biology tool for constructing artificial DNA segments.* 2006, BMC Bioinformatics 7:285). High CAI (codon adaptation index) method picks a most frequently used synonymous codon for an entire protein coding sequence. The most frequently used codon for each amino acid is deduced from 74218 protein-coding genes from a human genome. The LowU method targets only U-containing codons that can be replaced with a synonymous codon with fewer U moieties. If there are a few choices for the replacement, the more frequently used codon will be selected. The remaining codons in the sequence are not changed by the LowU method. This method may be used in conjunction with the disclosed mrRNAs to design coding sequences that are to be synthesized with 5-methoxyuridine.

The translatable molecules of this invention can be used in methods for ameliorating, preventing or treating a disease or condition associated with phenylketonuria, or the reduced concentration or function of phenylalanine hydroxylase (PAH) in a subject. The phenylketonuria can be associated with intellectual disability, delayed development, psychiatric disorders, neurological deficits, seizures, hyperactivity, loss of bone strength, or microcephaly.

A translatable molecule of this invention encoding a functional PAH moiety can be delivered to the liver, in particular to hepatocytes, of a PKU patient in need, and can reduce blood Phe levels of the patient. The translatable molecule can be used for preventing, treating, ameliorating or reversing neurological deficits of the PKU patient.

In further aspects, a translatable molecule of this invention can also be used for reducing the dependence of a PKU patient on a low Phe diet to control the disease.

In some aspects, this invention contemplates enhancement of PAH activity in a subject to modulate or normalize serum or plasma Phe levels in the subject.

In some embodiments, administering a composition comprising a translatable molecule of this invention results in a reduced Phe level in serum or plasma as compared to baseline phenylalanine level before treatment. In some embodiments, administering a composition comprising a translatable molecule of this invention results in reduction of phenylalanine levels to about 1000 μmol/L (micromole per liter) or less, about 900 μmol/L or less, about 800 μmol/L or less, about μmol/L or less, about 600 μmol/L or less, about 500 μmol/L or less, about 400 μmol/L or less, about 300 μmol/L or less, about 200 μmol/L or less, about 100 μmol/L or less or about 50 μmol/L or less in serum or plasma. In an exemplary embodiment, a therapeutically effective dose, when administered regularly results in reduction of phenylalanine levels to about 600 μmol/L or less in serum or plasma. In another exemplary embodiment, a therapeutically effective dose, when administered regularly results in reduction of phenylalanine levels to about 360 μmol/L or less in serum or plasma. In another exemplary embodiment, a therapeutically effective dose, when administered regularly results in reduction of phenylalanine levels to about 120 μmol/L or less in serum or plasma.

As used herein, the term "about" or "approximately" as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

In some embodiments, methods of this invention can modulate or maintain serum or plasma Phe levels in a subject at about 120-360 μmol/L.

In further embodiments, methods of this invention can modulate or maintain serum or plasma Phe levels in a subject at about 60-360 μmol/L.

In additional embodiments, methods of this invention can modulate or maintain serum or plasma Phe levels in a child subject at about 30-60 μmol/L.

In some embodiments, administering a composition comprising a translatable molecule of this invention results in a reduction of phenylalanine levels in a biological sample (e.g., a plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline phenylalanine levels before treatment.

Embodiments of this invention further encompass processes for making a translatable molecule for expressing a human phenylalanine hydroxylase (PAH). The processes include transcribing in vitro a PAH DNA template in the presence of natural and chemically-modified nucleoside triphosphates to form a product mixture, and purifying the product mixture to isolate the translatable molecule. A translatable molecule may also be made by methods as are known in the art.

The molecules of this invention can be translatable molecules containing RNA and/or UNA monomers. These translatable molecules can have long half-life, particularly in the cytoplasm. The long duration translatable molecules can be used for ameliorating, preventing, or treating disease associated with phenylketonuria or reduced presence or function of phenylalanine hydroxylase (PAH) in a subject.

The properties of the translatable molecules of this invention arise according to their molecular structure, and the structure of the molecule in its entirety, as a whole, can provide significant benefits based on those properties. Embodiments of this invention can provide translatable molecules having one or more properties that advantageously provide enhanced effectiveness in regulating protein expression or concentration, or modulating protein activity. The molecules and compositions of this invention can provide formulations for therapeutic agents for ameliorating, preventing, or treating disease associated with phenylketonuria or reduced presence or function of phenylalanine hydroxylase (PAH) in a subject, which can provide clinical agents.

This invention provides a range of translatable molecules that are surprisingly translatable to provide active polypeptide or protein, in vitro, ex vivo, and in vivo.

A translatable molecule of this invention is expressible to provide one or more active polypeptides or proteins, or fragments thereof.

The translatable structures and compositions can have increased translational activity or cytoplasmic half-life. In these embodiments, the translatable structures and compositions can provide increased functional half-life in the cytoplasm of mammalian cells, as compared to a native mRNA.

As used herein, the term "half-life" is the time required for a quantity such as nucleic acid or protein concentration or activity to fall to half of its value as measured at the beginning of a time period.

A range of structures for translatable molecules of this invention are provided herein, including oligomers containing one or more UNA monomers. An oligomer containing one or more UNA monomers can incorporate specialized linker groups. The linker groups can be attached in a chain in the translatable molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain, or at any position in the chain.

In further aspects, the linker groups of a chain molecule can each be attached to a nucleobase. The presence of nucleobases in the chain molecule can provide a sequence of nucleobases in the chain molecule.

In certain embodiments, this invention provides translatable oligomer molecules having chain structures that incorporate novel combinations of the linker group monomers, along with certain natural nucleotides, or non-natural nucleotides, or modified nucleotides, or chemically modified nucleotides.

The oligomer molecules of this invention can display a sequence of nucleobases, and can be designed to express a polypeptide or protein, in vitro, ex vivo, or in vivo. The expressed polypeptide or protein can have activity in various forms, including activity corresponding to a protein expressed from a natural, native or wild type mRNA, or activity corresponding to a negative or dominant negative protein.

In some aspects, this invention can provide active, translatable oligomer molecules having a base sequence that is identical to at least a fragment of a native nucleic acid molecule of a cell.

In some embodiments, the cell can be a eukaryotic cell, a mammalian cell, or a human cell.

This invention provides structures, methods and compositions for translatable oligomeric agents that incorporate the linker group monomers. The oligomeric molecules of this invention can be used as active agents in formulations for therapeutics.

This invention provides a range of translatable molecules that are useful for providing therapeutic effects because of their ability to be expressed as polypeptide or protein in a cell in a subject.

In certain embodiments, a translatable molecule can be structured as an oligomer composed of monomers. The oligomeric structures of this invention may contain one or more linker group monomers, along with certain nucleotides.

In certain embodiments, a translatable molecule may contain a sequence of nucleobases, and can be designed to express a peptide or protein of any isoform, in part by having sufficient homology with a native polynucleotide sequence.

In some embodiments, a translatable molecule can be from about 200 to about 5,000 monomers in length, or more. In certain embodiments, a translatable molecule can be from 400 to 2,600 monomers in length, from 1,200 to 2,000 monomers in length, or from 1,700 to 1,900 monomers in length. In an exemplary embodiment, the translatable molecule is from 1,750 to 1,850 monomers in length. In a further exemplary embodiment, the translatable molecule is about 1,800 monomers in length.

In some embodiments, a translatable molecule can contain from 1 to about 800 UNA monomers. In certain embodiments, a translatable molecule can contain from 1 to 600 UNA monomers, or 1 to 100 UNA monomers, or 1 to 12 UNA monomers.

In some embodiments, a translatable molecule can contain from 1 to about 800 locked nucleic acid (LNA) monomers. In certain embodiments, a translatable molecule can contain from 1 to 600 LNA monomers, or 1 to 100 LNA monomers, or 1 to 12 LNA monomers.

A translatable molecule of this invention may comprise a 5' cap, a 5' untranslated region of monomers, a coding region of monomers, a 3' untranslated region of monomers, and a tail region of monomers.

A translatable molecule of this invention may comprise a 3' untranslated region of monomers containing one or more UNA monomers.

A translatable molecule of this invention may comprise a tail region of monomers containing one or more UNA monomers.

A translatable molecule of this invention may comprise regions of sequences or structures that are operable for translation in a cell, or which have the functionality of regions of an mRNA including, for example, a 5' cap, a 5' untranslated region, a coding region, a 3' untranslated region, and a polyA tail.

This invention further contemplates methods for delivering one or more vectors comprising one or more translatable molecules to a cell. In further embodiments, the invention also contemplates delivering or one or more translatable molecules to a cell.

In some embodiments, one or more translatable molecules can be delivered to a cell, in vitro, ex vivo, or in vivo. Viral and non-viral transfer methods as are known in the art can be used to introduce translatable molecules in mammalian cells. Translatable molecules can be delivered with a pharmaceutically acceptable vehicle, or for example, with nanoparticles or liposomes.

In some embodiments, translatable structures and compositions of this invention can reduce the number and frequency of transfections required for cell-fate manipulation in culture as compared to utilizing native compositions.

In further aspects, this invention provides increased activity for translatable molecules as active agent, as compared to utilizing a native mRNA.

In some aspects, this invention can provide translatable molecules that may reduce the cellular innate immune response, as compared to that induced by a native nucleic acid, polypeptide or protein.

This invention can provide synthetic translatable molecules that are refractory to deadenylation as compared to native molecules.

In certain embodiments, this invention can provide synthetic translatable molecules with increased specific activity and longer functional half-life as compared to native molecules. The synthetic translatable molecules of this invention can provide increased levels of ectopic protein expression. When expressing a translatable molecule using a vector, cellular-delivery can be at increased levels, and cytotoxic innate immune responses can be restrained so that higher levels of ectopic protein expression can be achieved. The translatable molecules of this invention can have increased specific activity and longer functional half-life than native mRNAs.

In certain aspects, a translatable molecule may have a number of mutations relative to a native mRNA.

In further embodiments, this invention can provide translatable molecules having cleavable delivery and targeting moieties attached at a 3' end and/or a 5' end.

In general, the specific activity for a synthetic translatable molecule delivered by transfection can be viewed as the number of molecules of protein expressed per delivered transcript per unit time.

As used herein, translation efficiency refers to a measure of the production of a protein or polypeptide by translation of a translatable molecule in vitro or in vivo.

This invention provides a range of translatable oligomer molecules, which can contain one or more UNA monomers, and a number of nucleic acid monomers, wherein the translatable molecule can be expressible to provide a polypeptide or protein.

In some embodiments, this invention includes a range of translatable oligomer molecules, which can contain one or more UNA monomers in one or more untranslated regions, and a number of nucleic acid monomers, wherein the translatable molecule can be expressible to provide a polypeptide or protein.

In some embodiments, this invention includes a range of translatable molecules, which contain one or more UNA monomers in a tail region, and a number of nucleic acid monomers, wherein the translatable molecule can be expressible to provide a polypeptide or protein.

In some embodiments, a translatable molecule can contain a modified 5' cap.

In further embodiments, a translatable molecule can contain a translation enhancing 5' untranslated region of monomers.

In additional embodiments, a translatable molecule can contain a translation enhancing 3' untranslated region of monomers.

In additional embodiments, a translatable molecule can contain one or more UNA monomers in a 3' untranslated region of monomers.

In further embodiments, a translatable molecule can contain one or more UNA monomers in a tail region of monomers.

In further embodiments, a translatable molecule can contain one or more UNA monomers in a polyA tail.

In some embodiments, a translatable molecule can contain one or more LNA monomers in a 3' untranslated region of monomers or in a tail region of monomers, e.g., in a polyA tail.

In another aspect, a translatable molecule of this invention can exhibit at least 2-fold, 3-fold, 5-fold, or 10-fold increased translation efficiency in vivo as compared to a native mRNA that encodes the same translation product.

In a further aspect, a translatable molecule can produce at least a 2-fold, 3-fold, 5-fold, or 10-fold increased polypeptide or protein level in vivo as compared to a native mRNA that encodes the same polypeptide or protein.

In certain embodiments, a translatable molecule can provide increased levels of a polypeptide or protein in vivo as compared to a native mRNA that encodes the same polypeptide or protein. For example, the level of a polypeptide or protein can be increased by 10%, or 20%, or 30%, or 40%, or 50%, or more.

In additional embodiments, this invention provides methods for treating a disease or condition in a subject by administering to the subject a composition containing a translatable molecule of the invention.

A translatable molecule of this invention may be used for ameliorating, preventing or treating a disease. In these embodiments, a composition comprising a translatable molecule of this invention can be administered to regulate, modulate, or increase the concentration or effectiveness of the natural enzyme in a subject. In some aspects, the enzyme can be an unmodified, natural enzyme for which the patient has an abnormal quantity. In exemplary embodiments, a translatable molecule of this invention may be used for ameliorating, preventing or treating phenylketonuria (PKU).

In some embodiments, a translatable molecule may be delivered to cells or subjects, and translated to increase PAH levels in the cell or subject.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

In an exemplary embodiment, a subject of the present invention is a subject with phenylketonuria or at risk of developing phenylketonuria. In a further exemplary embodiment, the subject is a human.

In some embodiments, administering a composition comprising a translatable molecule of the invention can result in increased liver PAH protein levels in a treated subject. In some embodiments, administering a composition comprising a translatable molecule of the invention results in a 5%, 10%, 20%, 30%, 40%, 50%, 60%, 70%, 80%, 90%, or 95% increase in liver PAH protein levels relative to a baseline PAH protein level in the subject prior to treatment. In an exemplary embodiment, administering a composition comprising a translatable molecule of the invention results in an increase in liver PAH levels relative to baseline liver PAH levels in the subject prior to treatment. In some embodiments, the increase in liver PAH levels can be at least 5%, 10%, 20%, 30%, 40%, 50%, 100%, 200%, or more.

In some embodiments, the PAH protein which is expressed from a translatable molecule of the invention is detectable in the liver, serum, plasma, kidney, heart, muscle, brain, cerebrospinal fluid, or lymph nodes.

In exemplary embodiments, the PAH protein is expressed in the liver cells, e.g., hepatocytes of a treated subject.

In some embodiments, administering a composition comprising a translatable molecule of the invention results in the expression of a PAH protein level at or above about 10 ng/mg, about 20 ng/mg, about 50 ng/mg, about 100 ng/mg, about 150 ng/mg, about 200 ng/mg, about 250 ng/mg, about 300 ng/mg, about 350 ng/mg, about 400 ng/mg, about 450 ng/mg, about 500 ng/mg, about 600 ng/mg, about 700 ng/mg, about 800 ng/mg, about 900 ng/mg, about 1000 ng/mg, about 1200 ng/mg or about 1500 ng/mg of the total protein in the liver of a treated subject.

In some embodiments, the expression of the PAH protein is detectable 6, 12, 18, 24, 30, 36, 48, 60, and/or 72 hours after administration of a composition comprising a translatable molecule of the invention. In some embodiments, the expression of the PAH protein is detectable 1 day, 2 days, 3 days, 4 days, 5 days, 6 days, and/or 7 days after administration of a composition comprising a translatable molecule of the invention. In some embodiments, the expression of the PAH protein is detectable 1 week, 2 weeks, 3 weeks, and/or 4 weeks after the administration. In some embodiments, the expression of the PAH protein is detectable after administration of a composition comprising a translatable molecule of the invention. In some embodiments, expression of PAH protein is detectable in the liver, e.g., hepatocytes, after administration of a composition comprising a translatable molecule of the invention.

Variant Templates for Making Translatable Molecules

In various embodiments described herein, the translatable oligomer may comprise a mRNA encoding PAH, wherein the mRNA encoding PAH is codon-optimized. In some embodiments, the PAH is human PAH. In some embodiments, the human PAH comprises an amino acid sequence of SEQ ID NO: 2. In some embodiments, the human PAH consists of an amino acid sequence of SEQ ID NO: 2.

In some embodiments, a variant DNA template may be utilized to make a translatable molecule capable of encoding PAH. A variant DNA template of this disclosure may exhibit advantages in processes for making a translatable molecule, and the efficiency of the translatable molecule. Variation of the template can be utilized to enhance incorporation of modified nucleotides or monomers in a translatable molecule of this invention. In certain aspects, variation of the template can be utilized to enhance the structural features of the translatable molecule. The enhanced structural features of the translatable molecule can provide unexpectedly advantageous properties, including translation efficiency to provide a polypeptide or protein product.

In some aspects of this invention, variation of the template may include reducing the occurrence or frequency of appearance of certain nucleotides in the template strand. Reducing the occurrence of a certain nucleotide can alter the structures and processes of this disclosure to provide non-native forms, which achieve surprisingly improved properties of a translatable RNA product encoding PAH.

Aspects of this invention may require a variant DNA template in processes for making a translatable molecule. A DNA molecule can have a non-coding template strand of nucleotides that can be transcribed to provide a target translatable molecule encoding PAH.

A target translatable molecule can be any RNA, whether native or modified, synthetic or derived from a natural source.

In some embodiments, a variant DNA template can be used for which an open reading frame of the template strand is transformed to an alternative form, while preserving codon assignment.

In certain embodiments, a DNA template can be used for which alternative nucleotides are used based on alternative codon optimization and/or sequence degeneracy.

In additional embodiments, a DNA template may have certain nucleotides replaced with alternative nucleotides, while preserving codon assignment.

Embodiments of this invention advantageously utilize alternative codons in a DNA template of this invention to be used in processes for making a translatable molecule encoding PAH. The variations that can be achieved in a DNA template of this invention can be far greater in scope than for cells and organisms, which may require preferred codons in many processes. In this invention, a wide range of alternative codons and positions can be used in a DNA template for transcribing a translatable molecule.

In further aspects of this invention, variation of the template may include reducing the occurrence or frequency of appearance of certain nucleotides in the template strand. For example, the occurrence of a nucleotide in a template may be reduced to a level below 25% of nucleotides in the template. In further examples, the occurrence of a nucleotide in a template may be reduced to a level below 20% of nucleotides in the template. In some examples, the occurrence of a nucleotide in a template may be reduced to a level below 16% of nucleotides in the template. In certain examples, the occurrence of a nucleotide in a template may be reduced to a level below 12% of nucleotides in the template.

Human PAH

The human PAH gene encodes a 452 amino acid protein with a predicted MW of 51.862 kDa. PAH is a cytoplasmic enzyme expressed primarily in hepatocytes that functions as a homotetramer, i.e., a dimer of dimers. Each monomer contains a N-terminal regulatory domain, residues 1-142, a catalytic domain, residues 143-410, and a C-terminal oligomerization domain, residues 411-452. The regulatory domain, which inhibits the enzyme when bound to tetrahydrobiopterin, is de-repressed upon binding of substrate, L-Phe. It then catalyzes the catabolism of phenylalanine to tyrosine. Phosphorylation of Ser16 is known to increase the activity of the enzyme. Ser16Glu mutation mimics the phosphorylation and may also stabilize the protein. The protein half-life in rats from pulse-chase experiments is about 2 hours.

Phe is an essential amino acid, which is used to make tyrosine (Tyr) in the liver. This reaction is catalyzed by the activity of PAH, a non-heme, iron dependent enzyme. Phe accumulation, due to pathway blockade at the PAH catalyzed step, is neurotoxic in PKU patients.

Because the human-mouse protein homology is 92.3%, gene transfer of a human enzyme can result in metabolic control in a mouse model of PKU. Meanwhile, protein homology for human-rhesus macaque is higher, at 98.0%, UniProtKB-F7HMW9 (F7HMW9_MACMU).

Human wild type PAH mRNA is reference accession NM_000277.1.

The consensus human PAH coding sequence CCDS9092.1 (1359 nt) has a DNA sequence shown in SEQ ID NO: 1. CCDS9092.1 translates into SEQ ID NO: 2.

In some embodiments, a translatable molecule can be made and used for expressing human phenylalanine hydroxylase (hPAH) with advantageously increased efficiency of translation, as compared to a native mRNA of hPAH. The translatable molecule expressing hPAH may exhibit activity suitable for use in methods for ameliorating, preventing or treating disease. In some embodiments, the translatable molecule may comprise one or more UNA monomers.

In some embodiments, a translatable molecule may include a 5' cap, a 5' UTR, a translation initiation sequence, e.g., a Kozak sequence, a human PAH CDS, a 3'UTR, and/or a tail region. In an exemplary embodiment, a translatable molecule may include a 5' cap (m7GpppGm), a 5' UTR of tobacco etch virus (TEV), a Kozak sequence, a human PAH CDS, a 3' UTR of *Xenopus* beta-globin, and a tail region. In further exemplary embodiments, the human PAH CDS may comprise a codon-optimized sequence of SEQ ID NOs: 8-37 or SEQ ID Nos: 45-46, described in further detail below. In any of these and other embodiments described herein, the translatable molecule may comprise one or more UNA monomers. In any of these and other embodiments described herein, the translatable molecule may comprise one or more LNA monomers.

The translation efficiency of the molecule can be increased as compared to a native mRNA of PAH. In particular, after 48 hours, the translation efficiency of the molecule may be more than doubled as compared to the native mRNA of PAH.

In some embodiments, a suitable mRNA sequence for the present invention comprises an mRNA sequence encoding the human PAH protein. The sequence of the naturally occurring human PAH protein is shown in SEQ ID NO: 2.

In some embodiments, a suitable mRNA sequence may be an mRNA sequence that encodes a homolog or variant of human PAH. As used herein, a homolog or a variant of human PAH protein may be a modified human PAH protein containing one or more amino acid substitutions, deletions, and/or insertions as compared to a wild-type or naturally-occurring human PAH protein while retaining substantial PAH protein activity. In some embodiments, an mRNA suitable for the present invention encodes a protein substantially identical to human PAH protein. In some embodiments, an mRNA suitable for the present invention encodes an amino acid sequence at least 80%, 85%, 90%, 91%, 92%, 93%, 94%, 95%, 96%, 97%, 98%, 99% or more identical to SEQ ID NO: 2. In some embodiments, an mRNA suitable for the present invention encodes a fragment or a portion of human PAH protein.

In some embodiments, an mRNA suitable for the present invention encodes a fragment or a portion of human PAH protein, wherein the fragment or portion of the protein still maintains PAH activity similar to that of the wild-type protein.

In some embodiments, an mRNA suitable for the present invention comprises a sequence that is at least 80%, 85%, 90%, 91%, 92%, 93%, 94%, 95%, 96%, 97%, 98%, 99% or more identical to SEQ ID NOs: 8-37 or SEQ ID Nos: 45-46.

In some embodiments, a translatable oligomeric molecule of the present invention comprises a coding sequence that is at least 80%, 85%, 90%, 91%, 92%, 93%, 94%, 95%, 96%, 97%, 98%, 99% or more identical to SEQ ID NOs: 8-37 or SEQ ID Nos: 45-46. In some embodiments, a translatable oligomeric molecule comprising a coding sequence that is at least 80%, 85%, 90%, 91%, 92%, 93%, 94%, 95%, 96%, 97%, 98%, 99% or more identical to SEQ ID NOs: 8-37 or SEQ ID Nos: 45-46 further comprises one or more sequences selected from a 5' cap, a 5' UTR, a translation initiation sequence, a 3' UTR, and a tail region.

In some embodiments, a translatable oligomeric molecule of the invention encodes a fusion protein comprising a full length, fragment or portion of a PAH protein fused to another sequence (e.g., an N or C terminal fusion). In some embodiments, the N or C terminal sequence is a signal sequence or a cellular targeting sequence.

UNA Monomers and Oligomers

In some embodiments, linker group monomers can be unlocked nucleomonomers (UNA monomers), which are small organic molecules based on a propane-1,2,3-tri-yl-trisoxy structure as shown below:

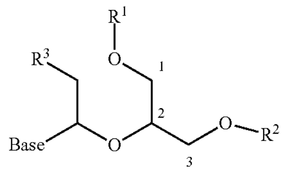

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

UNA monomer unit

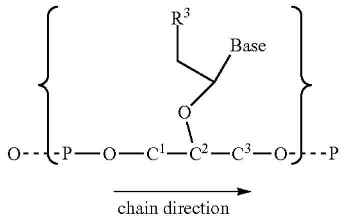

chain direction where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

Examples of a nucleobase include pseudouracil, 1-methylpseudouracil (m1Ψ), i.e., $N^1$-methylpseudouracil, and 5-methoxyuracil.

In general, a UNA monomer, which is not a nucleotide, can be an internal linker monomer in an oligomer. An internal UNA monomer in an oligomer is flanked by other monomers on both sides.

A UNA monomer can participate in base pairing when the oligomer forms a complex or duplex, for example, and there are other monomers with nucleobases in the complex or duplex.

Examples of UNA monomer as internal monomers flanked at both the propane-1-yl position and the propane-3-yl position, where $R^3$ is —OH, are shown below.

UNA-A

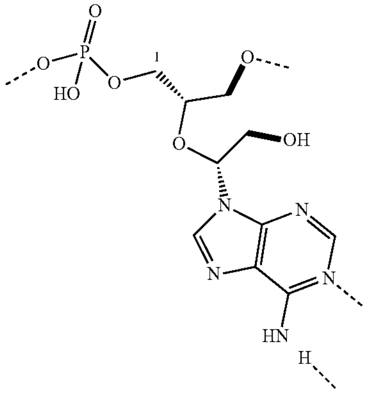

UNA-U

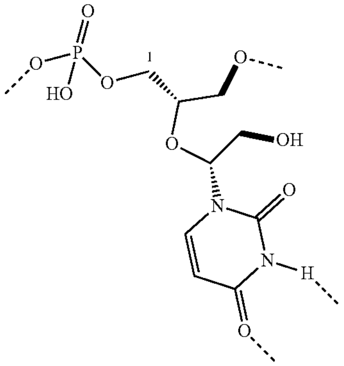

UNA-C

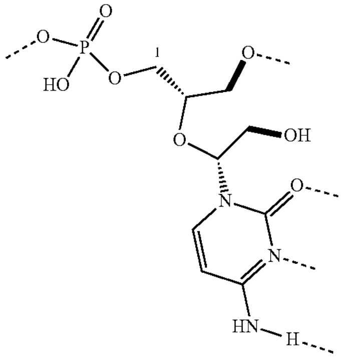

UNA-G

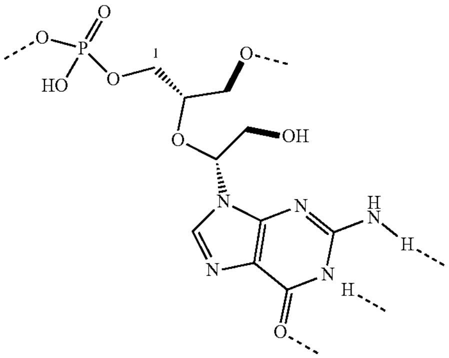

A UNA monomer can be a terminal monomer of an oligomer, where the UNA monomer is attached to only one monomer at either the propane-1-yl position or the propane-3-yl position. Because the UNA monomers are flexible organic structures, unlike nucleotides, the terminal UNA monomer can be a flexible terminator for the oligomer.

Examples of a UNA monomer as a terminal monomer attached at the propane-3-yl position are shown below.

terminal UNA-A

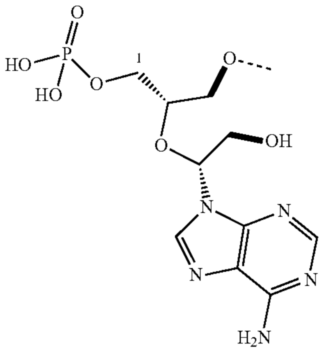

terminal UNA-U

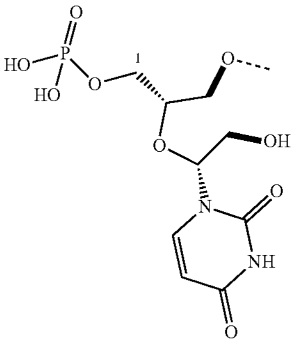

terminal UNA-C

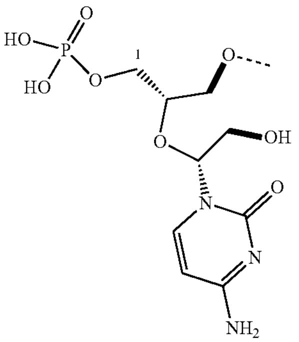

terminal UNA-G

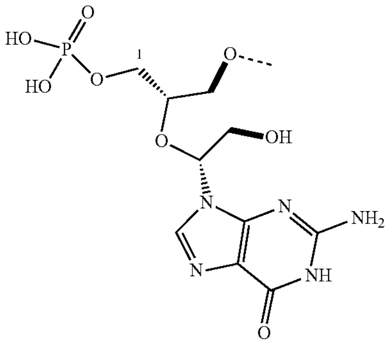

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

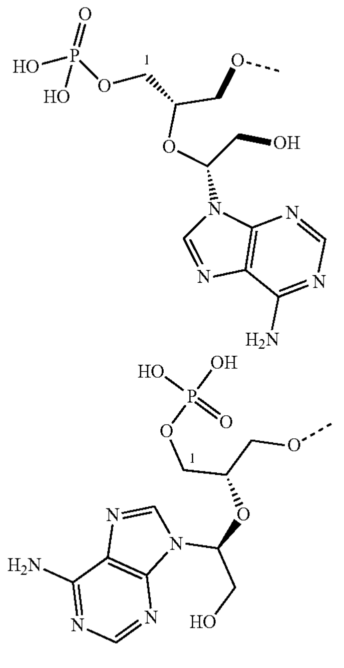

UNA-A Terminal Forms: The Dashed Bond Shows the Propane-3-yl Attachment

Among other things, the structure of the UNA monomer allows it to be attached to naturally-occurring nucleotides.

A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4_2$, —NH(C═O)$R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule.

In some embodiments, as shown above, a UNA monomer can be UNA-A (designated Ã), UNA-U (designated Ũ), UNA-C (designated C̃), and UNA-G (designated G̃).

Designations that may be used herein include mA, mG, mC, and mU, which refer to the 2'-O-Methyl modified ribonucleotides.

Designations that may be used herein include dT, which refers to a 2'-deoxy T nucleotide.

As used herein, in the context of oligomer sequences, the symbol N can represent any natural nucleotide monomer, or any modified nucleotide monomer.

As used herein, in the context of oligomer sequences, the symbol Q represents a non-natural, modified, or chemically-modified nucleotide monomer.

As used herein, in the context of oligomer sequences, the symbol X may be used to represent a UNA monomer.

Modified and Chemically-Modified Nucleotides

In the examples of modified or chemically-modified nucleotides herein, an alkyl, cycloalkyl, or phenyl substituent may be unsubstituted, or further substituted with one or more alkyl, halo, haloalkyl, amino, or nitro substituents.

Examples of nucleic acid monomers include non-natural, modified, and chemically-modified nucleotides, including any such nucleotides known in the art.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4$,$N^4$-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4$,$N^4$-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine, 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyladenosine, $N^6$,$N^6$-dimethyladenosine, N6-hydroxynorvalylcarbamoyladenosine, 2-methylthio-$N^6$-hydroxynorvalylcarbamoyl-adenosine, $N^6$-acetyladenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6$,$N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include $N^1$-alkylguanosines, $N^2$-alkylguanosines, thienoguanosines, 7-deazaguanosines, 8-oxoguanosines, 8-bromoguanosines, $O^6$-alkylguanosines, xanthosines, inosines, and $N^1$-alkylinosines.

Examples of modified or chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Examples of modified or chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, $N^1$-phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^1$-alkyl-$N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include $N^1$-methylpseudouridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include $N^6$-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Some examples of modified nucleotides are given in Saenger, Principles of Nucleic Acid Structure, Springer-Verlag, 1984.

Example of base modifications described above can be combined with additional modifications of nucleoside or nucleotide structure, including sugar modifications and linkage modifications.

Certain modified or chemically-modified nucleotide monomers may be found in nature.

Translatable Molecules Containing One or More UNA Monomers

Aspects of this invention provide structures and compositions for translatable molecules that are oligomeric compounds containing one or more UNA monomers. The translatable oligomers can be active agents for pharmaceutical compositions. In some embodiments, the translatable oligomers encode human PAH or a variant thereof.

An oligomeric, translatable molecule of this invention may contain one or more UNA monomers. Oligomeric molecules of this invention can be used as active agents in formulations for supplying peptide and protein therapeutics. In some embodiments, the translatable oligomers encode human PAH or a variant thereof.

In some embodiments, this invention provides oligomeric, translatable compounds having a structure that incorporates novel combinations of UNA monomers with certain natural nucleotides, non-natural nucleotides, modified nucleotides, or chemically-modified nucleotides.

Translatable oligomeric compounds of this invention can have a length of from about 200 to about 12,000 bases in length. Translatable oligomeric compounds of this invention can have a length of about 1500, 1600, 1700, 1800, or about 1900, or about 2000, or about 2100, or about 2200, or about 2300, or about 2400, or about 2500 bases. In an exemplary embodiment, the translatable oligomeric compound of the invention has a length of about 1800 bases.

In further aspects, the oligomeric, translatable compounds of this invention which comprise one or more UNA monomers can be pharmacologically active molecules. A translatable oligomeric molecule can be used as an active pharmaceutical ingredient for generating a peptide or protein active agent in vitro, in vivo, or ex vivo. In an exemplary embodiment, the translatable oligomeric compound of this invention encodes human PAH or a variant thereof.

A translatable oligomeric molecule of this invention can have the structure of Formula I:

Formula I

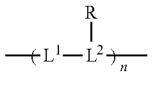

wherein $L^1$ is a linkage, n is from 200 to 12,000, and for each occurrence $L^2$ is a UNA linker group having the formula $—C^1\text{-}C^2\text{-}C^3—$, where R is attached to $C^2$ and has the formula $—OCH(CH_2R^3)R^5$, where $R^3$ is $—OR^4$, $—SR^4$, $—NR^4_2$, $—NH(C{=}O)R^4$, morpholino, morpholin-1-yl, piperazin-1-yl, or 4-alkanoyl-piperazin-1-yl, where $R^4$ is the same or different for each occurrence and is H, alkyl, a cholesterol, a lipid molecule, a polyamine, an amino acid, or a polypeptide, and where $R^5$ is a nucleobase, or $L^2(R)$ is a sugar such as a ribose and R is a nucleobase, or $L^2$ is a modified sugar such as a modified ribose and R is a nucleobase. In certain embodiments, a nucleobase can be a modified nucleobase. $L^1$ can be a phosphodiester linkage.

The base sequence of a translatable oligomeric molecule can be any sequence of nucleobases.

In some aspects, a translatable oligomeric molecule of this invention can have any number of phosphorothioate intermonomer linkages in any intermonomer location.

In some embodiments, any one or more of the intermonomer linkages of a translatable oligomeric molecule can be a phosphodiester, a phosphorothioate including dithioates, a chiral phosphorothioate, and other chemically modified forms.

When a translatable oligomeric molecule terminates in a UNA monomer, the terminal position has a 1-end, or the terminal position has a 3-end, according to the positional numbering shown above.

Enhanced Translation

A translatable molecule of this invention can incorporate a region that enhances the translational efficiency of the molecule.

In general, translational enhancer regions as known in the art can be incorporated into the structure of a translatable molecule to increase peptide or protein yields.

A translatable molecule containing a translation enhancer region can provide increased production of peptide or protein.

In some embodiments, a translation enhancer region can comprise, or be located in a 5' or 3' untranslated region of a translatable molecule.

Examples of translation enhancer regions include naturally-occurring enhancer regions from TEV 5'UTR and *Xenopus* beta-globin 3'UTR.

Molecular Structures and Sequences

A translatable molecule can be designed to express a target peptide or protein. In some embodiments, the target peptide or protein can be associated with a condition or disease in a subject.

In some aspects, the base sequence of a translatable molecule can include a portion that is identical to at least an effective portion or domain of a base sequence of an mRNA, where an effective portion is sufficient to impart a therapeutic activity to a translation product of the translatable molecule.

In some aspects, this invention provides active translatable molecules having a base sequence identical to at least a fragment of a native nucleic acid molecule of a cell.

In certain embodiments, the base sequence of a translatable molecule can include a portion that is identical to a base sequence of an mRNA, except for one or more base mutations. The number of mutations for the translatable molecule should not exceed an amount that would produce a translation product of the translatable molecule having substantially less activity than the mRNA.

The oligomeric, translatable UNA molecules of this invention can display a sequence of nucleobases, and can be designed to express a peptide or protein, in vitro, ex vivo, or in vivo. The expressed peptide or protein can have activity in various forms, including activity corresponding to protein expressed from a native or natural mRNA.

In some embodiments, a translatable molecule of this invention may have a chain length of about 400 to 15,000 monomers, where any monomer that is not a UNA monomer can be an N or Q monomer.

Molecular Cap Structure

A translatable molecule of this invention may have a 5'-end capped with various groups and their analogues as are known in the art. In an exemplary embodiment, the 5' cap may be a m7GpppGm cap. In further embodiments, the 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7, 2'OmeGpppG, m72'dGpppG, m7,3'OmeGpppG, m7,3'dGpppG and their tetraphosphate derivatives) (see, e.g., Jemielity, J. et al., RNA 9: 1108-1122 (2003). In other embodiments, the 5' cap may be an ARCA cap (3'-OMe-m7G(5')pppG). The 5' cap may be an mCAP (m7G(5')ppp(5')G, $N^7$-Methyl-Guanosine-5'-Triphosphate-5'-Guanosine). The 5' cap may be resistant to hydrolysis.

Some examples of 5' cap structures are given in WO2015/051169A2, WO/2015/061491, and U.S. Pat. Nos. 8,093,367 and 8,304,529.

Tail Region

In some embodiments, the translatable oligomer encoding PAH comprises a tail region, which can serve to protect the mRNA from exonuclease degradation. In some embodiments, the tail region can be a polyA tail.

PolyA tails can be added using a variety of methods known in the art, e.g., using poly A polymerase to add tails to synthetic or in vitro transcribed RNA. Other methods include the use of a transcription vector to encode poly A tails or the use of a ligase (e.g., via splint ligation using a T4 RNA ligase and/or T4 DNA ligase), wherein polyA may be ligated to the 3' end of a sense RNA. In some embodiments, a combination of any of the above methods is utilized.

In some embodiments, a translatable oligomer comprises a 3' polyA tail structure. In some embodiments, the length of the polyA tail can be at least about 5, 10, 15, 20, 25, 30, 35, 40, 45, 50, 100, 200, or 300 nucleotides. In some embodiments, a 3' polyA tail contains about 5 to 300 adenosine nucleotides (e.g., about 30 to 250 adenosine nucleotides, about 60 to 220 adenosine nucleotides, about 80 to 200 adenosine nucleotides, about 90 to about 150 adenosine nucleotides, or about 100 to about 120 adenosine nucleotides). In an exemplary embodiment, the 3' polyA tail is about 100 nucleotides in length. In another exemplary embodiment, the 3' polyA tail is about 115 nucleotides in length.

In some embodiments, the 3' polyA tail comprises one or more UNA monomers. In some embodiments, the 3' polyA tail contains 2, 3, 4, 5, 10, 15, 20, or more UNA monomers. In an exemplary embodiment, the 3' polyA tail contains 2 UNA monomers. In a further exemplary embodiment, the 3' polyA tail contains 2 UNA monomers which are found consecutively, i.e., contiguous to each other in the 3' polyA tail.

In an exemplary embodiment, the 3' polyA tail comprises or consists of a sequence shown in SEQ ID NO: 7. In another exemplary embodiment, the 3' polyA tail comprises or consists of a sequence shown in SEQ ID NO: 43.

In some embodiments, the translatable oligomer comprises a 3' polyC tail structure. In some embodiments, the length of the polyC tail can be at least about 5, 10, 15, 20, 25, 30, 35, 40, 45, 50, 100, 200, or 300 nucleotides. In some embodiments, a 3' polyC tail contains about 5 to 300 cytosine nucleotides (e.g., about 30 to 250 cytosine nucleotides, about 60 to 220 cytosine nucleotides, about 80 to about 200 cytosine nucleotides, about 90 to 150 cytosine nucleotides, or about 100 to about 120 cytosine nucleotides). In an exemplary embodiment, the 3' polyC tail is about 100 nucleotides in length. In another exemplary embodiment, the 3' polyC tail is about 115 nucleotides in length. The polyC tail may be added to the polyA tail or may substitute the polyA tail. The polyC tail may be added to the 5' end of the polyA tail or the 3' end of the polyA tail.

In some embodiments, the length of the poly A and/or poly C tail is adjusted to control the stability of a modified translatable oligomeric molecule of the invention and, thus, the transcription of protein. For example, since the length of the polyA tail can influence the half-life of a translatable molecule, the length of the polyA tail can be adjusted to modify the level of resistance of the mRNA to nucleases and thereby control the time course of polynucleotide expression and/or polypeptide production in a target cell.

5' and 3' Untranslated Regions (UTRs)

In some embodiments, the translatable oligomer encoding PAH may comprise a 5' untranslated region and/or a 3' untranslated region. As is understood in the art, the 5' and/or 3' UTR may affect an mRNA's stability or efficiency of translation. In an exemplary embodiment, the translatable oligomer comprises a 5' UTR and a 3' UTR.

In some embodiments, the translatable oligomer may comprise a 5' UTR that is at least about 25, 50, 75, 100, 125, 150, 175, 200, 300, 400, or 500 nucleotides. In some embodiments, a 5' UTR contains about 50 to 300 nucleotides (e.g., about 75 to 250 nucleotides, about 100 to 200 nucleotides, about 120 to 150 nucleotides, or about 135 nucleotides). In an exemplary embodiment, the 5' UTR is about 135 nucleotides in length.

In some embodiments, the 5' UTR is derived from an mRNA molecule known in the art to be relatively stable (e.g., histone, tubulin, globin, GAPDH, actin, or citric acid cycle enzymes) to increase the stability of the translatable oligomer. In other embodiments, a 5' UTR sequence may include a partial sequence of a CMV immediate-early 1 (IE1) gene. Examples of 5' UTR sequences may be found in U.S. Pat. No. 9,149,506. In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK, AT1G58420, mouse beta globin, mouse albumin, and a tobacco etch virus, or fragments of any of the foregoing. In an exemplary embodiment, the 5' UTR is derived from a tobacco etch virus (TEV). In a further exemplary embodiment, the 5' UTR comprises or consists of a sequence set forth in SEQ ID NO: 3. In yet another exemplary embodiment, the 5' UTR is a fragment of a sequence set forth in SEQ ID NO: 3, such as a fragment of at least 10, 20, 30, 40, 50, 60, 70, 80, 90, 100, 110, 120, or 125 contiguous nucleotides of SEQ ID NO: 3.

In some embodiments, the translatable oligomeric molecule comprises an internal ribosome entry site (IRES). As is understood in the art, an IRES is an RNA element that allows for translation initiation in an end-independent manner. In exemplary embodiments, the IRES is in the 5' UTR. In other embodiments, the IRES may be outside the 5' UTR.

In some embodiments, the translatable oligomer may comprise a 3' UTR that is at least about 25, 50, 75, 100, 125, 150, 175, 200, 300, 400, or 500 nucleotides. In some embodiments, a 3' UTR contains about 50 to 300 nucleotides (e.g., about 75 to 250 nucleotides, about 100 to 200 nucleotides, about 140 to 175 nucleotides, or about 160 nucleotides). In an exemplary embodiment, the 3' UTR is about 160 nucleotides in length.

In some embodiments, the 3' UTR comprises one or more UNA monomers. In some embodiments, the 3' UTR contains 2, 3, 4, 5, 10, 15, 20, or more UNA monomers.

Examples of 3' UTR sequences may be found in U.S. Pat. No. 9,149,506. In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *Xenopus* beta globin, or fragments of any of the foregoing. In an exemplary embodiment, the 3' UTR is derived from *Xenopus* beta globin. In another exemplary embodiment, the 3' UTR is derived from *Xenopus* beta globin and contains one or more UNA monomers. In a further exemplary embodiment, the 3' UTR comprises or consists of a sequence set forth in SEQ ID NOs: 6 and 38-42. In yet another exemplary embodiment, the 3' UTR is a fragment of a sequence set forth in SEQ ID NOs: 6 and 38-42, such as a fragment of at least 10, 20, 30, 40, 50, 60, 70, 80, 90, 100, 110, 120, 130, 140, or 150 contiguous nucleotides of SEQ ID NO: 6 and 38-42.

In certain exemplary embodiments, the translatable oligomer encoding PAH comprises a 5' UTR sequence of SEQ ID NO: 3 and a 3' UTR sequence selected from SEQ ID NOs: 6 and 38-42. In some embodiments, the translatable oligomer encoding PAH further comprises a polyA tail shown in SEQ ID NO: 7 or SEQ ID NO: 43. In some embodiments, the mRNA coding sequence of PAH comprises a sequence selected from SEQ ID NOs: 8-37 or SEQ ID Nos: 45-46.

Triple Stop Codon

In some embodiments, the translatable oligomer encoding PAH may comprise a sequence immediately downstream of the CDS that creates a triple stop codon. The triple stop codon may be incorporated to enhance the efficiency of translation. In some embodiments, the transatable oligomer may comprise the sequence AUAAGUGAA (SEQ ID NO: 44) immediately downstream of a PAH CDS described herein, as exemplified in SEQ ID NOs: 8-37 or SEQ ID Nos: 45-46.

Translation Initiation Sites

In some embodiments, the translatable oligomer encoding PAH may comprise a translation initiation site. Such sequences are known in the art and include the Kozak sequence. See, for example, Kozak, Marilyn (1988) Mol. and Cell Biol., 8:2737-2744; Kozak, Marilyn (1991) J. Biol. Chem., 266:19867-19870; Kozak, Marilyn (1990) Proc Natl. Acad. Sci. USA, 87:8301-8305; and Kozak, Marilyn (1989) J. Cell Biol., 108:229-241; and the references cited therein. As is understood in the art, a Kozak sequence is a short consensus sequence centered around the translational initiation site of eukaryotic mRNAs that allows for efficient initiation of translation of the mRNA. The ribosomal translation machinery recognizes the AUG initiation codon in the context of the Kozak sequence.

In some embodiments, the translation initiation site, e.g., a Kozak sequence, is inserted upstream of the coding sequence for PAH. In some embodiments, the translation initiation site is inserted downstream of a 5' UTR. In certain exemplary embodiments, the translation initiation site is inserted upstream of the coding sequence for PAH and downstream of a 5' UTR.

As is understood in the art, the length of the Kozak sequence may vary. Generally, increasing the length of the leader sequence enhances translation.

In some embodiments, the translatable oligomer encoding PAH comprises a Kozak sequence having the sequence of SEQ ID NO: 4. In certain exemplary embodiments, the translatable oligomer encoding PAH comprises a Kozak sequence having the sequence of SEQ ID NO: 4, wherein the Kozak sequence is immediately downstream of a 5' UTR and immediately upstream of the coding sequence for PAH.

Synthesis Methods

In various aspects, this invention provides methods for synthesis of translatable messenger molecules.

Translatable molecules of this invention can be synthesized and isolated using methods disclosed herein, as well as any pertinent techniques known in the art.

Some methods for preparing nucleic acids are given in, for example, Merino, Chemical Synthesis of Nucleoside Analogues, (2013); Gait, Oligonucleotide synthesis: a practical approach (1984); Herdewijn, Oligonucleotide Synthesis, Methods in Molecular Biology, Vol. 288 (2005).

In some embodiments, a translatable molecule can be made by in vitro transcription (IVT) reaction. A mix of nucleoside triphosphates (NTP) can be polymerized using T7 reagents, for example, to yield RNA from a DNA template. The DNA template can be degraded with RNase-free DNase, and the RNA column-separated.

In some embodiments, a ligase can be used to link a synthetic oligomer to the 3' end of an RNA molecule or an RNA transcript to form a translatable molecule. The synthetic oligomer that is ligated to the 3' end can provide the functionality of a polyA tail, and advantageously provide resistance to its removal by 3'-exoribonucleases. The ligated product translatable molecule can have increased specific activity and provide increased levels of ectopic protein expression.

In certain embodiments, the ligated product of the translatable molecules of this invention can be made with an RNA transcript that has native specificity. The ligated product can be a synthetic molecule that retains the structure of the RNA transcript at the 5' end to ensure compatibility with the native specificity.

In further embodiments, the ligated product of the translatable molecules of this invention can be made with an exogenous RNA transcript or non-natural RNA. The ligated product can be a synthetic molecule that retains the structure of the RNA.

Without wishing to be bound by theory, the canonical mRNA degradation pathway in cells includes the steps: (i) the polyA tail is gradually cut back to a stub by 3' exonucleases, shutting down the looping interaction required for efficient translation and leaving the cap open to attack; (ii) decapping complexes remove the 5' cap; (iii) the unprotected and translationally incompetent residuum of the transcript is degraded by 5' and 3' exonuclease activity.

Embodiments of this invention involve new translatable structures which can have increased translational activity over a native transcript. Among other things, translatable molecules herein may prevent exonucleases from trimming back the polyA tail in the process of de-adenylation.

Embodiments of this invention provide structures, compositions and methods for translatable molecules. Embodiments of this invention can provide translatable molecules containing one or more UNA monomers and having increased functional half-life.

It has been found that ligation of a synthetic oligomer to the 3' end of an mRNA transcript can surprisingly be accomplished with high conversion of the mRNA transcript to the ligation product.

As used herein, the terms polyA tail and polyA oligomer refer to an oligomer of monomers, wherein the monomers can include nucleotides based on adenine, UNA monomers, naturally-occurring nucleotides, modified nucleotides, or nucleotide analogues.

Oligomers for ligation to the 3' end of an RNA may be from 2 to 120 monomers in length, or from 3 to 120 monomers in length, or from 4 to 120 monomers in length, or from 5 to 120 monomers in length, or longer. In an exemplary embodiment, the oligomer for ligation is about 30 monomers in length.

Lipid-Based Formulations

Lipid-based formulations have been increasingly recognized as one of the most promising delivery systems for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and to deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin R A-shRNA). Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv Rev. 2014 February; 66: 110-116.)

According to some embodiments, the expressible polynucleotides and heterologous mRNA constructs described herein are lipid formulated. The lipid formulation is preferably selected from, but not limited to, liposomes, lipoplexes, copolymers, such as PLGA, and lipid nanoparticles. In one preferred embodiment, a lipid nanoparticle (LNP) comprises:

(a) a nucleic acid, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol.

In one embodiment, the lipid nanoparticle formulation consists of (i) at least one cationic lipid; (ii) a neutral lipid; (iii) a sterol, e.g., cholesterol; and (iv) a PEG-lipid, in a molar ratio of about 20-60% cationic lipid:5-25% neutral lipid:25-55% sterol; 0.5-15% PEG-lipid.

Thiocarbamate and Carbamate-Containing Lipid Formulations

Some examples of lipids and lipid compositions for delivery of an active molecule of this invention are given in WO/2015/074085 and U.S. Ser. No. 15/387,067, each of which is hereby incorporated by reference in its entirety. In certain embodiments, the lipid is a compound of the following formula:

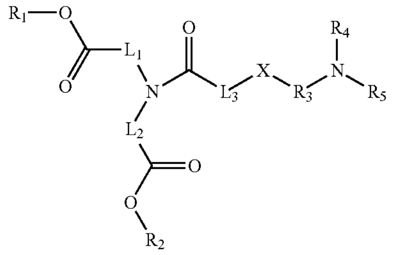

wherein $R_1$ and $R_2$ both consist of a linear alkyl consisting of 1 to 14 carbons, or an alkenyl or alkynyl consisting of 2 to 14 carbons;

$L_1$ and $L_2$ both consist of a linear alkylene or alkenylene consisting of 5 to 18 carbons, or forming a heterocycle with N;

X is S;

$L_3$ consists of a bond or a linear alkylene consisting of 1 to 6 carbons, or forming a heterocycle with N;

$R_3$ consists of a linear or branched alkylene consisting of 1 to 6 carbons; and $R_4$ and $R_5$ are the same or different, each consisting of a hydrogen or a linear or branched alkyl consisting of 1 to 6 carbons;

or a pharmaceutically acceptable salt thereof.

The lipid formulation may contain one or more ionizable cationic lipids selected from among the following:

ATX-001

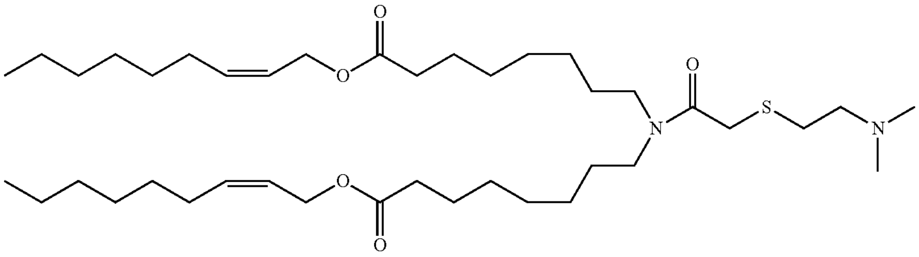

ATX-002

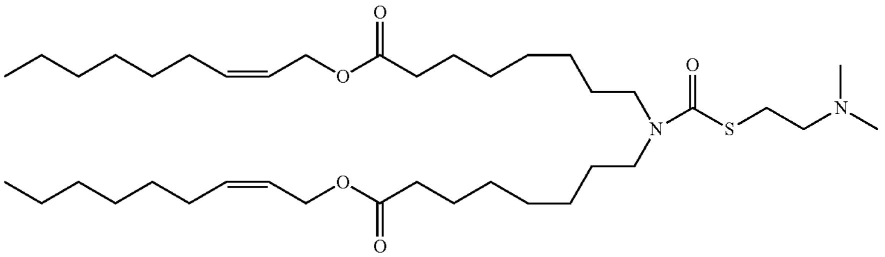

-continued
ATX-003
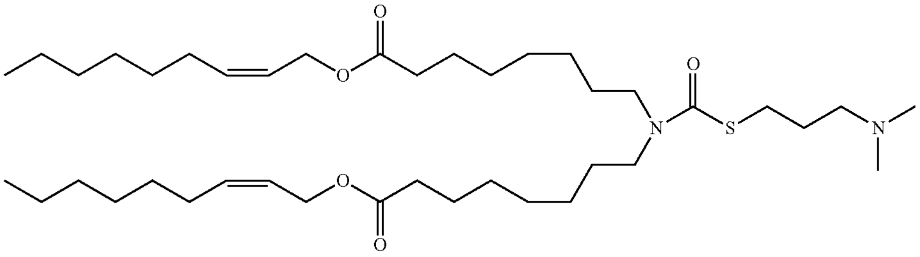
ATX-004
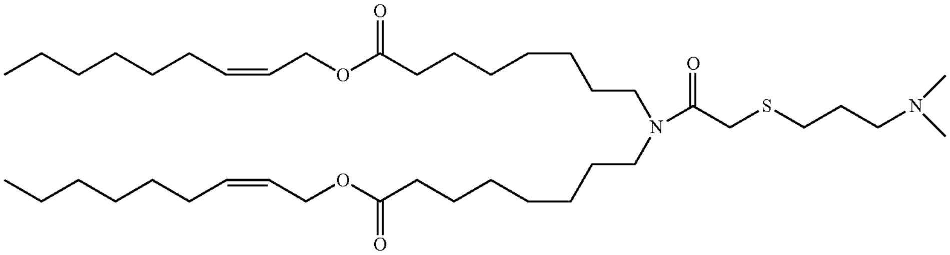
ATX-005
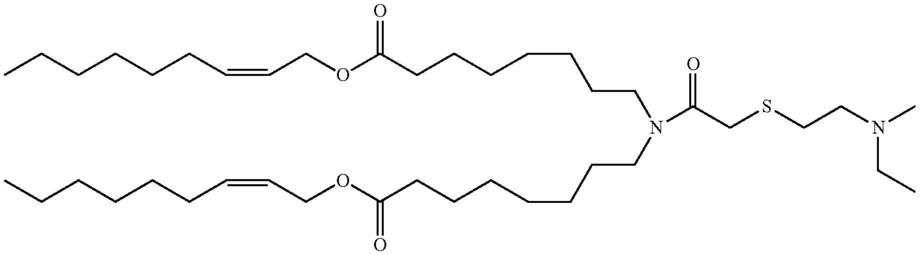
ATX-006
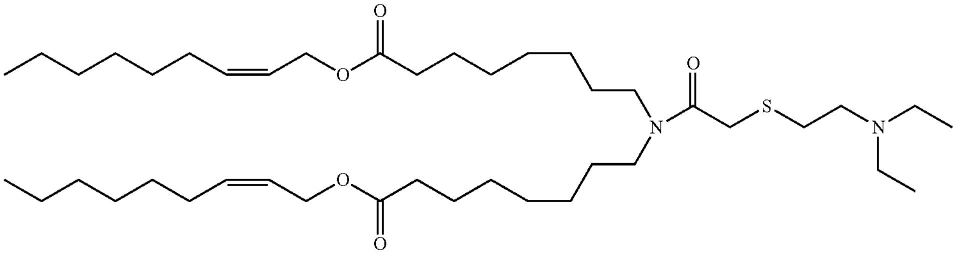
ATX-007
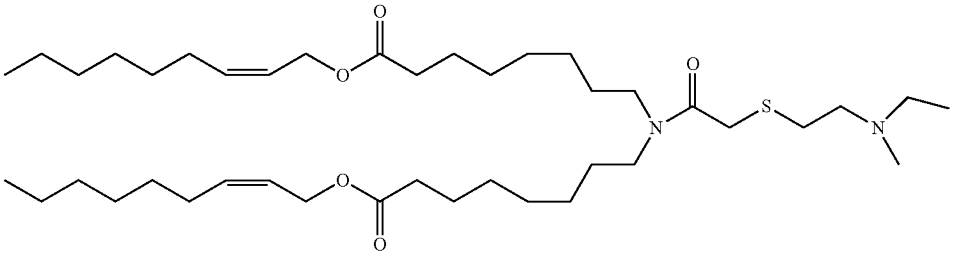
ATX-008
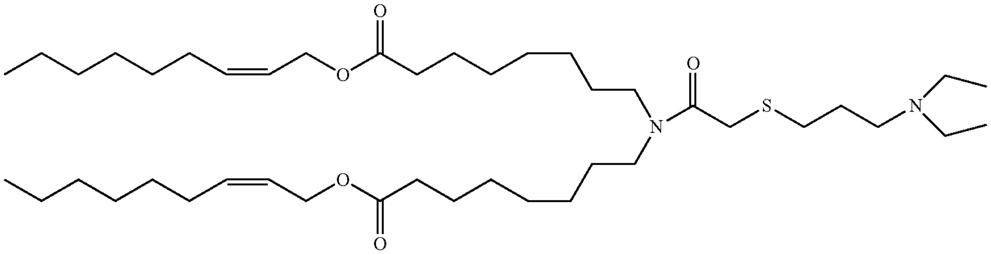

-continued
ATX-009
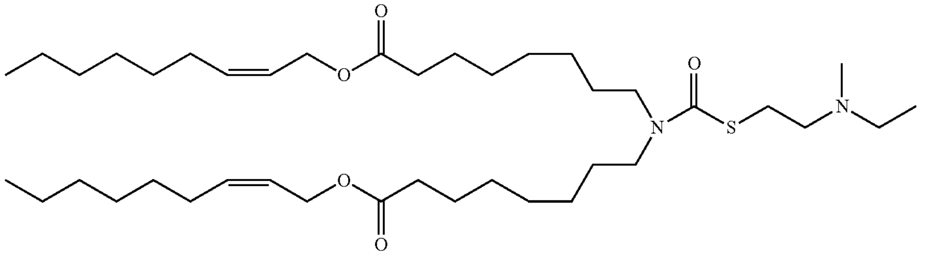
ATX-010
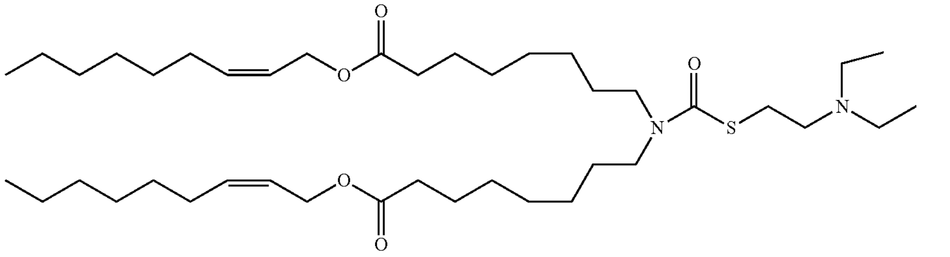
ATX-011
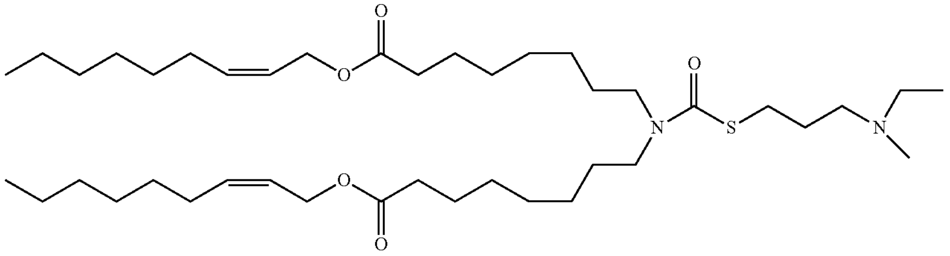
ATX-012
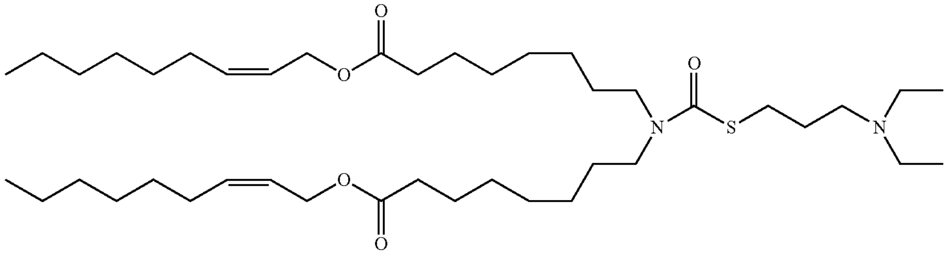
ATX-013
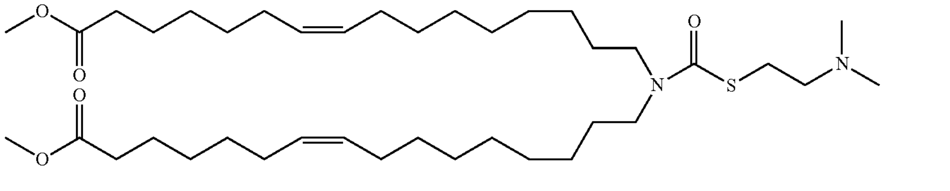
ATX-014
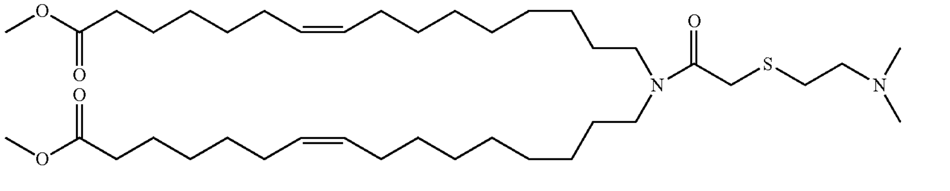
ATX-015
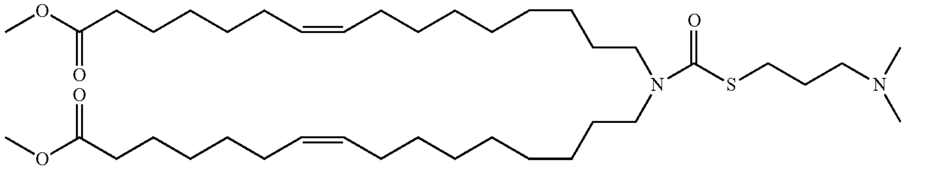

-continued
ATX-016
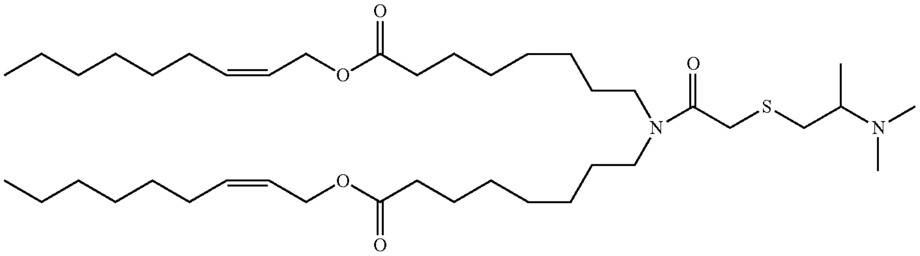
ATX-017
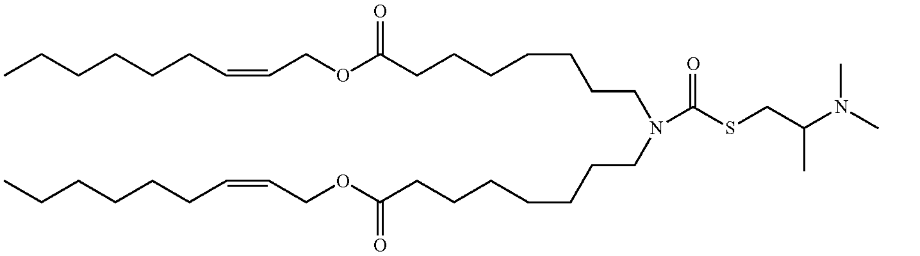
ATX-018
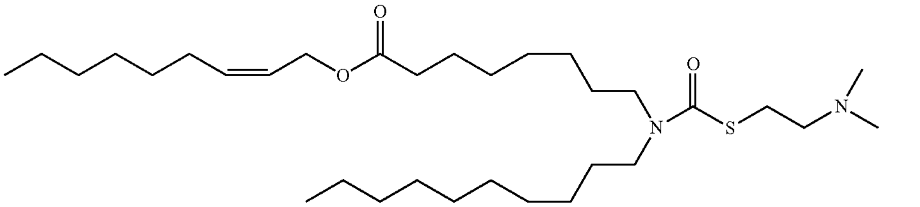
ATX-019
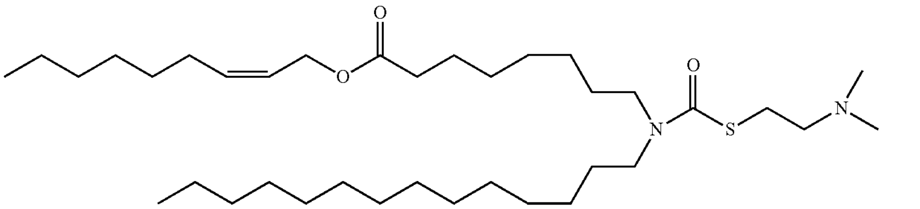
ATX-020
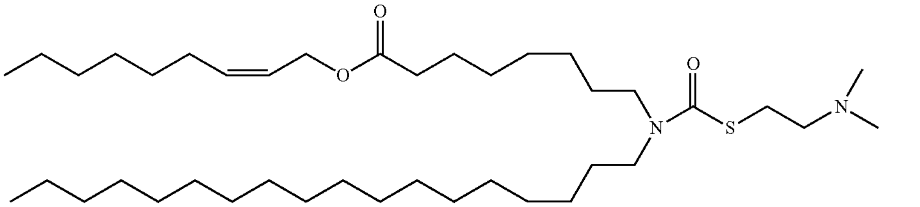
ATX-021
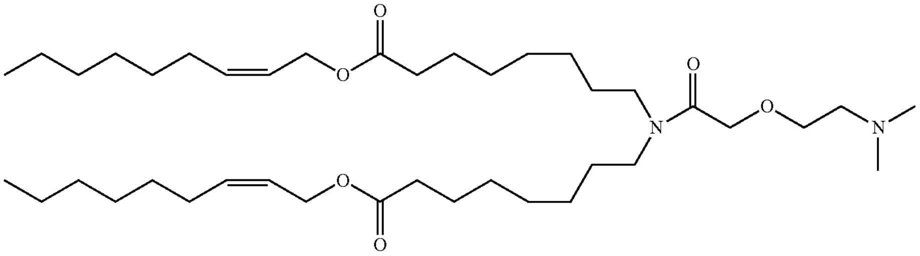

-continued
ATX-022
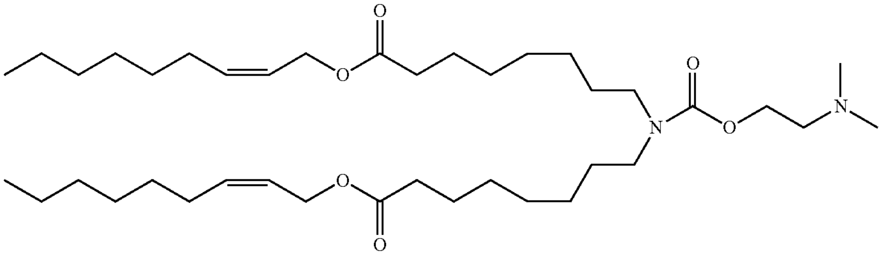
ATX-023
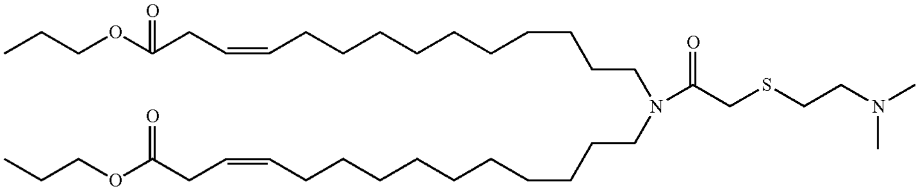
ATX-024
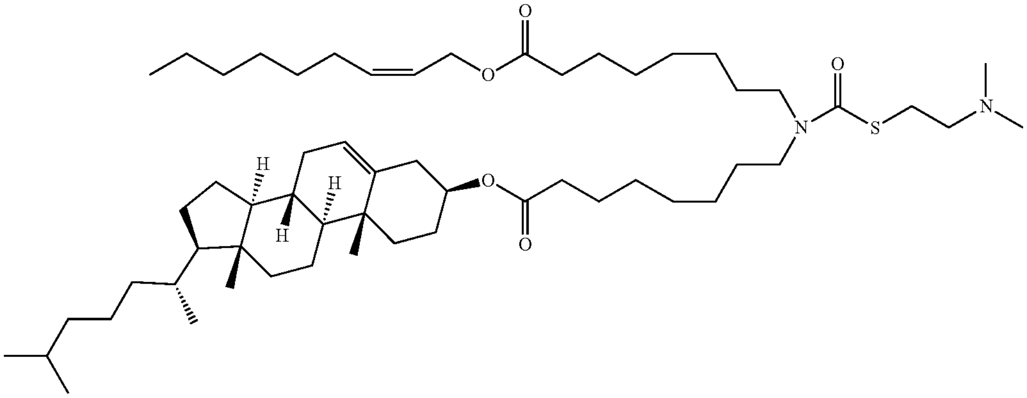
ATX-025
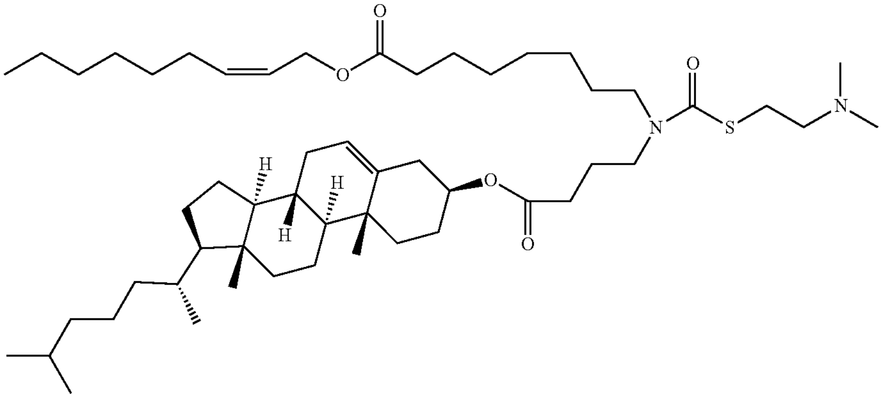
ATX-026
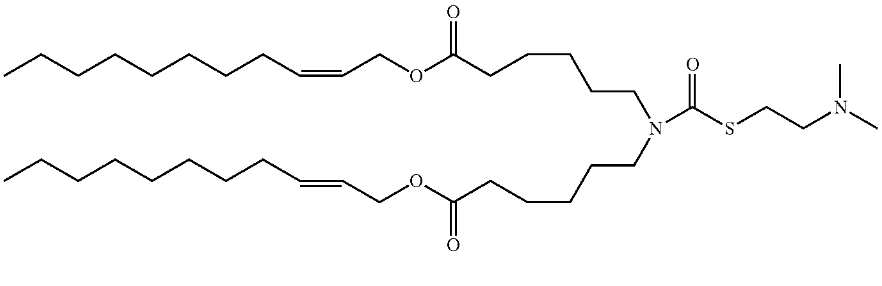

-continued
ATX-027
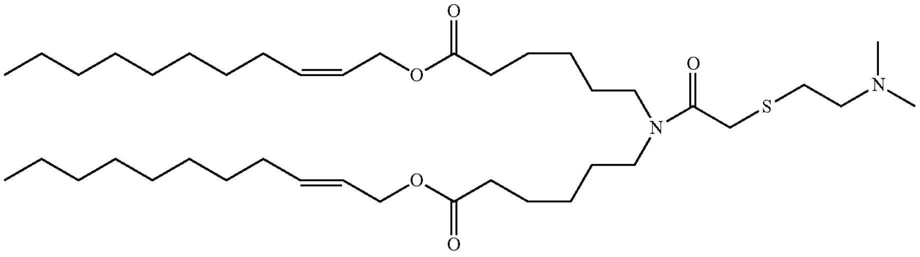
ATX-028
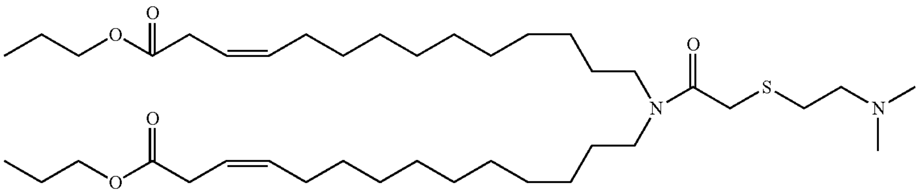
ATX-031
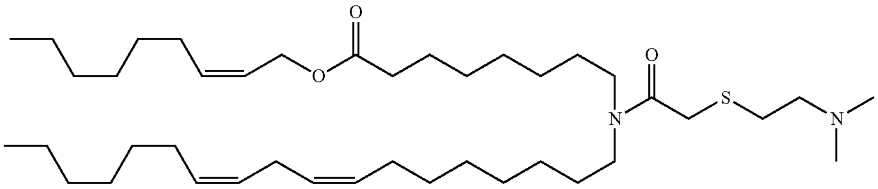
ATX-032
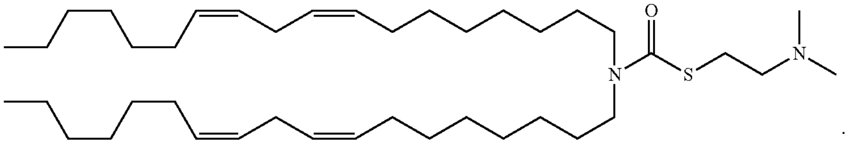
ATX-081
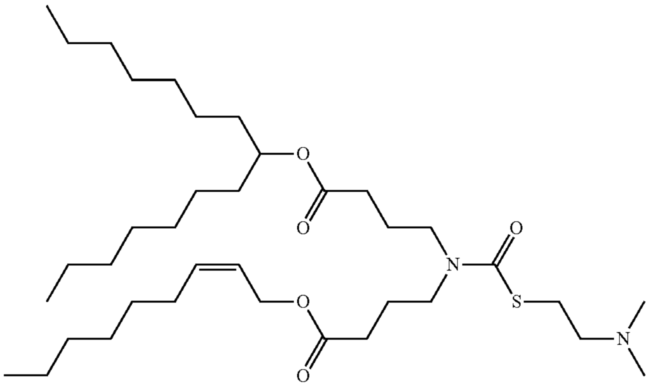

-continued

ATX-095

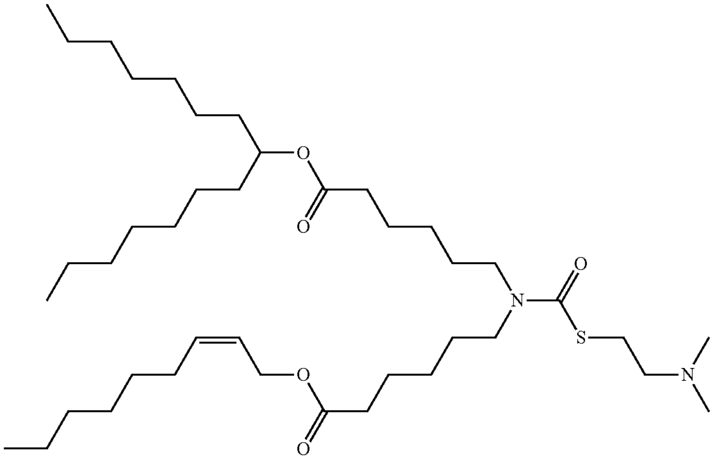

ATX-0126

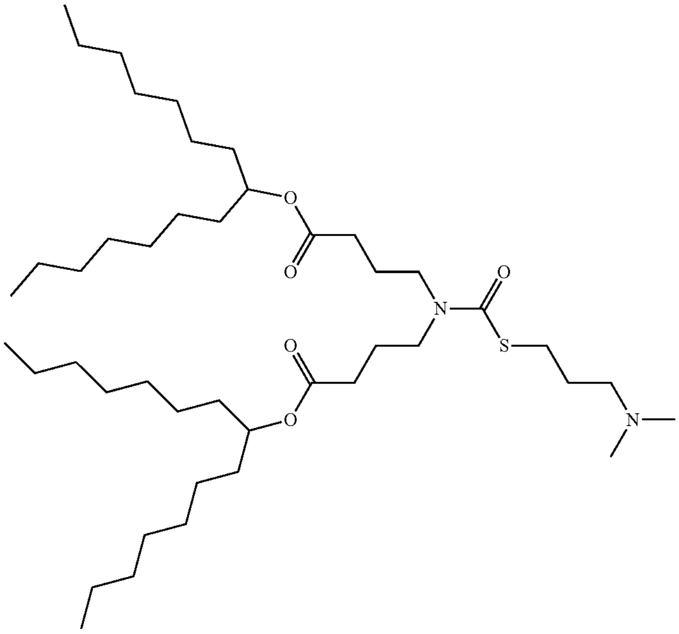

Cationic Lipids

The lipid nanoparticle preferably includes a cationic lipid suitable for forming a lipid nanoparticle. Preferably, the cationic lipid carries a net positive charge at about physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.CI), 1,2-Dilinoleoyl-3-trimethylaminopropane chloride salt (DLin-TAP.CI), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DM A), 2,2-Dilinoleyl-4-dimethylaminomethyl-[1,3]-dioxolane (DLin-K-DMA) or analogs thereof, (3 aR,5s,6aS)—N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)- heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination of any of the foregoing. Other cationic lipids include, but are not limited to, N,N-distearyl-N,N-dimethylammonium bromide (DDAB), 3P—(N—(N',N'-dimethylaminoethane)-carbamoyl)cholesterol (DC-Choi), N-(1-(2,3-dioleyloxy)propyl)-N-2-(sperminecarboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al, PNAS, 107(5), 1864-69, 2010. Other suitable amino lipids include those having alternative fatty acid groups and other dialkylamino groups, including those, in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In a further preferred embodiment, the LNP comprises the cationic lipid with formula (III) according to the patent application PCT/EP2017/064066. In this context, the disclosure of PCT/EP2017/064066 is also incorporated herein by reference.

In certain embodiments, amino or cationic lipids of the invention have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention. In certain embodiments, the protonatable lipids have a pKa of the protonatable group in the range of about 4 to about 11, e.g., a pKa of about 5 to about 7.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle). In one embodiment, the ratio of cationic lipid to nucleic acid is from about 3 to about 15, such as from about 5 to about 13 or from about 7 to about 11.

Pharmaceutical Compositions

In some aspects, this invention provides pharmaceutical compositions containing a translatable compound and a pharmaceutically acceptable carrier.

A pharmaceutical composition can be capable of local or systemic administration. In some aspects, a pharmaceutical composition can be capable of any modality of administration. In certain aspects, the administration can be by any route, including intravenous, subcutaneous, pulmonary, intramuscular, intraperitoneal, dermal, oral, inhalation or nasal administration.

Embodiments of this invention include pharmaceutical compositions containing a translatable compound in a lipid formulation.

In some embodiments, a pharmaceutical composition may comprise one or more lipids selected from cationic lipids, anionic lipids, sterols, pegylated lipids, and any combination of the foregoing. In some embodiments, the pharmaceutical composition containing a translatable compound comprises a cationic lipid, a phospholipid, cholesterol, and a pegylated lipid.

In certain embodiments, a pharmaceutical composition can be substantially free of liposomes.

In further embodiments, a pharmaceutical composition can include nanoparticles.

Some examples of lipids and lipid compositions for delivery of an active molecule of this invention are given in WO/2015/074085, which is hereby incorporated by reference in its entirety. In certain embodiments, the lipid is a cationic lipid. In some embodiment, the cationic lipid comprises a compound of formula II:

Formula II

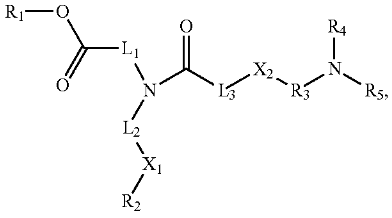

in which $R_1$ and $R_2$ are the same or different, each a linear or branched alkyl, alkenyl, or alkynyl, $L_1$ and $L_2$ are the same or different, each a linear alkyl having at least five carbon atoms, or form a heterocycle with the N, $X_1$ is a bond, or is —CO—O— whereby $L_2$-CO—O—$R_2$ is formed $X_2$ is S or O, $L_3$ is a bond or a lower alkyl, $R_3$ is a lower alkyl, $R_4$ and $R_5$ are the same or different, each a lower alkyl. What is also described herein is the compound of formula II, in which $L_3$ is absent, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is absent, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is absent, $R_1$ and $R_2$ each consists of an alkenyl of at least nine carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is methylene, $R_1$ and $R_2$ each consists of at least seven carbon atoms, $R_3$ is ethylene or n-propylene, $R_4$ and $R_5$ are methyl or ethyl, and $L_1$ and $L_2$ each consists of a linear alkyl having at least five carbon atoms. What is also described herein is the compound of formula II, in which $L_3$ is methylene, $R_1$ and $R_2$ each consists of at least nine carbon atoms, $R_3$ is ethylene or n-propylene, $R_4$ and $R_5$ are each methyl, $L_1$ and $L_2$ each consists of a linear alkyl having at least seven carbon atoms. What is also described herein is the compound of formula II, in which $L_3$ is methylene, $R_1$ consists of an alkenyl having at least nine carbon atoms and $R_2$ consists of an alkenyl having at least seven carbon atoms, $R_3$ is n-propylene, $R_4$ and $R_5$ are each methyl, $L_1$ and $L_2$ each consists of a linear alkyl having at least seven carbon atoms. What is also described herein is the compound of formula II, in which $L_3$ is methylene, $R_1$ and $R_2$ each consists of an alkenyl having at least nine carbon atoms, $R_3$ is ethylene, $R_4$ and $R_5$ are each methyl, $L_1$ and $L_2$ each consists of a linear alkyl having at least seven carbon atoms.

In exemplary embodiments, the cationic lipid comprises a compound of selected from the group consisting of ATX-001, ATX-002, ATX-003, ATX-004, ATX-005, ATX-006, ATX-007, ATX-008, ATX-009, ATX-010, ATX-011, ATX-012, ATX-013, ATX-014, ATX-015, ATX-016, ATX-017, ATX-018, ATX-019, ATX-020, ATX-021, ATX-022, ATX-023, ATX-024, ATX-025, ATX-026, ATX-027, ATX-028, ATX-029, ATX-030, ATX-031, ATX-032, ATX-081, ATX-095, and ATX-126, or a pharmaceutically acceptable salt thereof.

In certain exemplary embodiments, the cationic lipid comprises ATX-002, ATX-081, ATX-095, or ATX-126.

In some embodiments, the cationic lipid or a pharmaceutically acceptable salt thereof, may be presented in a lipid composition, comprising a nanoparticle or a bilayer of lipid molecules. The lipid bilayer preferably further comprises a neutral lipid or a polymer. The lipid composition preferably comprises a liquid medium. The composition preferably further encapsulates a translatable compound of the present invention. The lipid composition preferably further comprises a translatable compound of the present invention and a neutral lipid or a polymer. The lipid composition preferably encapsulates the translatable compound.

In further embodiments, the cationic lipid comprises a compound of formula

Formula III

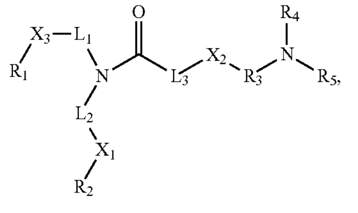

wherein $R_1$ and $R_2$ are the same or different, each a linear or branched alkyl consisting of 1 to 9 carbons, an alkenyl or alkynyl consisting of 2 to 11 carbons, or cholesteryl, $L_1$ and $L_2$ are the same or different, each a linear alkylene or alkenylene consisting of 5 to 18 carbons, $X_1$ is —CO—O— whereby $-L_2$-CO—O—$R_2$ is formed, $X_2$ is S or O, $X_3$ is —CO—O— whereby $-L_1$-CO—O—$R_1$ is formed, $L_3$ is a bond, $R_3$ is a linear or branched alkylene consisting of 1 to 6 carbons, and $R_4$ and $R_5$ are the same or different, each hydrogen or a linear or branched alkyl consisting of 1 to 6 carbons; or a pharmaceutically acceptable salt thereof. In one embodiment, $X_2$ is S. In another embodiment, $R_3$ is selected from ethylene, n-propylene, or isobutylene. In yet another embodiment, $R_4$ and $R_5$ are separately methyl, ethyl, or isopropyl. In yet another embodiment, $L_1$ and $L_2$ are the same. In yet another embodiment, $L_1$ and $L_2$ differ. In yet another embodiment, $L_1$ or $L_2$ consists of a linear alkylene having seven carbons. In yet another embodiment, $L_1$ or $L_2$ consists of a linear alkylene having nine carbons. In yet another embodiment, $R_1$ and $R_2$ are the same. In yet another embodiment, $R_1$ and $R_2$ differ. In yet another embodiment, $R_1$ and $R_2$ each consists of an alkenyl. In yet another embodiment, $R_1$ and $R_2$ each consists of an alkyl. In yet another embodiment, the alkenyl consists of a single double bond. In yet another embodiment, $R_1$ or $R_2$ consists of nine carbons. In yet another embodiment, $R_1$ or $R_2$ consists of eleven carbons. In yet another embodiment, $R_1$ or $R_2$ consists of seven carbons. In yet another embodiment, $L_3$ is a bond, $R_3$ is ethylene, $X_2$ is S, and $R_4$ and $R_5$ are each methyl. In yet another embodiment, $L_3$ is a bond, $R_3$ is n-propylene, $X_2$ is S, $R_4$ and $R_5$ are each methyl. In yet another embodiment, $L_3$ is a bond, $R_3$ is ethylene, $X_2$ is S, and $R_4$ and $R_5$ are each ethyl.

As would be appreciated by the skilled artisan, the compounds of formulas II and III form salts that are also within the scope of this disclosure. Reference to a compound of formulas II and III herein is understood to include reference to salts thereof, unless otherwise indicated. The term "salt (s)", as employed herein, denotes acidic salts formed with inorganic and/or organic acids, as well as basic salts formed with inorganic and/or organic bases. In addition, when a compound of formula II or III contains both a basic moiety, such as, but not limited to, a pyridine or imidazole, and an acidic moiety, such as, but not limited to, a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of the formula II or III may be formed, for example, by reacting a compound of formula II or III with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, J. Pharmaceutical Sciences (1977) 66(1)1-19; P. Gould, International J. Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like. Basic nitrogen-containing groups may be quarternized with agents such as lower alkyl halides (e.g., methyl, ethyl, propyl, and butyl chlorides, bromides, and iodides), dialkyl sulfates (e g, dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure. Compounds of formula II or III can exist in unsolvated and solvated forms, including hydrated forms. In general, the solvated forms, with pharmaceutically acceptable solvents such as water, ethanol, and the like, are equivalent to the unsolvated forms for the purposes of this disclosure. Compounds of formula II or III and salts, solvates thereof, may exist in their tautomeric form (for example, as an amide or imino ether). All such tautomeric forms are contemplated herein as part of the present disclosure.

The cationic lipid compounds described herein may be combined with a translatable compound of the invention to form microparticles, nanoparticles, liposomes, or micelles. The translatable compound of the invention to be delivered by the particles, liposomes, or micelles may be in the form of a gas, liquid, or solid. The cationic lipid compound and the translatable compound may be combined with other cationic lipid compounds, polymers (synthetic or natural), surfactants, cholesterol, carbohydrates, proteins, lipids, etc. to form the particles. These particles may then optionally be combined with a pharmaceutical excipient to form a pharmaceutical composition.

In certain embodiments, the cationic lipid compounds are relatively non-cytotoxic. The cationic lipid compounds may be biocompatible and biodegradable. The cationic lipid may have a pKa in the range of approximately 5.5 to approximately 7.5, more preferably between approximately 6.0 and approximately 7.0. It may be designed to have a desired pKa between approximately 3.0 and approximately 9.0, or between approximately 5.0 and approximately 8.0.

A composition containing a cationic lipid compound may be 30-70% cationic lipid compound, 0-60% cholesterol, 0-30% phospholipid and 1-10% polyethylene glycol (PEG). Preferably, the composition is 30-40% cationic lipid compound, 40-50% cholesterol, and 10-20% PEG. In other preferred embodiments, the composition is 50-75% cationic lipid compound, 20-40% cholesterol, and 5 to 10% phospholipid, and 1-10% PEG. The composition may contain 60-70% cationic lipid compound, 25-35% cholesterol, and 5-10% PEG. The composition may contain up to 90% cationic lipid compound and 2 to 15% helper lipid. The formulation may be a lipid particle formulation, for example containing 8-30% compound, 5-30% helper lipid, and 0-20% cholesterol; 4-25% cationic lipid, 4-25% helper lipid, 2 to 25% cholesterol, 10 to 35% cholesterol-PEG, and 5% cholesterol-amine; or 2-30% cationic lipid, 2-30% helper lipid, 1 to 15% cholesterol, 2 to 35% cholesterol-PEG, and 1-20% cholesterol-amine; or up to 90% cationic lipid and 2-10% helper lipids, or even 100% cationic lipid.

In some embodiments, the one or more cholesterol-based lipids are selected from cholesterol, PEGylated cholesterol and DC-Chol (N,N-dimethyl-N-ethylcarboxamidocholesterol), and 1,4-bis(3-N-oleylamino-propyl)piperazine. In an exemplary embodiment, the cholesterol-based lipid is cholesterol.

In some embodiments, the one or more pegylated lipids, i.e., PEG-modified lipids. In some embodiments, the one or more PEG-modified lipids comprise a poly(ethylene) glycol chain of up to 5 kDa in length covalently attached to a lipid with alkyl chain(s) of $C_6$-$C_{20}$ length. In some embodiments, a PEG-modified lipid is a derivatized ceramide such as N-Octanoyl-Sphingosine-1-[Succinyl(Methoxy Polyethylene Glycol)-2000]. In some embodiments, a PEG-modified or PEGylated lipid is PEGylated cholesterol or Dimyristoylglycerol (DMG)-PEG-2K. In an exemplary embodiment, the PEG-modified lipid is PEGylated cholesterol.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions and methods are described, for example, in Remington's Pharmaceutical Sciences, Mack Publishing Co. (A. R. Gennaro ed. 1985), and Remington, The Science and Practice of Pharmacy, 21st Edition (2005).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause translation of a translatable molecule in a cell.

A therapeutically effective dose can be an amount of an agent or formulation that is sufficient to cause a therapeutic effect. A therapeutically effective dose can be administered in one or more separate administrations, and by different routes. As will be appreciated in the art, a therapeutically effective dose or a therapeutically effective amount is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating phenylketonuria). For example, a therapeutically effective amount may be an amount sufficient to achieve a desired therapeutic and/or prophylactic effect. Generally, the amount of a therapeutic agent (e.g., a translatable oligomer encoding PAH) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

Methods provided herein contemplate single as well as multiple administrations of a therapeutically effective amount of the translatable compound (e.g., a translatable oligomer encoding PAH) described herein. Pharmaceutical compositions comprising a translatable compound encoding PAH can be administered at regular intervals, depending on the nature, severity and extent of the subject's condition (e.g., the severity of a subject's phenylketonuria and the associated symptoms of PKU, the subject's phenylalanine levels, and/or the subject's PAH levels). In some embodiments, a therapeutically effective amount of the translatable compound (e.g., a translatable oligomer encoding PAH) of the present invention may be administered periodically at regular intervals (e.g., once every year, once every six months, once every four months, once every three months, once every two months, once a month), biweekly, weekly, daily, twice a day, three times a day, four times a day, five times a day, six times a day, or continuously.

In some embodiments, the pharmaceutical compositions of the present invention are formulated such that they are suitable for extended-release of the translatable compound encoding PAH contained therein. Such extended-release compositions may be conveniently administered to a subject at extended dosing intervals. For instance, in one embodiment, the pharmaceutical compositions of the present invention are administered to a subject twice a day, daily or every other day. In some embodiments, the pharmaceutical compositions of the present invention are administered to a subject twice a week, once a week, every 10 days, every two weeks, every 28 days, every month, every six weeks, every eight weeks, every other month, every three months, every four months, every six months, every nine months or once a year. Also contemplated herein are pharmaceutical compositions which are formulated for depot administration (e.g., subcutaneously, intramuscularly) to either deliver or release a translatable compound encoding PAH over extended periods of time. Preferably, the extended-release means employed are combined with modifications made to the translatable compound encoding PAH to enhance stability.

A therapeutically effective dose, upon administration, can result in serum or plasma levels of PAH of 1-1000 pg/ml, or 1-1000 ng/ml, or 1-1000 μg/ml, or more. In some embodiments, administering a therapeutically effective dose of a composition comprising a translatable molecule of the invention can result in increased liver PAH protein levels in a treated subject. In some embodiments, administering a composition comprising a translatable molecule of the invention results in a 5%, 10%, 20%, 30%, 40%, 50%, 60%, 70%, 80%, 90%, or 95% increase in liver PAH protein levels relative to a baseline PAH protein level in the subject prior to treatment. In certain embodiments, administering a therapeutically effective dose of a composition comprising a translatable molecule of the invention will result an increase in liver PAH levels relative to baseline liver PAH levels in the subject prior to treatment. In some embodiments, the increase in liver PAH levels relative to baseline liver PAH levels will be at least 5%, 10%, 20%, 30%, 40%, 50%, 100%, 200%, or more.

In some embodiments, a therapeutically effective dose, when administered regularly, results in increased expression of PAH in the liver as compared to baseline levels prior to treatment. In some embodiments, administering a therapeutically effective dose of a composition comprising a translatable molecule of the invention results in the expression of a PAH protein level at or above about 10 ng/mg, about 20 ng/mg, about 50 ng/mg, about 100 ng/mg, about 150 ng/mg, about 200 ng/mg, about 250 ng/mg, about 300 ng/mg, about 350 ng/mg, about 400 ng/mg, about 450 ng/mg, about 500 ng/mg, about 600 ng/mg, about 700 ng/mg, about 800 ng/mg, about 900 ng/mg, about 1000 ng/mg, about 1200 ng/mg or about 1500 ng/mg of the total protein in the liver of a treated subject.

In some embodiments, a therapeutically effective dose, when administered regularly, results in a reduction of phenylalanine levels in a biological sample. In some embodiments, administering a therapeutically effective dose of a composition comprising a translatable molecule of this invention results in a reduction of phenylalanine levels in a biological sample (e.g., a plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline phenylalanine levels before treatment. In some embodiments, the biological sample is selected from plasma, serum, whole blood, urine, or cerebrospinal fluid. In some embodiments, administering a therapeutically effective dose of a composition comprising a translatable molecule of this invention results in reduction of phenylalanine levels to about 1000 μmol/L or less, about 900 μmol/L or less, about 800 μmol/L or less, about μmol/L or less, about 600 μmol/L or less, about 500 μmol/L or less, about 400 μmol/L or less, about 300 μmol/L or less, about 200 μmol/L or less, about 100 μmol/L or less or about 50 μmol/L or less in serum or plasma. In an exemplary embodiment, a therapeutically effective dose, when administered regularly results in reduction of phenylalanine levels to about 600 μmol/L or less in serum or plasma. In another exemplary embodiment, a therapeutically effective dose, when administered regularly results in reduction of phenylalanine levels to about 360 μmol/L or less in serum or plasma. In another exemplary embodiment, a therapeutically effective dose, when administered regularly results in reduction of phenylalanine levels to about 120 μmol/L or less in serum or plasma.

In some embodiments, administering a therapeutically effective dose of a composition comprising a translatable oligomer encoding PAH will result in reduced urine levels of phenylalanine and/or metabolites of phenylalanine such as phenylketone and/or phenylpyruvate.

A therapeutically effective dose of an active agent (e.g., a translatable oligomer encoding PAH) in vivo can be a dose of about 0.001 to about 500 mg/kg body weight. For instance, the therapeutically effective dose may be about 0.001-0.01 mg/kg body weight, or 0.01-0.1 mg/kg, or 0.1-1 mg/kg, or 1-10 mg/kg, or 10-100 mg/kg. In some embodiments, a translatable oligomer encoding PAH is provided at a dose ranging from about 0.1 to about 10 mg/kg body weight, e.g., from about 0.5 to about 5 mg/kg, from about 1 to about 4.5 mg/kg, or from about 2 to about 4 mg/kg.

A therapeutically effective dose of an active agent (e.g., a translatable oligomer encoding PAH) in vivo can be a dose of at least about 0.001 mg/kg body weight, or at least about 0.01 mg/kg, or at least about 0.1 mg/kg, or at least about 1 mg/kg, or at least about 2 mg/kg, or at least about 3 mg/kg, or at least about 4 mg/kg, or at least about 5 mg/kg, at least about 10 mg/kg, at least about 20 mg/kg, at least about 50 mg/kg, or more. In some embodiments, a translatable oligomer encoding PAH is provided at a dose of about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 5 mg/kg, or about 6, 7, 8, 9, 10, 15, 20, 25, 50, 75, or 100 mg/kg.

Nucleobase sequences shown herein are from left to right, 5' to 3', unless stated otherwise.

Transfections

In some experiments, translatable messenger molecules were transfected into Hepa1-6 or AML12 cells in 96 well plates. The MessengerMAX transfection reagent (Thermo Fisher Scientific) was used by manufacture instruction for all transfections. Other suitable cell lines include HEK293 and Hep3B cells.

An example transfection protocol in vitro was as follows:

Plate hepatocyte Hepa1-6 cells 5000 cells per well in 96 well plate at least 8 hours before transfection.

Replace 90 μL DMEM medium containing 10% FBS and Non-essential amino acid adding 90 μL into each well of 96 well plate immediately before beginning the transfection experiment.

Prepare MessengerMAX transfection reagent (Thermo Fisher Scientific) translatable molecule complex according to manufacturer's instruction.

Transfer 10 μL of the complex into a well containing the cells in the 96-well plate.

Collect the medium after desired time points and add 100 μL fresh medium into each well. Medium will be kept at −80° C. until an ELISA assay for PAH is performed using the standard manufacturer protocol.

An example of a transfection protocol in vivo was as follows:

The translatable molecule is formulated with nanoparticles.

Inject the nanoparticle-formulated translatable molecule (1 mg/kg) into BL57BL/c mice (4-6 week-old) via standard i.v. injection in the lateral tail vein.

Collect approximately 50 μL of blood in a Heparin-coated microcentrifuge tube at a suitable time post-injection.

Centrifuge at 3,000×g for 10 minutes at 4° C.

Transfer the supernatant (plasma) into a fresh microcentrifuge tube. Plasma will be kept at −80° C. until an ELISA assay for PAH is performed using the standard manufacturer protocol.

Nanoparticle Formulations

Lipid nanoparticles can be prepared containing an mRNA, using appropriate volumes of lipids in an ethanol/aqueous buffer containing the mRNA. A Nanossemblr microfluidic device can be used for this purpose, followed by downstream processing. For example, to prepare nanoparticles, a desired amount of targeted mRNA can be dissolved into 5 mM Citric Acid buffer (pH 3.5). The lipids can be dissolved at the adequate molar ratio, in ethanol. The molar percentage ratio for the constituent lipids can be, for example, 50% ionizable lipid, 7% DSPC (1,2-distearoyl-sn-glycero-3-phosphocholine; Avanti Polar Lipids), 40% cholesterol (Avanti Polar Lipids), and 3% DMG-PEG (1,2-Dimyristoyl-sn-glycerol, methoxypolyethylene glycol, PEG chain molecular weight: 2000; NOF America Corporation). Next, the lipid and mRNA solutions can be combined in the microfluidic device (Precision NanoSystems) at a flow ratio of 1:3 (ethanol:aqueous phase). The total combined flow rate can be 12 mL/min. Lipid nanoparticles can be formed and subsequently purified by overnight dialysis using a phosphate buffer in a dialysis device (Float-a-lyzer, Spectrum Labs), followed by concentration using Amicon Ultra-15 centrifugal filters (Merck Millipore). The particle size can be determined by dynamic light scattering (ZEN3600, Malvern Instruments). An "encapsulation" efficiency can be calculated by determining the un-encapsulated mRNA content measured by the fluorescence upon the addition of RiboGreen (Molecular Probes) to the LNP slurry (Fi); then, the value was compared to the total mRNA content that is obtained upon lysis of the LNPs by 1% Triton X-100 (Ft), where percentage of "encapsulation"=(Ft−Fi)/Ft×100. Encapsulation can refer to inclusion of the mRNA in the nanoparticle, regardless of form.

In-Cell Western 96-well collagen plates were used to seed the cells at the appropriate density in DMEM/FBS culture media. At the optimal confluence, cells were transfected with the targeted mRNAs diluted in the transfection reagent mix (MessengerMax and Opti-MEM). Cells were placed in the CO2 incubator and let them grow. At the desire timepoint, media was removed and cells were fixed in 4% fresh PFA for 20 min. After that, fixative was removed and cells were permeabilized in TBST for 5 minutes several times. When permeabilization washes are complete, cells were incubated with the blocking buffer for 45 min. Primary antibody was then added and incubated for 1 h at room temperature. Following that, cells were washed several times in TBST, and then incubated for 1 h with the secondary antibody diluted in blocking buffer and containing the CellTag 700 stain. To finalize, cells were washed several times in TBST followed by a last wash in TBS. Then, plate was imaged using the Licor detection system and data was normalized to the total number of cells labeled by the CellTag 700.

Generating Tail PCR Products

Plasmid DNA (10 ng) containing each mRNA expression construct can be used to generate the poly A tail 120 PCR products in a 50 μl PCR reaction with 2×KAPA HiFi PCR mix (KR0370) as per the manufacturer's instructions. The product can be then checked on a 2% gel from Thermo Fisher Scientific and approximately quantified based on the intensity of the low molecular weight ladder (Thermo Fisher Scientific, 10068-013), and cleaned with the Qiagen PCR purification kit and resuspended in 50 ul water.

In Vitro Transcription (IVT) for Synthesis

The following protocol is for a 200 μl IVT reaction using NEB HiScribe T7 RNA polymerase reagents, which should yield about 1 mg of RNA. 2.5×NTP mix was prepared as required by thawing individual 100 mM NTP stocks (ATP, GTP, CTP, and UTP nucleotides, or chemically modified counterparts) and pooling them together. For the IVT reaction, about 2-4 μg of the template was used for a 200 μl reaction. The 10×IVT reaction buffer, the 2.5×dNTP mix, the template DNA and the T7 RNA polymerase are mixed well by pipetting and incubated at 37° C. for 4 hours. To degrade the DNA template, the IVT reaction is diluted with 700 ul of nuclease-free water and then 10×DNase I buffer and 20 ul of the RNase-free DNase I are added to the IVT mix and incubated at 37° C. for 15 minutes. The diluted (to 1 ml) and DNase treated reaction is then purified by a Qiagen RNeasy Maxi columns as per the manufacturer's instructions with a final elution in RNase-free water. The purified RNA is then quantified by UV absorbance where the A260/A280 should be about 1.8-2.2, depending on the resuspension buffer used.

Enzymatic Capping of IVT RNA

For enzymatic capping, a 50× scaled-up version of NEB's one-step capping and 2'O-methylation reaction can be used, that is suitable for treating up to 1 mg of IVT transcripts. A 10 μg RNA in a 20 μl reaction is recommended, based on the assumption that transcript length would be as short as 100 nt. However, a higher substrate-to-reaction volume is acceptable for transcripts, which can be generally longer (about 300-600 nt) in length. Before initiating the capping reaction, the RNA is denatured at 65° C. for 5 minutes and then snap chilled to relieve any secondary conformations. For the total 1 ml capping reaction, 1 mg denatured RNA in 700 μl of nuclease-free water is used along with 100 μl (10×) capping buffer, 50 μl (10 mM) GTP, 50 μl (4 mM) SAM, 50 μl of (10 U/μl) Vaccinia capping enzyme and 50 μl of mRNA cap 2'-O-methyltransferase at (50 U/μl) are combined and incubated at 37° C. for 1 hour. The resulting capped mRNA is eluted using RNase free water, re-purified on an RNeasy column, quantified by nanodrop. The mRNA is also visualized on the gel by running 500 ng of the purified product per lane in a denaturing gel after denaturation and snap-chill to remove secondary structures.

EXAMPLES

All translatable molecules shown in the examples below, including the reference molecule 509, were synthesized with $N^1$-methylpseudouridine in place of uridine.

Example 1: Reference Translatable Molecule 509

In this example, a reference translatable molecule 509 was made and used for expressing human WT phenylalanine hydroxylase (PAH). The translatable molecule comprised a 5' cap (7mGpppG), a 5' UTR of TEV, a Kozak sequence, a WT PAH CDS, a 3'UTR of *Xenopus* beta-globin, and a Poly(A) tail region consisting of 100 As (i.e., "Poly(A) 100 tail region"). The reference translatable molecule further comprised the sequence of SEQ ID NO: 44 immediately downstream of the PAH CDS.

Details of the structure of this reference translatable molecule are as follows: Tobacco Etch Virus (TEV) 5' UTR of SEQ ID NO: 3, a Kozak Sequence of SEQ ID NO: 4, a WT PAH CDS mRNA sequence of SEQ ID NO: 5, a *Xenopus* beta-globin (XBG) 3' UTR of SEQ ID NO: 6, and a Poly(A) 100 Tail of SEQ ID NO: 7.

Translatable molecules in the examples below can be synthesized with the 5' cap being a m7GpppGm cap. The translatable molecules in the examples below can contain a 5'-UTR (e.g., a 5' UTR of TEV (SEQ ID NO: 3)), a translation initiation sequence (e.g., a Kozak sequence of SEQ ID NO: 4), a sequence of SEQ ID NO: 44, a 3' UTR (e.g., a 3' UTR of *Xenopus* beta-globin (SEQ ID NO: 6)), and a poly(A) tail (e.g., a polyA 100 tail region of SEQ ID NO: 7 or a polyA 114 tail region of SEQ ID NO: 43).

Example 2: Translatable Molecules Encoding PAH

In this example, a translatable molecules 510-521, 690-692, 694-707, 1778, 1971, and 1986 were made and used for expressing human phenylalanine hydroxylase (PAH) with advantageously increased efficiency of translation. The translatable molecules expressing human phenylalanine hydroxylase (PAH) exhibited activity suitable for use in methods for ameliorating or treating PKU. The translatable molecules comprised a 5' cap (m7GpppGm), a 5' UTR of TEV, a Kozak sequence, a PAH CDS, and a 3' UTR of *Xenopus* beta-globin. Translatable molecules 510-511, 513-519, 690-692, and 695 further comprise a Poly(A) 100 tail region, while translatable molecules 512, 520-521, 694, 696-707, 1778, 1971, and 1986 further comprise a Poly(A) 114 tail region. The translatable molecules further comprised the sequence of SEQ ID NO: 44 immediately downstream of the PAH CDS.

The PAH CDS in each of the translatable molecules is comprised of the following sequences:

| Molecule | PAH CDS |
|---|---|
| 510 | SEQ ID NO: 8 |
| 511 | SEQ ID NO: 9 |
| 512 | SEQ ID NO: 10 |
| 513 | SEQ ID NO: 11 |
| 514 | SEQ ID NO: 12 |
| 515 | SEQ ID NO: 13 |
| 516 | SEQ ID NO: 14 |
| 517 | SEQ ID NO: 15 |
| 518 | SEQ ID NO: 16 |
| 519 | SEQ ID NO: 17 |
| 520 | SEQ ID NO: 18 |
| 521 | SEQ ID NO: 19 |
| 690 | SEQ ID NO: 20 |
| 691 | SEQ ID NO: 21 |
| 692 | SEQ ID NO: 22 |
| 694 | SEQ ID NO: 23 |
| 695 | SEQ ID NO: 24 |
| 696 | SEQ ID NO: 25 |
| 697 | SEQ ID NO: 26 |
| 698 | SEQ ID NO: 27 |
| 699 | SEQ ID NO: 28 |
| 700 | SEQ ID NO: 29 |
| 701 | SEQ ID NO: 30 |
| 702 | SEQ ID NO: 31 |
| 703 | SEQ ID NO: 32 |
| 704 | SEQ ID NO: 33 |
| 705 | SEQ ID NO: 34 |
| 706 | SEQ ID NO: 35 |
| 707 | SEQ ID NO: 36 |
| 1778 | SEQ ID NO: 37 |
| 1971 | SEQ ID NO: 45 |
| 1986 | SEQ ID NO: 46 |

The translatable molecules 510-521, 690-692, and 694-707 were translated in C57BL/c mouse to produce human PAH.

The translation efficiency of translatable molecules 511, 515, 521-522, 691-692, and 694-707 was advantageously and surprisingly increased by nearly two-fold over reference human wild type PAH.

Meanwhile, the translation efficiency of translatable molecule 513 was advantageously and surprisingly increased by 5.5-fold over reference human wild type PAH. Specifically, FIG. 1 shows the results of expressing human phenylalanine hydroxylase (PAH) in vivo using this translatable molecule. FIG. 1 shows the relative expression of PAH in WT mice for translatable molecule 513 at 8 hrs. The translatable molecule 513 was synthesized and purified with TEV 5' UTR and XBG 3' UTR, and capped during transcription and synthesized with $N^1$-methylpseudouridine, so that 100% of uridines were replaced with $N^1$-methylpseudouridine. The translatable molecule 513 was prepared in a liposomal formulation and intravenously injected into WT mice at 3 and 10 mg/kg. Mice livers were harvested, and PAH expression showed that translatable molecule 513 had increased translation efficiency.

Figure 2:
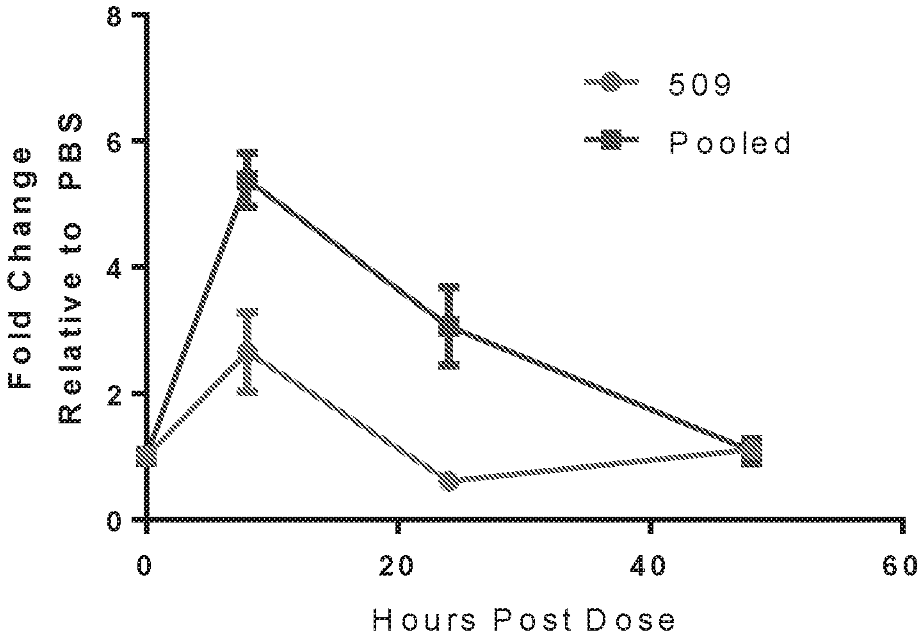
FIG. 2 shows the results of expressing human phenylalanine hydroxylase (PAH) in vivo using a translatable molecule of this invention.

FIG. 2 shows the results of expressing human phenylalanine hydroxylase (PAH) in vivo using a translatable molecule of this invention. FIG. 2 shows the relative liver expression of PAH in WT mice post-dose of pooled translatable molecules 513, 514, 517 and 520, as compared to a human WT reference mRNA. The synthesized translatable molecules 513, 514, 517 and 520 encode PAH were each prepared in a liposomal formulation and intravenously injected into WT mice.

Figure 3:
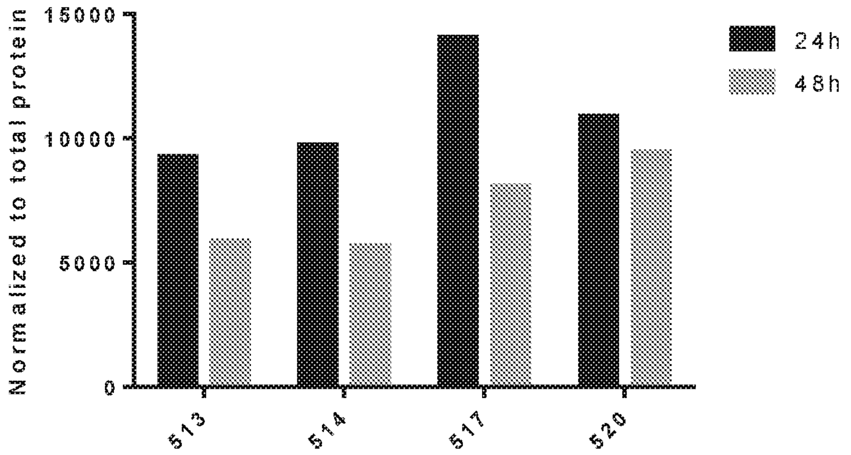
FIG. 3 shows the results of expressing human phenylalanine hydroxylase (PAH) in human primary hepatocytes using an expressible molecule of this invention.

With respect to translatable molecule 514, the translation efficiency of this translatable molecule was advantageously and surprisingly increased by nearly six-fold over reference human wild type PAH. Specifically, FIG. 3 shows the results of expressing human phenylalanine hydroxylase (PAH) in human primary hepatocytes using an expressible molecule of this invention. FIG. 3 shows expression results for molecules 513, 514, 517, and 520 after transfection with 0.6 μg of the mRNA in human primary hepatocytes. Cell lysates were harvested at 24 h and 48 h. Quantitative Western Blot was performed to detect PAH by using an antibody specific for PAH.

Figure 4:
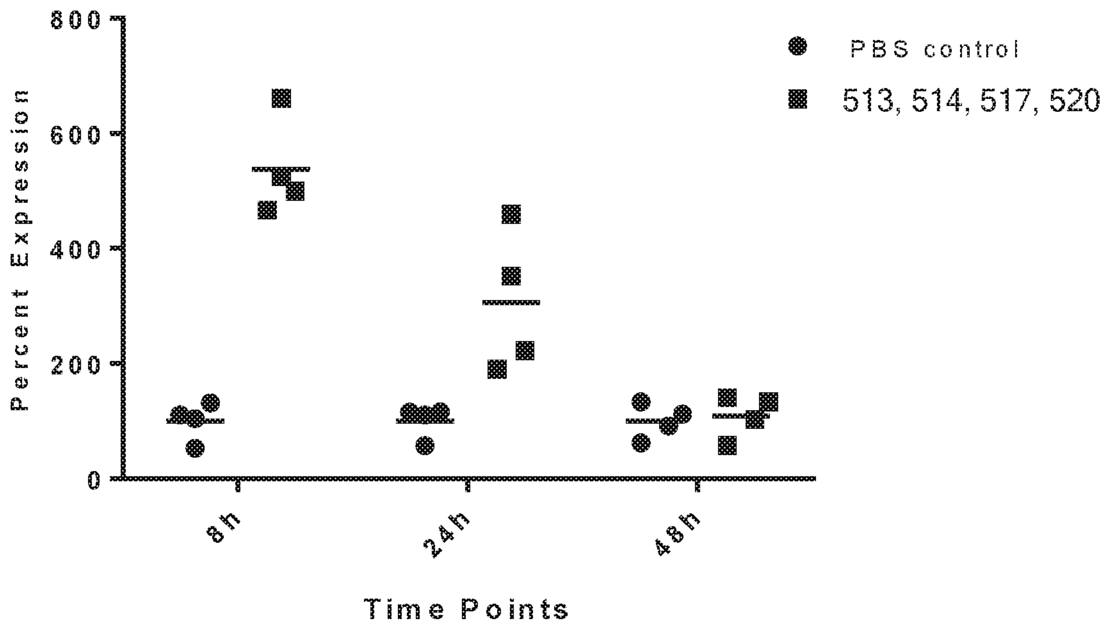
FIG. 4 shows the results of expressing human phenylalanine hydroxylase (PAH) in human primary hepatocytes using pooled expressible molecules of this invention.

With respect to translatable molecule 517, the translation efficiency of this translatable molecule was advantageously and surprisingly increased by over three-fold as compared to reference human wild type PAH. FIG. 4 shows the results of expressing human phenylalanine hydroxylase (PAH) in human primary hepatocytes using pooled expressible molecules of this invention. FIG. 4 shows expression results for pooled molecules 513, 514, 517, and 520 co-formulated and injected via IP in WT mice. The dose injected was 10 mpk, and livers were collected at different timepoints (8 h, 24 h, 48 h) for analysis. Quantitative Western Blot was performed to detect PAH by using an antibody specific for PAH. The co-formulated variants yielded high expression versus PBS control.

With respect to translatable molecule 518, the translation efficiency of this translatable molecule was advantageously and surprisingly increased by nearly three-fold over reference human wild type PAH.

With respect to translatable molecule 520, the translation efficiency of this translatable molecule was advantageously and surprisingly increased by nearly four-fold over reference human wild type PAH.

Figure 5:
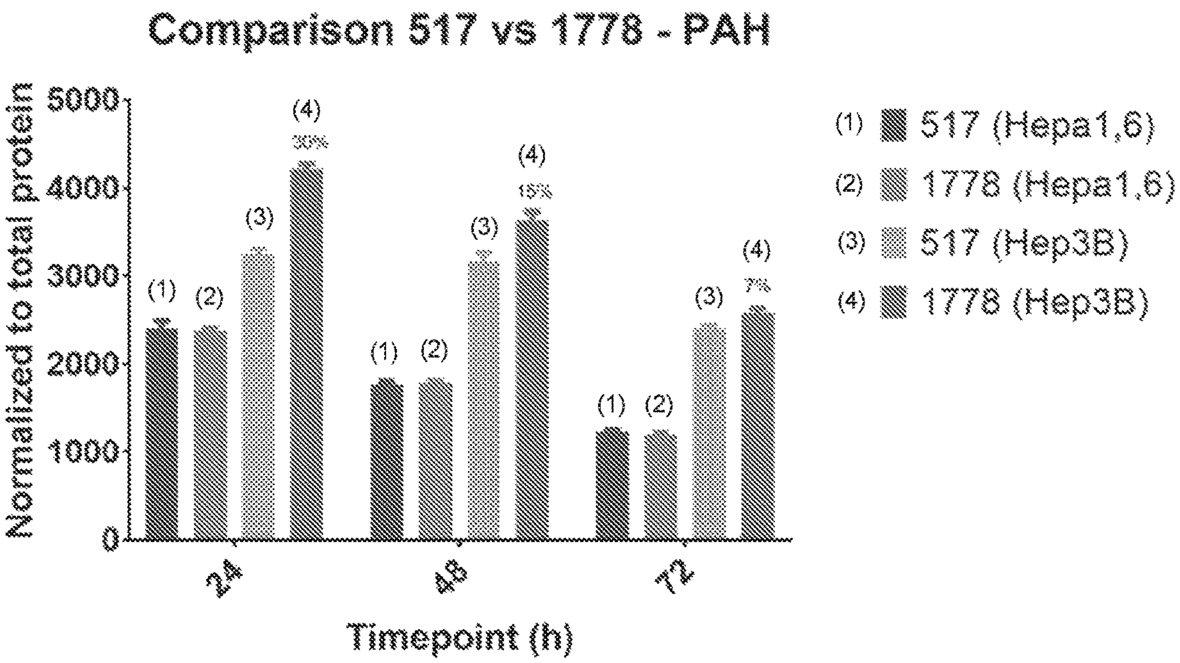
FIG. 5 shows the result of expressing human phenylalanine hydroxylase (PAH) from translatable molecules 517 and 1778 in mouse liver cells (Hepa1-6) and human liver cells (Hep3B) at 24 h, 48 h, and 72 h.

Translatable molecule 1778 was translated in Hepa1-6 (mouse liver) cells and Hep3B (human liver) cells. Expression was compared to translatable molecule 517 described above. As shown in FIG. 5, expression of translatable molecule 1778 was 30% higher in human liver cells at 24 h compared to translatable molecule 517.

Translatable molecules 1971 and 1986 were translated in human primary hepatocytes.

Example 3: Translation Enhancer Based on *Xenopus* Beta-Globin 3'UTR

In this example, the structures of 3' UTR sequences for use in enhancing translational efficiency of a translatable molecule are shown.

The base sequences shown in SEQ ID NOs: 38-42 are the portion of the translatable molecule that may correspond in functionality to the 3'-UTR of *Xenopus* beta-globin. The complete translatable molecule comprises a 5' cap (m7GpppGm), 5'-UTR, and coding region (CDS) upstream of the sequence below, and a polyA tail downstream of the sequence below, each of which corresponds to the structure of a native human mRNA. As shown above, a Kozak sequence may optionally be used. Thus, a translatable molecule incorporating the fragment below can have enhanced translational efficiency. The *Xenopus* beta-globin gene sequence is shown in accession no. NM_001096347.1

Example 4: PAH Expression in Human Primary Hepatocytes

Figure 6:
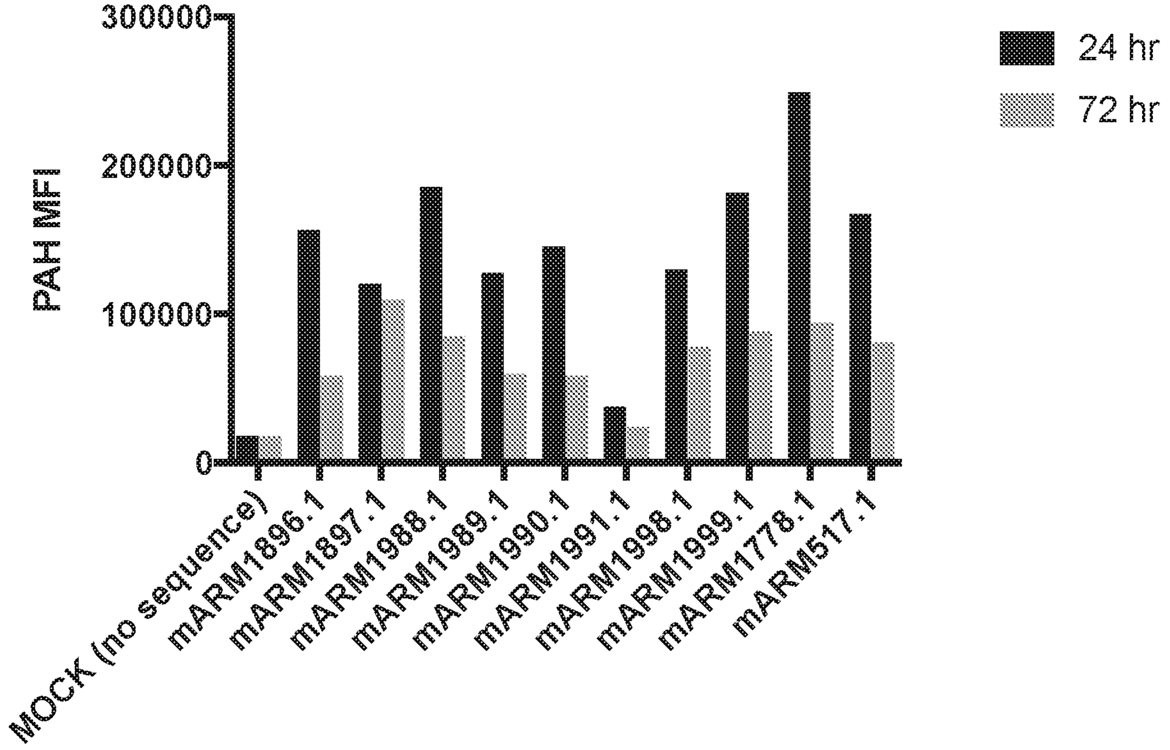
FIG. 6 shows the result of expressing human phenylalanine hydroxylase (PAH) from ten translatable molecules. Human primary hepatocytes were transfected with codon-optimized mRNA and PAH protein expression was measured by flow cytometry at 24 and 72 hours post-transfection. The translatable molecules shown in the graph as 1778.1, and 517.1 are the same as 1778, and 517, respectively, as described in Example 2. Translatable molecules 1896.1, 1897.1, 1988.1, 1989.1, 1990.1, 1991.1, 1998.1, and 1999.1 are identical to translatable molecule 1778 with the exception of alternative 3' UTR structures.

In this example, human primary hepatocytes were transfected with codon-optimized mRNA. PAH protein expression was measured by flow cytometry at 24 and 72 hours post-transfection. The expression of ten codon-optimized mRNA sequences is shown in FIG. 6. Translatable molecules 1896.1, 1897.1, 1988.1, 1989.1, 1990.1, 1991.1, 1998.1, and 1999.1 illustrated in FIG. 6 are identical to translatable molecule 1778 with the exception of alternative 3' UTR structures.

Example 5: In Vivo Analysis of Protein Expression in PKU Mouse Model

Figure 7:
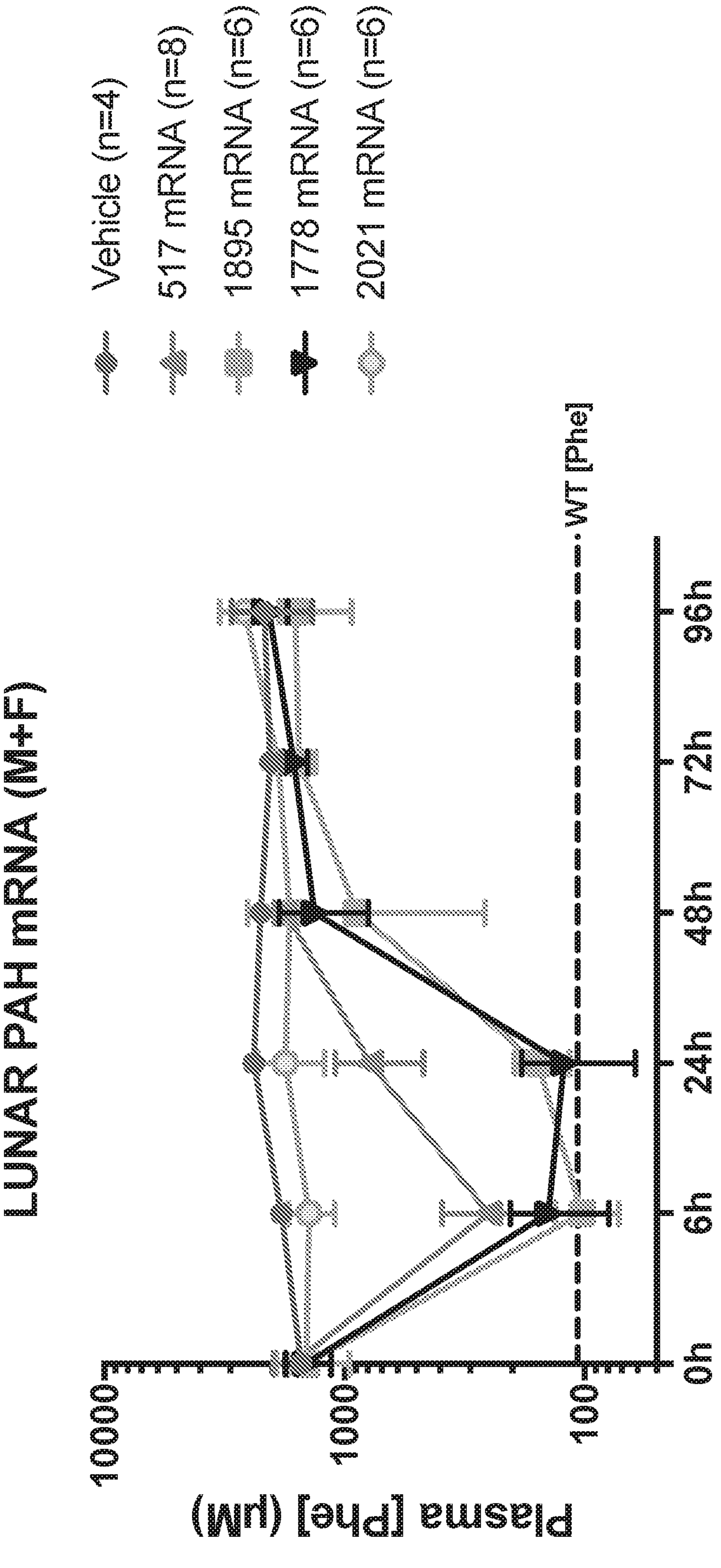
FIG. 7 shows plasma concentrations of phenylalanine in a mouse model of PKU following injection with a single dose of 10 mg/kg ATX2-formulated mRNA. Plasma concentrations of phenylalanine were measured by mass spectrometry at 6, 24, 48, 72, and 96 hours post-injection. Translatable molecule 1895 is identical to translatable molecule 1778 with the exception of an alternative 3' UTR structure.

In this example, $PAH^{enu2}$ mice were injected with a single dose of ATX2-formulated mRNA at 10 mg/kg. Plasma concentrations of phenylalanine were measured by mass spectrometry at 6, 24, 48, 72, and 96 hours post-injection. As shown in FIG. 7, significant reductions in phenylalanine levels were seen at 24 hours post-injection in mice injected with translatable molecules 517, 1778, and 1895. Notably, phenylalanine levels in mice injected with translatable molecules 1778 and 1895 were near wild-type levels at 24 hours post-injection, demonstrating protein expression from the mRNA treatment. Translatable molecule 1895 illustrated in FIG. 7 is identical to translatable molecule 1778 with the exception of an alternative 3' UTR structure.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A polynucleotide for expressing a human phenylalanine hydroxylase (PAH), wherein the polynucleotide comprises natural and chemically-modified nucleotides and is expressible to provide the human phenylalanine hydroxylase or a fragment thereof, and wherein the polynucleotide comprises a nucleotide sequence having at least 90% identity to a nucleotide sequence selected from SEQ ID NOs: 8-36 or a nucleotide sequence having at least 94% identity to the nucleotide sequence of SEQ ID NO: 37.

2. The polynucleotide of claim 1, wherein the chemically-modified nucleotides are selected from 5-hydroxycytidine, 5-methylcytidine, 5-hydroxymethylcytidine, 5-carboxycytidine, 5-formylcytidine, 5-methoxycytidine, 5-propynylcytidine, 2-thiocytidine;

5-hydroxyuridine, 5-methyluridine, 5,6-dihydro-5-methyluridine, 2'-O-methyluridine, 2'-O-methyl-5-methyluridine, 2'-fluoro-2'-deoxyuridine, 2'-amino-2'-deoxyuridine, 2'-azido-2'-deoxyuridine, 4-thiouridine, 5-hydroxymethyluridine, 5-carboxyuridine, 5-carboxymethylesteruridine, 5-formyluridine, 5-methoxyuridine, 5-propynyluridine, 5-bromouridine, 5-iodouridine, 5-fluorouridine;

pseudouridine, 2'-O-methyl-pseudouridine, $N^1$-hydroxypseudouridine, $N^1$-methyl-pseudouridine, 2'-O-methyl-M-methylpseudouridine, $N^1$-ethylpseudouridine, $N^1$-hydroxymethylpseudouridine, Arauridine;

$N^6$-methyladenosine, 2-aminoadenosine, 3-methyladenosine, 7-deazaadenosine, 8-oxoadenosine, inosine;

thienoguanosine, 7-deazaguanosine, 8-oxoguanosine, and 6-O-methylguanosine.

3. The polynucleotide of claim 1, wherein the chemically-modified nucleotides are 5-methoxyuridines.

4. The polynucleotide of claim 1, wherein the polynucleotide comprises a 5' cap, a 5' untranslated region, a coding region, a 3' untranslated region, and a tail region.

5. The polynucleotide of claim 1, wherein the polynucleotide comprises a nucleotide sequence selected from SEQ ID NOs: 8-37.

6. The polynucleotide of claim 1, wherein the polynucleotide comprises chemically-modified nucleotides in place of uridine and wherein the polynucleotide has greater translation efficiency as compared to a wild-type polynucleotide encoding PAH.

7. The polynucleotide of claim 6, wherein the chemically-modified nucleotides are 5-methoxyuridines.

8. The polynucleotide of claim 6, wherein the polynucleotide has at least 50% greater translation efficiency, at least two-fold greater translation efficiency, or at least three-fold greater translation efficiency as compared to a wild-type polynucleotide encoding PAH.

9. The polynucleotide of claim 6, wherein the polynucleotide comprises a nucleotide sequence selected from SEQ ID NOs: 8-37.

10. The polynucleotide of claim 6, wherein the polynucleotide comprises a nucleotide sequence that is at least 95% identical to a nucleotide sequence selected from SEQ ID NOs: 8-37.

11. The polynucleotide of claim 6, wherein the polynucleotide comprises a nucleotide sequence that is at least 97% identical to a nucleotide sequence selected from SEQ ID NOs: 8-37.

12. The polynucleotide of claim 6, wherein the polynucleotide comprises a nucleotide sequence that is at least 99% identical to a nucleotide sequence selected from SEQ ID NOs: 8-37.

13. A composition comprising the polynucleotide of claim 1 and a pharmaceutically acceptable carrier.

14. The composition of claim 13, wherein the pharmaceutically acceptable carrier comprises a transfection reagent, a nanoparticle, or a liposome.

* * * * *

SEQUENCE LISTING

```
<160> NUMBER OF SEQ ID NOS: 46

<210> SEQ ID NO 1
<211> LENGTH: 1359
<212> TYPE: DNA
<213> ORGANISM: Artificial Sequence
```

-continued

<220> FEATURE:
<223> OTHER INFORMATION: Consensus Human PAH DNA Coding Sequence

<400> SEQUENCE: 1
atgtccactg cggtcctgga aaacccaggc ttgggcagga aactctctga ctttggacag 60
gaaacaagct atattgaaga caactgcaat caaaatggtg ccatatcact gatcttctca 120
ctcaaagaag aagttggtgc attggccaaa gtattgcgct tatttgagga gaatgatgta 180
aacctgaccc acattgaatc tagaccttct cgtttaaaga aagatgagta tgaatttttc 240
acccatttgg ataaacgtag cctgcctgct ctgacaaaca tcatcaagat cttgaggcat 300
gacattggtg ccactgtcca tgagctttca cgagataaga agaaagacac agtgccctgg 360
ttcccaagaa ccattcaaga gctggacaga tttgccaatc agattctcag ctatggagcg 420
gaactggatg ctgaccaccc tggttttaaa gatcctgtgt accgtgcaag acggaagcag 480
tttgctgaca ttgcctacaa ctaccgccat gggcagccca tccctcgagt ggaatacatg 540
gaggaagaaa agaaaacatg gggcacagtg ttcaagactc tgaagtcctt gtataaaacc 600
catgcttgct atgagtacaa tcacattttt ccacttcttg aaaagtactg tggcttccat 660
gaagataaca ttccccagct ggaagacgtt tctcagttcc tgcagacttg cactggtttc 720
cgcctccgac ctgtggctgg cctgctttcc tctcgggatt tcttgggtgg cctggccttc 780
cgagtcttcc actgcacaca gtacatcaga catggatcca agcccatgta tacccccgaa 840
cctgacatct gccatgagct gttgggacat gtgcccttgt tttcagatcg cagctttgcc 900
cagttttccc aggaaattgg ccttgcctct ctgggtgcac ctgatgaata cattgaaaag 960
ctcgccacaa tttactggtt tactgtggag tttgggctct gcaaacaagg agactccata 1020
aaggcatatg gtgctgggct cctgtcatcc tttggtgaat tacagtactg cttatcagag 1080
aagccaaagc ttctccccct ggagctggag aagacagcca tccaaaatta cactgtcacg 1140
gagttccagc ccctctatta cgtggcagag agttttaatg atgccaagga gaaagtaagg 1200
aactttgctg ccacaatacc tcggcccttc tcagttcgct acgacccata cacccaaagg 1260
attgaggtct tggacaatac ccagcagctt aagattttgg ctgattccat taacagtgaa 1320
attggaatcc tttgcagtgc cctccagaaa ataaagtaa 1359

<210> SEQ ID NO 2
<211> LENGTH: 452
<212> TYPE: PRT
<213> ORGANISM: Artificial Sequence
<220> FEATURE:
<223> OTHER INFORMATION: Consensus Human PAH Amino Acid Sequence

<400> SEQUENCE: 2

Met Ser Thr Ala Val Leu Glu Asn Pro Gly Leu Gly Arg Lys Leu Ser
1 5 10 15

Asp Phe Gly Gln Glu Thr Ser Tyr Ile Glu Asp Asn Cys Asn Gln Asn
20 25 30

Gly Ala Ile Ser Leu Ile Phe Ser Leu Lys Glu Glu Val Gly Ala Leu
35 40 45

Ala Lys Val Leu Arg Leu Phe Glu Glu Asn Asp Val Asn Leu Thr His
50 55 60

Ile Glu Ser Arg Pro Ser Arg Leu Lys Lys Asp Glu Tyr Glu Phe Phe
65 70 75 80

Thr His Leu Asp Lys Arg Ser Leu Pro Ala Leu Thr Asn Ile Ile Lys
85 90 95

-continued

```
Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Pro Ala His Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Pro Ala His Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450
```

<210> SEQ ID NO 3
<211> LENGTH: 129
<212> TYPE: RNA
<213> ORGANISM: Tobacco Etch Virus -continued

<400> SEQUENCE: 3
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauag 129

<210> SEQ ID NO 4
<211> LENGTH: 6
<212> TYPE: RNA
<213> ORGANISM: Unknown
<220> FEATURE:
<223> OTHER INFORMATION: Kozak Sequence

<400> SEQUENCE: 4 gccacc 6

<210> SEQ ID NO 5
<211> LENGTH: 1359
<212> TYPE: RNA
<213> ORGANISM: Homo sapiens

<400> SEQUENCE: 5
auguccacug cgguccugga aaacccaggc uugggcagga aacucucuga cuuuggacag 60
gaaacaagcu auauugaaga caacugcaau caaaauggug ccauaucacu gaucuucuca 120
cucaaagaag aaguuggugc auuggccaaa guauugcgcu uauuugagga gaaugaugua 180
aaccugaccc acauugaauc uagaccuucu cguuuaaaga aagaugagua ugaauuuuuc 240
acccauuugg auaaacguag ccugccugcu cugacaaaca ucaucaagau cuugaggcau 300
gacauuggug ccacugucca ugagcuuuca cgagauaaga agaaagacac agugcccugg 360
uucccaagaa ccauucaaga gcuggacaga uuugccaauc agauucucag cuauggagcg 420
gaacuggaug cugaccaccc ugguuuuaaa gauccugugu accgugcaag acggaagcag 480
uuugcugaca uugccuacaa cuaccgccau gggcagccca ucccucgagu ggaauacaug 540
gaggaagaaa agaaaacaug ggcacagugu uucaagacuc ugaaguccuu guauaaaacc 600
caugcuugcu augaguacaa ucacauuuuu ccacuucuug aaaaguacug uggcuuccau 660
gaagauaaca uuccccagcu ggaagacguu ucucaguucc ugcagacuug cacugguuuc 720
cgccuccgac cuguggcugg ccugcuuucc ucucgggauu ucuugggugg ccuggccuuc 780
cgagucuucc acugcacaca guacaucaga cauggaucca agcccaugua uacccccgaa 840
ccugacaucu gccaugagcu guugggacau gugcccuugu uuucagaucg cagcuuugcc 900
caguuuuccc aggaaauugg ccuugccucu cugggugcac cugaugaaua cauugaaaag 960
cucgccacaa uuuacugguu uacuguggag uuugggcucu gcaaacaagg agacuccaua 1020
aaggcauaug gugcugggcu ccugucaucc uuuggugaau uacaguacug cuuaucagag 1080
aagccaaagc uucuccccu ggagcuggag aagacagcca uccaaaauua cacugucacg 1140
gaguuccagc cccucuauua cguggcagag aguuuuaaug augccaagga gaaaguaagg 1200
aacuuugcug ccacaauacc ucggcccuuc ucaguucgcu acgacccaua cacccaaagg 1260
auugaggucu uggacaauac ccagcagcuu aagauuuugg cugauuccau uaacagugaa 1320
auuggaaucc uuugcagugc ccuccagaaa auaaaguaa 1359

<210> SEQ ID NO 6
<211> LENGTH: 158
<212> TYPE: RNA
<213> ORGANISM: Xenopus sp.

-continued

<400> SEQUENCE: 6
cuagugacug acuaggaucu gguuaccacu aaaccagccu caagaacacc cgaauggagu 60
cucuaagcua cauaauacca acuuacacuu acaaaauguu gucccccaaa auguagccau 120
ucguaucugc uccuaauaaa aagaaaguuu cuucacau 158

<210> SEQ ID NO 7
<211> LENGTH: 100
<212> TYPE: RNA
<213> ORGANISM: Unknown
<220> FEATURE:
<223> OTHER INFORMATION: Poly(A) 100 Tail

<400> SEQUENCE: 7
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa 100

<210> SEQ ID NO 8
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 8
augagcacag cuguauuaga aaaccccggc cugggaagga aacuaucuga uuucggacaa 60
gagacaagcu acauugaaga uaacugcaac cagaacggcg cuauaucacu gaucuuuagc 120
cugaaggaag aagucggcgc uuuggcuaag guucugcggc ucuuugagga gaaugacgug 180
aauuugacgc acaucgaauc aagaccgagc aggcugaaga aggacgaaua cgaauucuuu 240
acccaucucg acaagaggag ucugccugca cugacgaaca uuaucaagau ccugcgccau 300
gacauuggug ccaccguuca ugaacugucc cgggauaaga agaaggacac agugccaugg 360
uuuccacgga ccauucagga acuggacaga uucgcaaauc agauccuguc cuauggagcu 420
gagcuggaug ccgaucaucc cggcuuuaag gacccagugu auagggcucg aaggaagcag 480
uuugcugaca ucgcguauaa cuaucggcac ggccagccua uuccaagagu cgaguauaug 540
gaggaagaga aaaagacaug ggcacagug uucaagacuc ugaaguccuu guauaagacc 600
caugcuugcu acgaguauaa ccacaucuuu cccuugcugg aaaaguacug uggcuuucau 660
gaggacaaca ucccacaacu ggaggacguu agccaguucc uccaaacaug uaccggguuu 720
aggcuacggc ccguagcugg ccugcugagc ucaagagacu uccugggcgg cuuggccuuu 780
cggguguucc auuguacgca guauauccgc cacgguucua agcccaugua uaccccggag 840
cccgauauuu gucaugaacu ccucggccac gugccuuugu uuuccgaccg aaguuugca 900 caguucaguc aggaaauagg ccucgccucc cugggggcuc cggacgagua uauagagaag 960
cuggcuacua ucuauuggu caccguggaa uuuggucugu guaaacaggg cgacagcauu 1020
aaggcuuaug gcgcuggcuu gcuguccucu uuuggggaac uucaauauug ccugucugag 1080
aagccuaagc ugcugccccu ggaacuggaa aagacggcua uucagaacua uaccgucacu 1140
gaguuucaac cauuguauua cguagccgag agcuuuaaug augccaagga gaaaguccgc 1200
aauuuugccg ccacgauacc gcggccuuuu uccgugcgcu augacccgua cacacagcgu 1260
auugaggugc uggauaacac ucaacaguug aagauucugg cugacucgau uaacuccgaa 1320
auugggaucc uguguagcgc auuacaaaag aucaaauaa 1359

-continued

<210> SEQ ID NO 9
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 9
augucaaccg cuguauuaga gaacccagga uuaggcagaa agcugaguga cuucggccaa 60
gaaaccucuu acaucgagga caacugcaac cagaaugggg cuauuucauu aauuuuuagc 120
cugaaggagg aagucggcgc ucuggcuaaa gugcugaggc uguuugagga aaacgacgug 180
aaucuaacuc acauugaauc uaggccuuca cggcucaaga aggacgaaua ugaauuuuuu 240
acucaucugg acaagcgcuc auugcccgcu cugacgaaua ucaucaagau ccuucggcac 300
gauauugggg cuaccgugca cgaauuguca cgggauaaga agaaggauac ggucccuugg 360
uuuccccgca cuauccaaga acuggaucgc uuugccaacc aaauucuguc cuacggggca 420
gaauuggacg cugaucaucc gggguucaaa gacccagugu auagggcuag gaggaagcag 480
uuugccgaca uugccuauaa cuaucgacac gggcagccca uuccccgugu ggaguacaug 540
gaggaagaga agaaaaccug ggaaccgugg uucaagacgu ugaagagucu guauaagaca 600
caugccuguu acgaguauaa ucauaucuuc ccccugcucg agaaguauug uggcuuucau 660
gaggauaaca uaccacagcu ggaggaugug ucacaguuuc ugcaaacaug uacaggcuuc 720
cggcugaggc cuguugcugg ccuacugagc ucuagagacu uucuuggcgg ccuggcguuu 780
agaguguuuc auugcacaca guacauaaga cauggcagca agcccaugua uaccccggaa 840
ccagacauuu gucaugaauu gcugggucau guuccccuau uucugaccg gaguuucgca 900 caguuuagcc aggagauagg ccuggcuagc uugggcgcuc ccgaugagua uauugagaag 960
cuggcaacaa ucuauugguu caccguugaa uuuggccugu guaaacaggg ggacucgauc 1020
aaggccuaug gcgcugggcu gcuaucgagu uucggcgaac ugcaguauug uuuguccgaa 1080
aagccuaagc ugcugccauu ggagcuggaa aagacagcua uccaaaacua cacggucacc 1140
gaguuucagc cacuguauua cguagccgaa uccuuuaacg augcaaagga aaagguccgc 1200
aauuucgcug ccacuauucc gcggccuuuu aguguacgau augacccgua uacccaaagg 1260
auugaggugc uggacaauac ucagcagcug aaaauacugg cugacuccau caacucugag 1320
auuggcaucc ugugcuccgc cuugcaaaag aucaaauaa 1359

<210> SEQ ID NO 10
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 10
augaguacag cgguauugga aaauccagga cuugggagaa aauugagcga cuuuggccaa 60
gaaacgucgu auaucgaaga uaauuguaac cagaauggag caauuucacu gaucuuuagu 120
cugaaagagg aaguuggcgc acuggcuaag guucugaggu uguuugagga gaacgacgua 180
aaccugaccc auauugagag caggccgucu agauugaaga aggacgaaua cgaguuuuuc 240
acccaucugg auaagcguuc cuugcccgcc cugaccaaca uaaucaagau uuugcggcau 300
gacaucggcg cuacggugca cgaacuauca cgcgacaaga agaaagacac cgugccaugg 360
uuuccaagga ccauacagga gcuggaccgg uuugcgaacc agauccugag cuacggcgcc 420

-continued

```
gagcuggacg ccgaccaucc gggguucaag gauccagugu aucgcgcuag gaggaagcag    480
uuugccgaua uugcuuauaa cuaucgacau ggucaaccca uuccacgggu ggaguauaug    540
gaggaagaga agaaaaccug gggcaccguc uuuaagacgc ugaagucccu guacaagacc    600
cacgcuugcu acgaguauaa ccacauuuuu ccacugcugg aaaaguauug uggcuuucau    660
gaggacaaua uuccgcaacu ggaggacgug ucucaguucu ugcaaacgug uaccggguuu    720
agacugcgcc caguggccgg ccuguuguccc ucccgggacu uucugggcgg ccuggccuuc    780
cggguguucc auugcacgca guacauaaga cauggcagca agccaaugua uacaccagag    840
ccugacauuu gucacgaacu gcugggccau gugccguuau uuuccgaucg aagcuucgcc    900
caguuuaguc aggaaauugg ccuggcgucc uugggugccc ccgaugagua uauugaaaag    960
cucgcaacua ucuauugguu uacugucgaa uucggccugu guaaacaggg cgauucuauc   1020
aaggcuuaug gcgcuggccu gcugagcuca uuuggggaac uccaauauug uuugucugag   1080
aagccuaagu ugcugccucu ggaacuggaa aagacggcaa uccagaacua uacagugacg   1140
gaauuucagc cucuguacua uguagcagaa agcuuuaaug augcuaagga aaagguucgc   1200
aacuucgcug ccacaauacc acggccauuu uccguccgcu augacccaua uacacagcgg   1260
auugaggugc uggacaacac acagcaacug aaaauccugg ccgauaguau uaacagcgag   1320
auuggcaucc uguguagcgc ccugcaaaag aucaaguaa                          1359
```

<210> SEQ ID NO 11
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 11

```
augucaaccg cugugcuuga aaaccccgga cucggccgca aguuaucuga uuucggacaa     60
gaaaccucau acauugagga caacugcaac cagaacgggg cgaucucacu gaucuucucg    120
cugaaagaag aagucggagc auuggcgaag guccugaggc uguucgagga aaacgacgug    180
aaccugaccc acauagaauc gcggccguca cggcuaaaga aggaugaaua cgaguucuuc    240
acgcaccugg acaagcgguc gcugccggcg cugacuaaca ucaucaagau ucugcggcac    300
gauaucgggg caaccgugca ugagcugagc cgggacaaga agaaggacac cgugccgugg    360
uuuccccgga caauccagga gcuggaccgc uucgccaauc aaauccugag cuacggugca    420
gaacuggacg cggaccaccc aggguucaag gacccggugu acagagccag gagaaagcag    480
uucgccgaua uugcauacaa cuaccgccac ggccagccga uuccccgcgu ggaguacaug    540
gaagaagaga agaaaaccug gggacugug uucaagacuc ugaagucccu guauaagacc    600
cacgcguguu augaguacaa ccauauuuuc ccgcugcugg aaaaguauug cggauuccau    660
gaggauaaca uuccgcagcu ggaggacgug ucacaguuuc ugcaaacuug caccggauuc    720
cggcugaggc cggucgccgg auugcucucc ucccgggauu ucccucggcgg acuggcauuc    780
agaguguucc acugcaccca guacauuaga cacgggucga agccgaugua caccccugag    840
ccugacaucu gccaugaacu gcuuggccac gucccguugu uuucggaccg cucauucgca    900
caauucagcc aggagauugg acucgcauca cuuggagccc ccgaugagua caucgagaag    960
cucgccacca ucuacugguu caccguggag uucggccugu gcaaacaggg ggauuccauc   1020
aaagcuuacg gcgcgggccu ccuguccuca uucggggaau ugcaguacug ucucuccgaa   1080
aagccgaagc ugcugccccu ugaacucgaa aagaccgcaa uccagaacua caccgugacu   1140
```

-continued gaauuucagc cgcucuacua cguggccgag agcuucaacg acgcuaagga aaagguccgc 1200
aacuucgccg ccacuauccc gcgaccguuc uccgugcgcu acgacccaua cacucagcgc 1260
aucgaggugc uggacaauac ccagcagcuc aagauccugg cugacuccau caacucggag 1320
auugggaucc ugugcucggc ccugcaaaag aucaaguaa 1359

<210> SEQ ID NO 12
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 12
augagcaccg ccguccuuga aaacccuggc cuuggaagaa agcugaguga cuucggacag 60
gaaacuucgu auaucgagga caacugcaac cagaacgggg ccauuagccu gaucuuuuca 120
cugaaagagg aggucggagc ucuggccaag guccuucggc uguucgagga aaaugacgug 180
aaccugacac acaucgaauc ccggccgucg cggcugaaga aggaugaaua cgaguucuuc 240
acgcaucugg acaagcgguc ccugccggcc uugaccaaca ucauaaagau ucugcggcac 300
gauauuggcg cgacugugca cgagcugucc cgcgacaaaa agaaggacac cgugcccugg 360
uuuccgagga cuauucagga gcuggaccgg uucgcuaacc aaauccuauc cuacggagcc 420
gagcuggacg cggaucaccc gggauucaag gacccagugu accgagcacg gagaaagcag 480
uucgcagaca uugccuacaa cuaccgccac gggcagccaa ucccccgcgu ggaguauaug 540
gaagaagaga agaaaaccug ggggaccgug uuuaagaccc ucaagucacu guacaagacc 600
caugccugcu acgaguacaa ccacaucuuc ccgcugcugg aaaaguacug cggauuccac 660
gaggauaaca ucccccaauu ggaagaugug ucacaguucu uacaaacgug uacuggguuc 720
agacuccggc cgguggcggg ccugcugagc ucccgcgacu uccugggcgg ccuggccuuc 780
cggguguucc acugcaccca guacaucaga cacgguagca agccgaugua caccccggaa 840
cccgacaucu gccaugaacu ccugggacac gugcccuugu ucuccgaccg cuccuucgcg 900
caauucuccc aagaaaucgg acuggcuucc cugggugccc cugaugagua cauugaaaag 960
cucgccacca ucuauugguu cacgguggag uucgggcugu gcaaacaggg ggacucgauc 1020
aaggccuacg ggccggccu ucuguccucu uuuggggaac ugcaguacug ccuguccgag 1080
aagccgaagc ugcucccgcu ggagcuggaa aagaccgcaa uucagaacua caccgugacc 1140
gaauuccagc cgcucuacua cguggcggaa agcuucaaug augccaagga gaagguccgc 1200
aacuucgccg ccaccauucc gaggccguuc uccguccgcu acgaccccua cacccaaagg 1260
aucgaggugc ucgacaacac ccagcagcug aagauccugg ccgacucgau uaacuccgaa 1320
aucggaaucc uguguagcgc guugcagaag aucaaguaa 1359

<210> SEQ ID NO 13
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 13
augucuacug cugugcuuga aaaccccgga cucggccgaa agcuuuccga cuucggacag 60
gaaaccucgu acaucgagga uaauugcaac cagaauggug ccaucucccu caucuuuucg 120
cugaaagaag aggucggcgc ccuggcuaag guccugaggc uguucgaaga gaacgacguc 180

-continued

```
aaccugaccc acaucgaauc aagaccgucc agacucaaga aggaugaaua ugaauucuuu    240

acccaccugg acaagaggag ccugccggcc cuuaccaaca ucauuaagau ucugcgccac    300

gacaucggcg cuaccgugca ugaacugucc cgcgacaaga agaaggauac cgugccaugg    360

uucccccgga cgauucagga gcucgaccgg uucgcaaacc agauccuguc auacggagcc    420

gaacuggacg cggaccaccc gggauucaag gacccugugu accgcgcacg gcggaagcag    480

uucgcggaca ucgccuacaa cuaccgccac gggcaaccca uuccgcgcgu cgaguacaug    540

gaagaggaga agaaaaccug ggggacugug uucaagaccc ucaagucccu guauaagacc    600

cacgccugcu acgaguacaa ccacaucuuc cccccugcugg agaaguacug uggcuuccau    660

gaggacaaca ucccgcaguu ggaggacgug ucgcaguuuc uccaaaccug uacuggauuc    720

agacugaggc ccguggccgg ucugcucuca ucgcgggacu uucugggagg ccuggcauuc    780

cgcguguucc acugcacgca guacauuaga cauggaucca agccaaugua cacucccgaa    840

ccugacaucu gccaugaacu gcugggccac gugccacucu uucggaucg gagcuucgcg    900

caauucuccc aagaaaucgg guuggcaucg cugggugccc cggaugagua cauugagaag    960

cuggccacca ucuacugguu caccguggag uucggacugu gcaaacaggg ggauagcauc   1020

aaggcauaug gcgcaggccu gcugagcucg uucggagagc uccaguacug ccucucggaa   1080

aagccuaagu ugcuuccgcu ggaacuggag aaaacagcaa uccagaacua caccgugacc   1140

gaguuccagc cccucuacua cguggcggag agcuucaacg acgcuaagga gaagguccgc   1200

aacuucgcgg cgacgauucc ucggccuuuc uccgugcgcu acgacccgua cacccagcgg   1260

auugaagugu uagauaauac ccagcagcug aagauucugg cggacuccau caacuccgaa   1320

aucggaaucc ugugcuccgc auugcaaaag auuaaguaa                          1359
```

<210> SEQ ID NO 14
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 14

```
augagcacag cuguauuaga aaaucccggg cuaggccgca aauugaguga cuuugggcag     60

gagacuagcu acauugagga caacuguaac cagaacggcg cuauaagccu uaucuuuucg    120

cugaaagagg aaguuggcgc ucuggcuaag guccugaggu uguuugagga gaacgacgug    180

aaccugacac acauugagag cagaccaagc cgacugaaga aggacgaaua cgaauucuuu    240

acgcaccugg acaagagguc uuuaccggcu cuuacgaaca ucaucaagau ccugagacau    300

gauauugggg cuacagugca ugagcuuucc cgcgacaaga agaaggacac agugcccugg    360

uucccacgga ccauucagga acucgaucgc uuugcuaauc aaauacucuc auacggcgcu    420

gagcuggacg cugaucaucc gggcuuuaag gacccagugu auagggcccg uaggaagcag    480

uucgcugaca ucgccuacaa uuaucggcac ggccaaccca uuccccgagu cgaguacaug    540

gaggaagaga aaaagaccug gggcaccguu uucaaaaccc ugaaguccuu guauaagacc    600

cacgcuuguu augaguauaa ucauaucuuu ccuuugcucg aaaaguauug uggcuuucau    660

gaggacaaca uuccccaacu ggaagaugua ucccaguucc uacaaacaug cacuggcuuu    720

agauugcggc caguggcagg ccuucugagu ucaagggacu uucuuggcgg ccuggcuuuu    780

cgggucuuuc auuguaccca guacauucgg cauggaucca agccgaugua uacccccgag    840

ccugacauuu gccaugaacu gcugggucau guaccccucu uuuccgaucg gagcuucgcu    900
```

-continued

```
caguuuagcc aggaaauugg uuuggcuuca cugggugcac cagaugagua uauagagaag    960

uuggcuacga ucuauugguu uaccguggag uuuggccugu gcaaacaggg cgacaguauc   1020

aaggccuaug gcgccggccu gcuaaguagc uucggagaac uucaguauug ucucucugaa   1080

aaaccuaagc uccuuccgcu ggagcuggaa aagaccgcua uucaaaacua uacugugaca   1140

gaauuucagc cucuguauua cguugcugaa uccuuuaaug acgcuaagga aaaaguccgg   1200

aacuuugcug caacgauccc uagaccauuc ucugugcgcu augacccaua uacucaaagg   1260

auugaagugc uggauaauac ucagcagcuc aagauuuugg cugauucuau caacuccgaa   1320

aucgggauac uguguuccgc ccugcaaaag aucaaguaa                          1359
```

```
<210> SEQ ID NO 15
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 15

augagcaccg ccguccuuga gaacccuggc uugggaagaa aguuguccga uuuuggccaa     60

gaaaccuccu auaucgagga uaacugcaac cagaacggag ccaucucccu caucuucucg    120

cugaaagagg aagucggcgc ucuggccaag guccuccgcc uguucgagga aaacgacgug    180

aaccugaccc acauugaaag caggcccucg agacucaaga aggacgaaua cgaauucuuc    240

acucaccugg acaagcgcuc acuuccggcc cugaccaaca uuaucaagau ccuucggcac    300

gacauuggug ccaccgugca cgaacugagc cgcgacaaga agaaggacac ugugccaugg    360

uuuccgcgga ccauccagga gcucgauaga uucgccaauc aaauucucuc guacggagcg    420

gaacuggacg ccgaccaucc uggguuuaag gacccggucu accgggccag gaggaagcag    480

uucgccgaua ucgccuacaa cuaucgccac ggucaaccaa ucccccgagu ggaguacaug    540

gaggaggaga aaaagaccug ggguaccgug uucaagacuc ugaagucacu guacaaaacu    600

caugccugcu acgaguacaa ccacaucuuu ccucuucucg aaaaguacug cggauuccac    660

gaggacaaca ucccucaacu cgaggacgug ucgcaguucc ugcaaacuug uacuggauuc    720

cgccugcggc cuguggccgg acugcucucc ucccgggauu uccucggugg ccuggccuuu    780

cggguguucc auugcaccca guacaucaga cacggcucca agcccaugua cacaccugaa    840

ccugacaucu gccaugagcu gcucggucac gugccucugu ucucggaccg guccuucgcc    900

caauucagcc aggaaauugg ccucgccuca cugggugccc cugaugagua caucgaaaag    960

cuggccacca ucuacugguu caccguggag uucggacugu gcaaacaggg agacuccauu   1020

aaggcguacg gugccggccu guuguccucc uucggggaac ugcaguauug cuugagcgaa   1080

aagccuaaac ugcugccccu ggagcucgaa aagaccgcga uccagaacua caccgugacu   1140

gaguuccagc cucuguacua cguggccgaa uccuucaacg acgcuaagga aaagguccgc   1200

aauuucgccg caaccauccc aagacccuuc uccgugcgcu acgaccccua cacgcagcgg   1260

auugaagugc uggacaacac ccagcagcug aagauucugg ccgauucuau caacuccgag   1320

aucggaaucc uguguagcgc gcugcagaag auuaaguaa                          1359
```

```
<210> SEQ ID NO 16
<211> LENGTH: 1359
<212> TYPE: RNA
<213> ORGANISM: Artificial Sequence
<220> FEATURE:
<223> OTHER INFORMATION: Codon-Optimized PAH Coding Sequence
```

-continued

<400> SEQUENCE: 16
auguccaccg ccguccucga aaaccccggu cuggguagaa agcucuccga cuucggucaa 60
gaaacuuccu acaucgagga uaacugcaac cagaacggug ccaucagccu gauuuucuca 120
cugaaagaag aggucggagc ccuggccaag guccucagac uguucgaaga gaacgauguc 180
aaccugaccc auaucgaaag ccgccccagc cggcugaaga aggacgaaua cgaauucuuc 240
acacaccucg acaagagguc ccuuccggcc uugacuaaca uuaucaagau ccuccggcac 300
gacauuggcg ccacugugca ugaacugagc cgcgauaaga agaaggacac cgugcccugg 360
uucccaagaa cuauccagga gcuggaccgc uucgccaauc aaauccucuc cuaugggggcc 420 gaacuugacg ccgaccaucc uggguuuaag gaccccgugu accgggccag gcggaagcag 480
uucgccgaua ucgccuacaa cuauagacac ggacagccga ucccccgcgu ggaguacaug 540
gaagaggaga aaaagacuug ggcaccgug uucaagaccc ucaaguccu guacaagacc 600 caugccugcu acgaguacaa ccacauuuuc ccgcugcucg agaaguacug cggauuccac 660
gaagauaaua uuccgcagcu cgaggacgug ucccaguucc uccaaacuug cacugguuuu 720
cggcugaggc cgguggcggg auugcucucc ucccgggauu uucugggagg ccucgccuuc 780
cgaguguucc acugcacuca guauauucgg cacggaucca agccaaugua cacuccugaa 840
cccgacaucu gucacgaacu gcugggccac gugccccucu ucuccgaccg gagcuucgcc 900
caguucagcc aggaaaucgg ccucgcaagc cugggugccc cugacgagua caucgaaaag 960
cucgcgacca ucuacugguu caccguggag uucggucugu gcaaacaggg agauuccauc 1020
aaggccuacg gcgccggccu gcuuuccucg uucggagagc ugcaauacug ccugucggag 1080
aagccaaagc uccugccguu ggagcucgaa aagacugcca uccaaaacua caccgugacu 1140
gaauuucagc cucuguacua cguggccgag uccuucaacg acgccaagga gaaaguccgc 1200
aacuucgcug cuaccauccc ucgcccguuu uccgugcgcu acgacccuua cacccaacgg 1260
auugaggugc ucgacaacac ucagcagcuu aagauacugg ccgacuccau caacucggag 1320
aucggaauuc uguguagcgc gcugcagaag auuaaguaa 1359

<210> SEQ ID NO 17
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 17
auguccacug ccguucucga aaacccaggc cucggaagaa aguuaagcga uuuuggccag 60
gaaaccuccu auaucgagga uaacuguaac cagaauggcg cuauuagucu gaucuuuagu 120
cugaaagaag aaguuggugc acuggcaaag guccucagac uguuugagga aaaugacgug 180
aaccugaccc auauugaaag caggccuagc aggcucaaga aggacgaaua ugaguucuuu 240
acucauuugg acaagcgauc gcugccugcu uugacgaaca ucaucaagau ucuccggcac 300
gacaucggcg caaccgugca ugaacugagc agagacaaga agaaggacac ggugccaugg 360
uuuccaagga caauucagga gcuggaccgc uucgcuaauc aaauccuguc auauggggcu 420
gaacucgacg cugaccaccc uggcuuuaag gauccugucu aucgagcucg gcgcaaacag 480
uuugccgaua uagcuuauaa cuaucggcau ggccaaccca ucccccgggu ggaguauaug 540
gaggaggaga agaaaacuug gggcacagug uuuaagacac ugaaguccuu guauaagaca 600
caugcaugcu acgaguacaa ucauauuuuc ccgcugcuug agaaguauug uggcuuucau 660
gaggauaaca uuccccaacu ggaggacgug ucccaguuuc ugcaaacaug cacaggcuuu 720
aggcugcggc cuguugcugg ccuacugucc ucccgggacu uuuugggcgg acuggccuuc 780
cgcguguucc auuguaccca guacauuaga cacggcucua agccaaugua uaccccugag 840
ccugacauuu gccaugaacu gcucggccac gugccacugu uuagcgaucg gagcuucgcg 900
caauucagcc aggaaauugg gcuggccucu uugggggccc ccgacgagua caucgagaag 960
uuggcuacca ucuacugguu cacgguagag uuugggcugu guaaacaggg cgacagcauu 1020
aaggccuaug gcgcuggccu ccuguccucc uuuggugaac ugcaguacug ucuuagcgaa 1080
aaaccgaagc ugcugcccuu ggagcucgaa aagaccgcua uacagaauua caccguaacu 1140
gaauuucagc cccuguauua uguagcagag agcuuuaacg acgccaagga aaaaguccgc 1200
aacuuugcug ccacaauucc aaggccuuuu uccgugcguu augaccccua uacgcaaagg 1260
auagaagugu uggacaauac ccaacagcug aagauucugg cugauuccau aaacagcgaa 1320
aucgguaucc uguguuccgc ucugcaaaag aucaaguaa 1359

<210> SEQ ID NO 18
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 18
augucaacug ccgugcucga aaaccccgga cuuggaagaa agcugucgga cuucggucaa 60
gaaaccucau acaucgagga uaacugcaac cagaaugggg cgauuucccu caucuucuca 120
cugaaagaag aagucggugc acuggcgaag guccugcggc uguucgaaga gaacgaugug 180
aaccucacuc auaucgagag caggccuucc cggcuaaaga aggacgaaua cgaguucuuu 240
acccaccuug acaagagaag ccucccggcc cugaccaaca uaaucaagau ucugagacac 300
gacaucgggg ccaccgugca cgagcugucc agggacaaga agaaggacac ugugccaugg 360
uucccgcgca cgauccaaga guuggaucgc uucgcuaacc aaauccuguc cuacggcgcc 420
gaacuggacg ccgaccaccc cggauucaag gaccccgugu aucgggcccg gagaaagcag 480
uuugcugaua uugcauacaa cuaccgccau ggacagccca uccccgcgu ggaguacaug 540 gaggaggaaa agaaaacaug gggcacugug uucaagaccc ucaaguccu guacaagacc 600 caugcuugcu acgaguacaa ccacauuuuc ccucugcugg agaaguacug cggcuuccac 660
gaggacaaca ucccccaacu ggaggacgug ucccaguucc ugcaaaccug uacuggguuc 720
cgccugcggc ccguggcggg ccugcugucc ucucgggacu uucuuggugg acucgccuuc 780
cgcguguucc acugcaccca guacauucgg cauggcucca aacccaugua cacucccgaa 840
cccgacauuu gccacgaacu guugggccac gugccccugu ucuccgaccg gagcuucgcc 900
caguucagcc aggagauugg acuggccucg cugggggcgc cugaugagua cauugagaag 960
uuggccacua ucuacugguu cacuguggaa uucggacugu gcaaacaggg cgauuccauc 1020
aaggcuuacg gagcaggacu gcugucgagc uuuggcgaac ugcaguacug ccucuccgaa 1080
aagccuaagc uccucccgcu cgaacuugaa aagaccgcga uccagaacua uacugugacc 1140
gaauuucagc cgcuguacua cguggccgag uccuucaacg augccaagga aaagguccgc 1200
aacuucgccg ccaccauccc ucggccguuc uccguccgau augacccgua cacucagagg 1260
aucgaagugc uggauaauac ucagcagcuc aagauccugg cggacaguau caauagcgag 1320
auuggaaucc uguguucugc ccugcaaaag aucaaguaa 1359

<210> SEQ ID NO 19
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 19
augagcaccg ccguacuuga aaacccugga cugggccgca aacuguccga cuucggccaa 60
gagacuuccu auaucgagga caacugcaac cagaauggug ccauuucacu gaucuuuagu 120
cugaaggagg aagucggugc ccuggcuaag guucugcggu uguuugaaga aaacgacgug 180
aaucugacgc auauagaaag caggcccagc aggcugaaga aggaugagua cgaauucuuu 240
acucaccucg acaagcgguc uuugcccgcc uuaacuaaca uuaucaagau cuugcgccau 300
gauauuggug cuaccguaca ugaacuguca cgggauaaga agaaggacac gguuccaugg 360
uuuccucgua caauucagga auuggacaga uucgcaaacc agaucuuaag uuauggcgcu 420
gaacuggacg ccgaucaucc cggcuuuaag gaccccgugu aucgagcuag gagaaagcag 480
uuugccgaca ucgcuuauaa uuaucggcau ggccagccua uuccgagggu ggaguauaug 540
gaggaagaga agaaaaccug ggguacugug uuuaagacuc ugaagucucu guauaagacc 600
cacgcuuguu acgaguacaa ucacauauuc ccgcuguugg agaaguauug uggcuuucau 660
gaggacaaca ucccacaacu ggaggacgug ucccaguucc uucaaaccug uaccggcuuu 720
agacugaggc ccguagcagg gcugcugagc agcagagauu uucugggagg cuuggcauuu 780
cgaguguuuc auuguacaca guauauucgc cauggcucga aacccaugua cacacccgag 840
ccagauaucu gucaugagcu ccugggccac gucccccugu uuuccgaccg gagcuucgcu 900
caguuuagcc aagaaauagg ccucgcuagc uugggugcac cagacgagua uauugaaaag 960
cuggcgacca uauauugguu uacuguggaa uucggccugu guaaacaggg cgauuccauu 1020
aaggcauaug gcgcuggccu ccuauccucu uuuggcgaac ugcaauauug cuuguccgag 1080
aagccuaagc uguugccacu cgaacuggaa aagacugcua uucaaaacua uaccguuacu 1140
gaauuccagc cucuguacua cguggcugaa uccuuuaaug acgcuaaaga gaaaguucgg 1200
aacuuugcug ccacaauccc acggccguuu ucugugcgcu augacccgua cacacagagg 1260
aucgaagucc uggacaacac ccagcagcua aagauccugg cugauaguau uaauagcgag 1320
auugggaucc uguguagugc ucugcaaaag auuaaguaa 1359

<210> SEQ ID NO 20
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 20
augagcaccg ccguccuuga aaacccuggc cuuggaagaa agcugaguga cuucggacag 60
gaaacuucgu auaucgagga caacugcaac cagaacgggg ccauuagccu gaucuuuuca 120
cugaaagagg aggucggagc ucuggccaag guccuucggc uguucgagga aaaugacgug 180
aaccugacac acaucgaauc ccggccgucg cggcugaaga aggaugaaua cgaguucuuc 240
acgcaucugg acaagcgguc ccugccggcc uugaccaaca ucauaaagau ucugcggcac 300
gauauuggcg cgacugugca cgagcugucc cgcgacaaaa agaaggacac cgugcccugg 360
uuuccgagga cuauucagga gcuggaccgg uucgcuaacc aaauccuauc cuacggagcc 420

-continued gagcuggacg cggaucaccc gggauucaag gacccagugu accgagcacg gagaaagcag 480
uucgcagaca uugccuacaa cuaccgccac gggcagccaa ucccccgcgu ggaguauaug 540
gaagaagaga agaaaaccug ggggaccgug uuuaagaccc ucaagucacu guacaagacc 600
caugccugcu acgaguacaa ccacaucuuc ccgcugcugg aaaaguacug cggauuccac 660
gaggauaaca ucccccaauu ggaagaugug ucacaguucu uacaaacgug uacuggguuc 720
agacuccggc cgguggcggg ccugcugagc ucccgcgacu uccugggcgg ccuggccuuc 780
cggguguucc acugcaccca guacaucaga cacgguagca agccgaugua caccccggaa 840
cccgacaucu gccaugaacu ccugggacac gugcccuugu ucuccgaccg cuccuucgcg 900
caauucuccc aagaaaucgg acuggcuucc cugggugcac cugaugaaua cauugaaaag 960
cucgccacaa uuuacugguu uacuguggag uuugggcucu gcaaacaagg agacuccaua 1020
aaggcauaug gugcugggcu ccugucaucc uuuggugaau uacaguacug cuuaucagag 1080
aagccaaagc uucuccccu ggagcuggag aagacagcca uccaaaauua cacugucacg 1140
gaguuccagc cccucuauua cguggcagag aguuuuaaug augccaagga gaaaguaagg 1200
aacuuugcug ccacaauacc ucggcccuuc ucaguucgcu acgacccaua cacccaaagg 1260
auugaggucu uggacaauac ccagcagcuu aagauuuugg cugauuccau uaacagugaa 1320
auuggaaucc uuugcagugc ccuccagaaa auaaaguaa 1359

<210> SEQ ID NO 21
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 21
augagcaccg ccguccuuga gaacccuggc uugggaagaa aguuguccga uuuuggccaa 60
gaaaccuccu auaucgagga uaacugcaac cagaacggag ccaucucccu caucuucucg 120
cugaaagagg aagucggcgc ucuggccaag guccuccgcc uguucgagga aaacgacgug 180
aaccugaccc acauugaaag caggcccucg agacucaaga aggacgaaua cgaauucuuc 240
acucaccugg acaagcgcuc acuuccggcc cugaccaaca uuaucaagau ccuucggcac 300
gauaucgggg caaccgugca ugagcugagc cgggacaaga agaaggacac cgugccgugg 360
uuuccccgga caauccagga gcuggaccgc uucgccaauc aaauccugag cuacggugca 420
gaacuggacg cggaccaccc aggguucaag gacccggugu acagagccag gagaaagcag 480
uucgccgaua uugcauacaa cuaccgccac ggccagccga uuccccgcgu ggaguacaug 540
gaagaagaga agaaaaccug ggggacugug uucaagacuc ugaagucccu guauaagacc 600
cacgcguguu augaguacaa ccauauuuuc ccgcugcugg aaaaguauug cggauuccau 660
gaggauaaca uuccgcagcu ggaggacgug ucacaguuuc ugcaaacuug caccggauuc 720
cggcugaggc cggucgccgg auugcucucc ucccgggauu uccucggcgg acuggcauuc 780
cggguguucc acugcaccca guacaucaga cacgguagca agccgaugua caccccggaa 840
cccgacaucu gccaugaacu ccugggacac gugcccuugu ucuccgaccg cuccuucgcg 900
caauucuccc aagaaaucgg acuggcuucc cugggugcac cugaugaaua cauugaaaag 960
cucgccacaa uuuacugguu uacuguggag uuugggcucu gcaaacaagg agacuccaua 1020
aaggcauaug gugcugggcu ccugucaucc uuuggugaau uacaguacug cuuaucagag 1080
aagccaaagc uucuccccu ggagcuggag aagacagcca uccaaaauua cacugucacg 1140

-continued

```
gaguuccagc cccucuauua cguggcagag aguuuuaaug augccaagga gaaaguaagg   1200

aacuuugcug ccacaauacc ucggcccuuc ucaguucgcu acgacccaua cacccaaagg   1260

auugaggucu uggacaauac ccagcagcuu aagauuuugg cugauuccau uaacagugaa   1320

auuggaaucc uuugcagugc ccuccagaaa auaaaguaa                          1359
```

<210> SEQ ID NO 22
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 22

```
augagcaccg ccguccuuga aaacccuggc cuuggaagaa agcugaguga cuucggacag     60

gaaacuucgu auaucgagga caacugcaac cagaacgggg ccauuagccu gaucuuuuca    120

cugaaagagg aggucggagc ucuggccaag guccuucggc uguucgagga aaaugacgug    180

aaccugacac acaucgaauc ccggccgucg cggcugaaga aggaugaaua cgaguucuuc    240

acgcaucugg acaagcgguc ccugccggcc uugaccaaca ucauaaagau ucugcggcac    300

gauaucgggg caaccgugca ugagcugagc cgggacaaga agaaggacac cgugccgugg    360

uuuccccgga caauccagga gcuggaccgc uucgccaauc aaauccugag cuacggugca    420

gaacuggacg cggaccaccc aggguucaag gacccggugu acagagccag gagaaagcag    480

uucgccgaua uugcauacaa cuaccgccac ggccagccga uuccccgcgu ggaguacaug    540

gaagaagaga agaaaaccug ggggacugug uucaagacuc ugaagucccu guauaagacc    600

cacgcguguu augaguacaa ccauauuuuc ccgcugcugg aaaaguauug cggauuccau    660

gaggauaaca uuccgcagcu ggaggacgug ucacaguuuc ugcaaacuug caccggauuc    720

cggcugaggc cggucgccgg auugcucucc ucccgggauu ucccucggcgg acuggcauuc  780

cggguguucc acugcaccca guacaucaga cacgguagca agccgaugua cacccccggaa  840

cccgacaucu gccaugaacu ccugggacac gugcccuugu ucuccgaccg cuccuucgcg    900

caauucuccc aagaaaucgg acuggcuucc cugggugcac cugaugaaua cauugaaaag    960

cucgccacaa uuuacugguu uacuguggag uuugggcucu gcaaacaagg agacuccaua   1020

aaggcauaug gugcugggcu ccugucaucc uuuggugaau uacaguacug cuuaucagag   1080

aagccaaagc uucuccccccu ggagcuggag aagacagcca uccaaaauua cacugucacg  1140

gaguuccagc cccucuauua cguggcagag aguuuuaaug augccaagga gaaaguaagg   1200

aacuuugcug ccacaauacc ucggcccuuc ucaguucgcu acgacccaua cacccaaagg   1260

auugaggucu uggacaauac ccagcagcuu aagauuuugg cugauuccau uaacagugaa   1320

auuggaaucc uuugcagugc ccuccagaaa auaaaguaa                          1359
```

<210> SEQ ID NO 23
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 23

```
augucaacug cuguguuaga aaacccugga cucggacgca aacucucgga cuucggacag     60

gaaaccuccu auaucgagga uaacugcaac cagaauggag ccaucucacu gaucuucucg    120

cugaaagaag aggucggagc ccuggcuaag guccugagac uguuugagga gaacgaugug    180
```

-continued

```
aaccuuacuc acaucgaauc gcggcccagc agacugaaga aggaugagua cgaguucuuc    240
acccaccugg auaagcgcuc acugccggca cucacaaaca uuaucaagau ucugagacac    300
gacaucggcg caaccgucca ugagcugagc cgcgacaaga agaaggacac ugucccaugg    360
uuuccccgga ccauccaaga gcuggaccgc uucgcaaacc agauccuguc cuacggcgcg    420
gaacuggacg ccgaucaccc ggggguucaag gacccggugu acagagcacg ccgcaagcag    480
uucgccgaua uugccuacaa cuaucggcau gggcagccga ucccuagggu ggaguacaug    540
gaagaggaaa agaaaaccug gggcaccgug uuuaagacuc ucaagucacu guacaagacc    600
cacgccugcu acgaguacaa ccacaucuuc ccgcuccuug aaaaguacug cggguuucac    660
gaggauaaca ucccgcaacu ggaggacgug ucacaguucc uucaaaccug uaccggauuc    720
cggcugcgcc cgguggccgg acucuuguca ucccgggacu uccuuggggg gcuggcguuc    780
cgaguguucc auuguaccca guacauucgg cauggcucaa agcccaugua caccccggaa    840
ccagacaucu gccacgaguu gcucggccac gugccguugu ucuccgaccg gagcuucgcg    900
caguucagcc aggaaauugg ccuggcaucg cugggugcac cggacgagua caucgaaaag    960
cucgcuacga ucuauugguu cacuguggag uucgggcugu gcaaacaggg agacucuauc   1020
aaggcuuacg gggcgggacu gcugucguca uucggcgaau ugcaguacug ccuguccgag   1080
aagccgaagc uccugccgcu ggaacuggaa aagaccgcga uucaaaacua cacugugacc   1140
gaauuccagc cccucuacua cguggccgaa agcuucaaug acgcgaagga aaaaguccgg   1200
aacuucgccg ccaccauccc gaggcccuuc uccgugcgcu acgacccgua cacccagcgc   1260
auugaggugc uagacaacac ccagcagcug aagauucugg cagacuccau aaacucggag   1320
aucgggauuc ugugcucggc acugcaaaag aucaaguaa                          1359
```

<210> SEQ ID NO 24
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 24

```
augucaacug cagugcucga aaaccccggu cuaggacgaa agcucuccga cuucggacaa     60
gaaaccucgu acaucgagga caauugcaac cagaacggag ccauuucauu gauuuucucg    120
cugaaagaag aagucggggc ucucgcgaaa gugcugaggc uguucgaaga gaacgacgug    180
aacuugaccc acauugaaag cagacccagc cgccugaaga aggacgaaua cgaguucuuc    240
acccaucugg auaagcgguc acuuccggcc cucaccaaca ucaucaagau cuuacgccau    300
gauauugggg caaccgugca cgagcugucg agggauaaga agaaggacac cgucccgugg    360
uuuccgcgga ccauacagga acuggaccgg uucgcaaacc aaauucuguc auacggggcg    420
gaacuggacg cggaccaucc cggguucaag gacccggugu accgggccag gagaaagcag    480
uucgccgaua ucgcguacaa uuaccgccac gggcagccga uuccgcgcgu ggaguacaug    540
gaggaagaga agaaaaccug ggggaccgug uucaagacac ugaagucgcu cuacaagacu    600
cacgccugcu acgaguacaa ccacaucuuc ccgcugcugg aaaaguacug cggguuucac    660
gaagauaaca ucccgcagcu ggaggacgug ucgcaguucc ugcaaacuug caccggauuc    720
cggcugcggc cgguggcggg gcuccugucc ucccgcgauu uucuuggcgg gcuggcuuuc    780
cggguguucc acugcaccca guauaucaga cacgggucca agccgaugua cacuccggag    840
ccggacaucu gucaugagcu guugggccac gucccgcugu ucuccgaccg gagcuuugcc    900
```

-continued

```
caguucucac aagaaaucgg acuggcauca cugggggcac ccgaugagua cauugagaag    960

cuugccacca ucuacugguu caccguggaa uucgggcugu guaaacaggg ggacucgauu   1020

aaggcauacg gggccggacu gcucucgucc uucggggaac ugcaauacug ccucucugaa   1080

aagcccaagc uccugccgcu ggagcuggaa aagacugcaa uccagaacua uaccgugacu   1140

gaguuccagc cgcucuacua cgucgcggag uccuucaacg acgcuaagga gaagguccgc   1200

aacuucgcug caaccauccc gcggccguuc agcgugcgcu acgacccgua uacgcagcgc   1260

aucgaggugc uggacaacac ucagcagcug aagauccugg ccgauucaau caacucagaa   1320

aucgggaucc ugugcucggc ccuccaaaag auuaaguaa                          1359
```

<210> SEQ ID NO 25
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 25

```
augucaaccg cugugcuuga aaaucccgga cucggccgca aguuauccga uuuuggacaa     60

gaaaccucau acauugagga caacugcaac cagaacggcg cgaucucacu gaucuucucg    120

cugaaagagg aagucggagc auuggccaag guccugaggc uguucgagga aaacgacgug    180

aaccugaccc acauagaauc gcggccguca cggcuaaaga aggaugaaua cgaguucuuc    240

acccaccugg acaagcgguc gcugccggcg cugacuaaca ucaucaagau ucugcggcac    300

gauaucgggg caaccgugca ugagcugagc cgggacaaga agaaggacac cgugccgugg    360

uucccccgga cuauccagga gcuggaccgc uucgcgaacc aaauccugag cuacggugca    420

gaacuggacg cggaccaccc aggguucaag gacccggugu acagagccag gagaaagcag    480

uucgccgaca uugcauacaa cuaccgccac ggccagccga uuccccgcgu ggaguacaug    540

gaagaagaga agaaaaccug ggaacugug uucaagacuc ugaagucccu guauaagacc    600

cacgccuguu augaguacaa ccauauuuuc ccgcugcugg aaaaguauug cggauuccau    660

gaggauaaca uuccgcagcu ggaggacgug ucacaguuuc ugcaaacuug caccggauuc    720

cggcugaggc cggucgccgg auuguugucc ucccgggauu uccucggcgg acuggcauuc    780

agaguguucc acugcaccca guacauuaga cacgggucga agccgaugua caccccugag    840

ccugacaucu gccaugaacu gcuuggccac gucccguugu uuucggaccg cucauucgca    900

caauucagcc aggagauugg acucgcauca cuuggagccc ccgaugagua caucgagaag    960

cucgccacca ucuacugguu caccguggag uucggccugu gcaaacaggg ggauagcauc   1020

aaagcuuacg gcgcgggccu ccuguccuca uucggggaac uccaguacug ucucuccgaa   1080

aagccgaagc ugcugccccu ugaacucgaa aagaccgcaa uccagaacua caccgugacu   1140

gaauuucagc cgcucuacua cguggccgaa agcuucaacg acgcuaagga aaagguccgc   1200

aacuucgccg cgacuauccc gcgaccguuc uccgugcgcu acgacccaua cacucagcgc   1260

aucgaggugc uggacaauac ccagcagcuc aagauccugg cugacuccau caacucggag   1320

auugggaucc ugugcuccgc ccugcaaaag aucaaguaa                          1359
```

<210> SEQ ID NO 26
<211> LENGTH: 1359
<212> TYPE: RNA
<213> ORGANISM: Artificial Sequence
<220> FEATURE:
<223> OTHER INFORMATION: Codon-Optimized PAH Coding Sequence -continued

<400> SEQUENCE: 26
augucaacug cugugcucga aaaucccggc uuaggaagga agcucucaga cuucggacaa 60
gaaaccuccu acauugagga caacugcaau cagaacggcg caaucucccu gaucuucucg 120
cugaaagaag aagucggcgc acuugccaag guccugagac ucuucgagga aaacgacgug 180
aaccucaccc acaucgaguc acgcccgucg agauugaaga aggaugagua cgaguucuuc 240
acccaucuug auaagcgguc gcugcccgca cuuaccaaca uuaucaagau ccugcggcau 300
gacauuggag caaccgugca cgaacugucc cgcgacaaga agaaagauac cgugccgugg 360
uucccgagaa ccauucagga gcuggaccgg uucgccaacc aaauccuguc cuacggggcc 420
gaacuggaug ccgaucaccc gggguucaag gacccggucu accgcgcgcg gcgcaagcag 480
uuugcugaua uugccuacaa cuaccgccac ggccagccga ucccgcgagu ggaguacaug 540
gaagaagaga agaaaaccug ggcacugugu uucaagaccc ugaagucgcu cuauaagacg 600
cacgccugcu acgaguacaa ccacaucuuc ccgcuccugg agaaguacug cggguuucac 660
gaggauaaca ucccgcaacu ggaggacguc agccaguucc ugcaaaccug uaccggauuc 720
aggcugaggc cgguggccgg acugcucuca ucacgcgacu uccugggggg ccucgcguuc 780
cggguguucc auugcacaca guacauuaga cacgggucga agccgaugua cacccccgag 840
ccggacaucu gccacgagcu gcugggacau gugccgcugu ucuccgaccg gagcuucgcu 900
caguucagcc aggaaaucgg gcuggcgucg cucggagcac cggaugagua cauagagaag 960
cuggcuacua ucuacugguu caccguggag uucggccugu gcaaacaggg ggacucaauc 1020
aaggcguacg gagccgguuu gcugagcuca uucggagaac uacaguauug ucuguccgaa 1080
aagccgaagc uucugccgcu ggaacuggaa aagaccgcaa uccagaacua uaccgugacu 1140
gaguuccagc cccuguacua cguggcagaa uccuucaacg acgccaagga gaagguccgc 1200
aacuuugccg cgacuauccc ccggccguuc ucugugcgcu acgacccgua cacucagcgg 1260
aucgaagugu uggacaacac ccagcaguug aagauucugg cagacagcau caacucggaa 1320
auugggauuc ugugcuccgc gcuccaaaag aucaaguaa 1359

<210> SEQ ID NO 27
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 27
augucaaccg ccgugcucga aaauccagga uugggaagaa aacucucaga cuucggccag 60
gaaaccucgu acauugagga uaacuguaac cagaacggcg cgaucucgcu gaucuuuagc 120
cugaaggagg aagucggagc acuggccaag guccugaggc uguucgaaga gaacgacgug 180
aaccugacuc auauugaaag ccgcccguca cgccugaaga aagaugagua ugaguucuuc 240
acccaccugg acaagcgcag ccugccggcc cucacuaaca ucaucaagau ccuaagacac 300
gauauuggag cgaccgucca cgaauuguca agggacaaga agaaggacac ugucccgugg 360
uucccgagaa ccauucagga gcucgaccgg uucgcaaacc aaaucuuauc cuacggagcu 420
gaacuggacg cagaccaccc gggguucaag gaccccgugu accgggcgcg caggaagcag 480
uucgcugaca ucgcauacaa cuaccgccac gggcagccga uaccgcgcgu ggaguauaug 540
gaagaagaga agaaaaccug gggacggug uucaagacuc ugaaguccu cuacaaaacc 600 cacgccugcu acgaguacaa ccauauuuuu ccgcuccugg aaaaguacug cggcuuccau 660
gaggacaaca ucccacagcu ggaagaugug ucacaguuuc ugcaaacuug uaccggcuuc 720
cggcugcggc caguggcagg ccugcucucc ucccgcgauu uccucggcgg ucuggcguuc 780
cggguguucc acugcaccca guacaucaga cauggaucga agccgaugua cacucccgaa 840
ccugacaucu gccacgagcu guugggacau gugcccuugu ucucggaucg gagcuucgcg 900
caguucucac aagagauugg ccuugcguca cugggagcac cggacgagua caucgagaag 960
cucgcaacca ucuacugguu caccgucgaa uucggccugu gcaagcaggg agacucgauu 1020
aaggccuacg gggccggacu gcugucgucc uucggggagc ugcaguacug ccuguccgaa 1080
aagccgaagc uucugcccu ggaauuggaa aagacagcca uccagaacua caccgugacc 1140
gaauuccagc cccucuacua cguggcugaa uccuucaacg acgccaagga gaagguccgc 1200
aacuuugcug cgaccauccc gcggccuuuc uccgugcgau acgauccgua uacccagcgg 1260
aucgaggugc uggacaacac ccagcaacuu aagauccugg ccgacuccau caauagcgag 1320
auuggaaucc ugugcagcgc ccugcaaaag aucaaguaa 1359

<210> SEQ ID NO 28
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 28
augucaaccg ccguccuuga aaaccccggc cucggaagaa agcucucaga cuuuggacag 60
gaaacuuccu acauugagga uaacugcaac cagaacggug caaucagccu gaucuucucg 120
cugaaagagg aagucggggc acuggcaaag guccugcgcc uguucgagga aaaugaugug 180
aaccugacuc auaucgaguc acggccgucg cgccucaaga aggacgaaua cgaguucuuc 240
acccaccuug acaagagauc ccuuccggca cugacuaaca ucaucaagau uuugcggcac 300
gacauugggg ccaccgugca cgaacugucu agggacaaaa agaaggauac ugucccgugg 360
uucccgcgga cuauucagga acuggaccgc uucgcgaacc aaauucugag cuacggggcu 420
gaacuagaug cggaccaccc gggcuuuaag gauccggugu accgcgcacg gcgaaagcaa 480
uucgccgaua uugccuauaa cuaccgccac ggacagccga ucccacgcgu ggaguacaug 540
gaggaagaga aaaagaccug ggcaccgug uucaagaccc ugaagucgcu guacaagacc 600
cacgcaugcu acgaguacaa ccacaucuuc ccgcugcugg aaaaguacug cggguuccac 660
gaggacaaca uuccgcaacu ggaggacgug ucccaguuuc uccaaaccug uaccggguuc 720
agacugaggc ccguggcugg acugcugucg ucccgggacu uccugggggg ccucgccuuc 780
cgcguguucc auugcacuca guacauccgc cacgggucaa agccgaugua caccccugag 840
cccgauaucu gucaugaguu gcugggccau gugccucucu ucuccgaucg gucguucgcg 900
caguuuagcc aggaaauugg guuggcuucg cucggagccc cagacgagua caucgagaag 960
cuggcuacga ucuacugguu caccguggag uucggccugu gcaaacaggg agacuccaua 1020
aaggccuaug gcgcgggacu ccuguccuca uucggagagc ugcaguacug cuuauccgag 1080
aagcccaagc uccucccgcu ugaacuggaa aagaccgcaa uccagaacua caccgugacg 1140
gaguuccagc cgcuguauua cguggccgaa ucguucaacg acgcaaagga aaagguccgc 1200
aauuucgcgg cgacaauccc gcggccguuc ucagugcgcu acgacccgua cacucagcgg 1260
aucgaagugc uggacaacac ccagcaacuu aagauccugg ccgacucaau caacuccgaa 1320
aucggaaucc ugugcagcgc acugcagaag auuaaguaa 1359

-continued

<210> SEQ ID NO 29
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 29
augucaaccg cugugcuuga aaaccccgga cucggccgca aguuaucuga uuucggacaa 60
gaaacuucau acauugagga caacugcaac cagaacgggg cgauuucacu gaucuucucg 120
cugaaagaag aagucggagc auuggcgaag guccugaggc uguucgagga aaacgacgug 180
aaccugaccc acauagaauc gcggccguca cggcuaaaga aggaugaaua cgaguucuuc 240
acgcaccugg acaagcgguc gcugccggcg cugaccaaca ucaucaagau ucugcggcac 300
gauaucgggg caaccgugca ugagcugagc cgggacaaga agaaggacac cgugccuugg 360
uuuccccgga caauccagga gcuggaccgc uucgccaauc aaauccugag cuacggugca 420
gaacuggacg cggaccaccc aggguucaag gacccggugu acagagccag gagaaagcag 480
uucgccgaua uugcauacaa cuaccgccac ggccagccga uuccccgcgu ggaguacaug 540
gaagaagaga agaaaaccug ggggaccgug uucaagacuc ugaagucccu guauaagacc 600
cacgcguguu augaguacaa ccauaucuuc ccgcugcugg aaaaguauug cggauuccau 660
gaggauaaca uuccgcagcu ggaggacgug ucacaguuuc ugcaaacuug caccggauuc 720
cggcugaggc cggucgccgg auugcucucc ucccgggauu ucccucggcgg acuggcauuc 780 agaguguucc acugcaccca guacauuaga cacgggucga agccgaugua caccccugag 840
ccugacaucu gccaugaacu gcuuggccac gucccguugu uuucggaccg cucauucgca 900
caauucagcc aggagauugg acucgcauca cuuggagccc ccgaugagua caucgagaag 960
cucgccacca ucuacugguu cacuguggag uucggccugu gcaaacaggg ggauuccauc 1020
aaagcuuacg gcgcgggccu ccuguccuca uucggggagu ugcaguacug ucucuccgaa 1080
aagccgaagc ugcugccccu ugaacucgaa aagaccgcaa uccagaacua caccgugacu 1140
gaauuucagc cgcucuacua cguggccgag agcuucaacg acgcuaagga aaagguccgc 1200
aacuucgccg ccacuauccc acgaccguuc uccgugcgcu acgacccaua cacucagcgc 1260
aucgaggugc uggacaauac ccagcagcuc aagauccugg cugacuccau caacucggag 1320
auugggaucc ugugcucggc ccugcaaaag aucaaguaa 1359

<210> SEQ ID NO 30
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 30
augucaaccg cugugcuuga aaaccccgga cucggccgca agcuuucuga uuucggacaa 60
gaaaccucau acauugagga caacugcaac cagaacgggg cgaucucacu gaucuucucg 120
cugaaagaag aagucggagc auuggcgaag guccugaggc uguucgagga aaacgacgug 180
aaccugaccc acauagaauc gcgcccguca cggcuaaaga aggaugaaua cgaguucuuc 240
acgcaccugg acaagagauc acugccggcg cugacuaaca ucaucaagau ucugcggcac 300
gauauugggg caaccgugca ugagcugagc cgggacaaga agaaggacac cgugccgugg 360
uuuccccgga caauccagga gcuggaucgg uucgccaauc aaauccugag cuacggugca 420
gaacuggacg cggaccaccc aggguucaag gacccggugu accgggccag gagaaagcag 480
uucgccgaua ucgcauacaa cuaccgccac ggccagccga uuccccgcgu ggaguacaug 540
gaagaagaga agaaaaccug gggacugug uucaagacuc ugaagucgcu guauaagacc 600
cacgcguguu augaguacaa ccacauuuuc ccgcugcugg aaaaguauug cggauuccau 660
gaggauaaca uuccgcagcu ggaggacgug ucacaguuuc ugcaaacuug caccggauuc 720
cggcugaggc cggucgccgg auugcugucc ucccgggauu ucccucggcgg acuggcauuc 780 agaguguucc auugcaccca guacauuaga cacgggucga agccgaugua caccccugag 840
ccugacaucu gccaugaacu gcuuggccac gucccguugu uuucggaccg cucauucgca 900
caauucagcc aggagauugg acuggcaucc cuuggagccc ccgacgagua caucgagaag 960
cuggccacca ucuacugguu caccguggag uucggccugu gcaaacaggg ggauuccauc 1020
aaagcuuacg gcgcgggccu ccuuuccuca uucggggaau ugcaguacug ucuguccgaa 1080
aagccgaagc ugcugccccu ugaacucgaa aagaccgcaa uccagaacua caccgugacu 1140
gaauuucagc cgcucuacua cguggccgag agcuucaacg acgcuaagga aaagguccgc 1200
aacuucgccg ccacuauccc gcgaccguuc uccgugcgcu acgacccaua cacucagcgc 1260
aucgaggugc uggacaauac ccagcagcug aagauccugg cugacuccau caacucggag 1320
auugggaucc ugugcucggc ccugcaaaag aucaaguaa 1359

<210> SEQ ID NO 31
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 31
augucaaccg cugugcuuga aaaccccgga cucggccgca aguuaucuga uuucggacaa 60
gaaaccucau acaucgagga caacugcaac cagaacgggg cgaucucacu gaucuucucg 120
cugaaagaag aagucggagc auuggcgaag guccugaggc uguucgagga aaacgacgug 180
aaccugaccc acauagaauc gcggccguca cggcuaaaga aggaugaaua cgaguucuuc 240
acgcaccugg acaagcgguc gcugccggcg cugacuaaca ucaucaagau ucuccggcac 300
gauaucgggg caaccgugca ugagcugagc cgggacaaga agaaggauac cgugccgugg 360
uuuccccgga caauucagga acuggaccgc uucgccaauc aaauccugag cuacggugca 420
gaacuggacg cggaccaccc aggguucaag gacccggugu acagagccag gagaaagcag 480
uucgccgaca uugcauacaa cuaccgccac gggcagccga uuccccgcgu ggaguacaug 540
gaggaagaga agaaaaccug gggacugug uucaagacuc ugaagucccu guauaagacc 600
caugcguguu augaguacaa ccacauuuuc ccgcugcugg aaaaguauug cggguuccau 660
gaggauaaca uuccgcagcu ggaggacgug ucacaguuuc ugcaaacuug caccggguuc 720
cggcugaggc cggucgccgg auugcucucc ucccgggauu uccucggggg gcuggcauuc 780
agaguguucc acugcaccca guacauuaga cacgggucga agccgaugua caccccugag 840
ccugacaucu gccaugaacu gcuuggccac gucccguugu uuucggaccg cucauucgca 900
caauucagcc aggagauugg acucgcauca cuuggagccc ccgaugagua caucgagaag 960
cucgccacca ucuacugguu caccguggag uucgggcugu gcaaacaggg ggauuccauc 1020
aaagcuuacg gcgcggggcu ccuguccuca uucggggaau ugcaguacug ucucuccgaa 1080
aagccgaagc ugcugccccu ugaacucgaa aagaccgcaa uccagaacua caccgugacu 1140

-continued gaguuucagc cgcucuacua cguggccgag agcuucaacg acgcuaagga aaagguccgc 1200
aacuucgccg ccacuauccc gcgaccguuc uccgugcgcu acgacccaua cacucagcgc 1260
aucgaagugc uggacaauac ccagcagcuc aagauccugg cugacuccau caacucggag 1320
auugggaucc ugugcucggc ccugcaaaag aucaaguaa 1359

<210> SEQ ID NO 32
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 32
augucaacug cugugcucga aaacccaggc cuuggaagga agcugucaga cuucggacaa 60
gaaaccuccu acauugagga caacuguaac cagaacggcg ccaucucccu cauuuucuca 120
cugaaagagg aagucggggc gcuggcgaag guccugagac uguuugaaga aaacgacgug 180
aaccugaccc acauugaguc ccgaccuucg cgccucaaga aggacgaaua cgaauucuuc 240
acccaucugg acaagcgcuc ccugccggca cuuaccaaua ucaucaagau ccugcggcau 300
gauaucggcg cuaccgugca ugagcugucu cgggauaaga agaaggacac cgugcccugg 360
uucccgagaa ccauccagga acuugaucgg uucgccaacc aaauucuguc cuacggggcc 420
gaacuggaug cagaucaccc ggguuucaag gacccugugu accgggcccg gcggaagcaa 480
uucgccgaca uugcauacaa cuauagacau ggacagccca uuccgagggu ggaguacaug 540
gaggaggaga aaaagacuug ggaacugug uucaagaccc ugaagucguu guauaagacu 600
cacgcuugcu acgaguacaa ccacaucuuc ccgcugcugg agaaguacug cggguuccac 660
gaggacaaca uuccgcaacu ugaggacguc agccaguucc ugcaaaccug uacuggauuc 720
cgccugcgcc cgguggccgg ccugcuguca ucacgggacu uccugggagg ccucgcguuc 780
cgcguguucc acugcaccca guacaucaga cacggaucca agccgaugua cacccccgaa 840
ccggauauuu gccacgaguu gcugggccac gugccacugu uuagcgaccg cagcuucgca 900
caguucagcc aggaaaucgg gcuggcuucc cuuggcgccc cggaugagua caucgaaaag 960
cuugcaacca ucuacugguu cacugucgaa uucgggcugu gcaaacaggg ggacucaauc 1020
aaggcauacg gggcgggauu gcucucgucg uuuggcgaac ugcaguacug ccuuucggaa 1080
aagcccaagu ugcugccccu ggaacuggag aaaaccgcaa uccagaacua uacugugacc 1140
gaauuccagc cacuguacua cguggccgag ucauucaacg acgcgaagga gaaaguccgc 1200
aauuucgcug cgacuauccc gcggccguuc uccgugcgcu acgacccgua cacccagcgc 1260
auagaggugc uggauaacac ccagcagcua aagauccugg ccgacucgau caacucggaa 1320
aucggaaucc ugugcagcgc acugcagaag auuaaguaa 1359

<210> SEQ ID NO 33
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 33
augucaaccg cugugcuuga aaaccccgga cucggccgca aguuaucuga uuucggacaa 60
gaaaccuccu acaucgagga caacugcaac cagaacgggg cgauuucacu gaucuucucg 120
cugaaagaag aagucggggc auuggcgaag guccugaggc uguucgagga aaacgacgug 180

-continued

```
aaccugaccc acauagaauc gcggccguca cggcuaaaga aggaugaaua cgaguucuuc    240

acgcaccugg acaagcgguc gcugccggca cugacuaaca ucaucaagau ucugcggcau    300

gauaucgggg ccaccgugca ugagcugagc cgggacaaga agaaggacac cgugccgugg    360

uuuccccgga caauccagga acuggaccgc uucgccaauc aaauccugag cuacggugca    420

gaacuggacg cggaccaccc gggguucaag gacccggugu accgggccag gagaaagcag    480

uucgccgaua uugcauacaa cuaccgccac gggcagccga uuccccgcgu ggaguacaug    540

gaagaagaga agaaaaccug ggggacugug uucaagaccc ugaagucccu guauaagacc    600

cacgcguguu augaguacaa ccacauuuuc ccgcugcugg aaaaguauug cggauuccau    660

gaggauaaca uuccgcaacu ggaggaugug ucacaguucc ugcaaacuug cacuggauuc    720

agacugaggc cggucgccgg gcugcucuca ucccgggacu ucucgggggg gcuggcauuc    780

agaguguucc acugcaccca guacauuaga cacgggucga agccgaugua caccccggag    840

ccggacaucu gccaugaguu gcuuggccac gucccguugu uuucggaccg cucauucgcc    900

caauucagcc aggagauugg gcucgcguca cuuggagcac ccgaugagua caucgagaag    960

cucgccacca ucuacugguu caccguggag uucgggcugu gcaaacaggg ggauuccauc   1020

aaagcuuacg gcgcgggacu ccuguccuca uucggggagu ugcaguacug ucucuccgaa   1080

aagccgaagc ugcugccccu ugaacucgaa aagaccgcaa uccagaacua caccgugacu   1140

gaauuucagc cgcucuacua cguggccgag agcuucaacg acgcuaagga gaagguccgc   1200

aacuucgccg caacuauccc gcgaccguuu uccgugcgcu acgacccgua cacucagcgc   1260

aucgaagugc uggacaauac gcagcagcuc aagauccugg cugacuccau caacucggag   1320

auugggaucc ugugcucggc ccugcaaaag aucaaguaa                          1359
```

<210> SEQ ID NO 34
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 34

```
augucaaccg cugugcuuga aaacccugga cucggccgca agcuuuccga uuuuggacaa     60

gaaaccucau acauugagga caacugcaac cagaacgggg cgaucucacu gaucuucucg    120

cugaaagaag aggucggagc acuggcgaaa guccugaggc uguucgagga aaacgacgug    180

aaccugaccc acauagaauc acggccgucg cggcuaaaga aggaugaaua cgaguucuuc    240

acccaccugg acaagcgguc ccugccggcc cuuacuaaca ucaucaagau ucugcggcac    300

gauaucgggg caaccgugca ugagcugagc cgggacaaga agaaggacac cgugccgugg    360

uuuccccgga cuauccagga guuggaccgc uucgccaauc aaauccugag cuacggugca    420

gaacuggacg cggaccaccc aggguucaag gacccagugu auagagccag gagaaagcag    480

uucgccgaua uugcauacaa cuaccgccac ggccagccga uuccccgcgu ggaguacaug    540

gaagaggaga agaaaaccug ggggacugug uucaagacuc ugaagucccu guauaagacc    600

cacgcguguu acgaguacaa ccauaucuuc ccgcugcugg aaaaguacug cggauuccau    660

gaggauaaca uuccgcagcu ggaggacgug ucacaguucc ugcaaacuug caccggauuc    720

cggcugaggc cggucgccgg auugcugucc ucccgggauu ucucggcgg acuggcauuc    780

agaguguucc acugcaccca guacauuaga cacgggucga agccgaugua caccccugag    840

ccugacaucu gccaugaacu gcuuggccac gucccguugu uuucggaccg cucauucgca    900
```

-continued caauucagcc aggagauugg gcucgcauca cuuggagcac ccgaugagua caucgagaag 960
cucgccacca ucuacugguu caccguggag uucggccugu gcaaacaggg ggauuccauc 1020
aaggcuuacg gcgcgggccu gcuguccuca uucggggaac ugcaguacug ucuguccgaa 1080
aagccgaagu ugcugccccu ugaacucgaa aagaccgcaa uccagaacua caccgugacu 1140
gaauuucagc cgcuuuacua cguggccgag agcuucaacg acgcuaagga aaagguccgc 1200
aacuucgccg cgacuauccc ccgaccguuc uccgugcgcu augacccaua cacucagcgc 1260
aucgaggugc uggacaauac ccagcagcug aagauccugg cugacucgau caacuccgag 1320
aucggaaucc ugugcagcgc ccugcaaaag auuaaguaa 1359

<210> SEQ ID NO 35
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 35
auguccaccg ccgugcuuga aaauccuggg uuggguagaa aacugucaga uuuuggccaa 60
gaaaccucau acaucgaaga uaacugcaac cagaauggag cuaucucccu gauauucucg 120
cugaaagagg aagucggcgc ccuggccaaa guucugagac ucuucgagga aaacgacguu 180
aaccugacuc acauugaauc ccggcccucc cgacugaaga aggaugaaua cgaauucuuc 240
acucaccugg acaagagguc ccugccggcc cugaccaaca ucauuaagau ccugcggcac 300
gacaucgggg ccaccgugca cgaacugagc agggacaaga agaaggauac cgugcccugg 360
uuuccgcgca cuauucaaga acuggacaga uuugccaacc aaauucuguc cuacggggcc 420
gaacuggacg ccgaucaccc cggguuuaag gaccccgugu accgggcccg gcgcaagcag 480
uuugcggaca ucgcuuauaa cuaucggcau ggccagccga ucccccgugu ggaguacaug 540
gaagaggaga aaaagacuug gggcaccgua uucaagaccc uaaagagccu guauaagacc 600
caugccuguu acgaguacaa ccacaucuuc ccguugcugg aaaaguacug uggauuucac 660
gaggauaaca uaccccagcu ugaggacguc agccaguucc ugcaaacuug uaccggguuc 720
aggcugaggc cgguugccgg gcugcugagc ucacgggacu uccugggagg ucuggcauuc 780
cggguguucc auugcaccca guacaucaga caugggucca agcccaugua uaccccggaa 840
ccggauaucu gucacgagcu gcuuggacau gugccgcuuu ucuccgaccg aagcuucgcc 900
caguucagcc aagaaauagg gcucgccagu cugggcgccc cggaugagua caucgaaaag 960
uuggcgacca ucuacugguu cacuguagag uucggccuuu gcaaacaagg ggacagcauc 1020
aaggcauacg gggccgguuu guugucgagc uucggggagc ugcaguauug ucuguccgaa 1080
aagccgaaac uccugccgcu ggaguuggaa aagacagcua uucagaacua uacagugaca 1140
gaauuucagc ccuguacua cguggcagaa uccuucaacg acgcgaagga gaaaguccgg 1200
aauuuugccg cuaccauucc gcgcccguuu uccgugcgcu acgacccgua cacucagaga 1260
auugaggugc uggacaauac ccagcagcuu aagauucugg cggacucaau caacagcgag 1320
auuggcaucc ugugcuccgc acugcaaaag aucaaguaa 1359

<210> SEQ ID NO 36
<211> LENGTH: 1359
<212> TYPE: RNA
<213> ORGANISM: Artificial Sequence
<220> FEATURE:
<223> OTHER INFORMATION: Codon-Optimized PAH Coding Sequence -continued

<400> SEQUENCE: 36

```
augucaacug cugugcucga aaaccccggc cuaggaagaa aacugucaga uuucggccaa     60
gagacuuccu acauugagga caacugcaau cagaacggag caaucucccu gaucuucuca    120
cugaaagagg aagucggggc acuugccaag guccuccgcc uguuugagga aaacgacgug    180
aacuugaccc acaucgaguc gcgcccgucg cgccugaaga aggacgaaua cgaauucuuc    240
acccaccugg acaagcgguc acucccggcg cugaccaaca uaaucaagau ccuucggcac    300
gacauuggag ccaccgugca cgaauugucg cgggacaaga agaaggacac cgugccgugg    360
uucccgagga ccauucagga gcuggaccgg uucgcaaacc agauccucuc cuacggggca    420
gaacuggaug ccgaucaccc gggcuucaag gaccccgugu accgggccag gcgcaagcag    480
uucgccgaca uugccuacaa cuaccgccac gggcagccga uuccgagggu ggaguauaug    540
gaagaggaaa agaaaaccug gggaccgug uucaagaccc uuaagucacu guacaagacu     600
caugccugcu acgaguacaa ccacaucuuc ccgcugcugg agaaguauug cggguuucau    660
gaggacaaua ucccgcaacu ugaggacguc agccaguucc ugcaaacuug caccggguuc    720
agacugcggc cgguggcagg acugcugucc ucgcgggacu uccugggggg ccuggcguuc    780
cgcguguucc acugcaccca guacauuaga cacgguucca agccgaugua caccccggaa    840
ccggacaucu gccaugaacu guugggacac gugccccugu uuuccgaucg gucguucgca    900
caauucagcc aggaaaucgg gcucgccuca cugggggccc cggaugagua caucgagaag    960
cuggcgacca ucuacugguu uacugucgaa uucggccugu guaaacaggg ggauucgauc   1020
aaggcguacg gggccggccu gcugucguca uucggagagc ugcaguacug ucugagcgag   1080
aagccgaagc uccuuccccu ugaacuggaa aagaccgcaa uccagaacua caccgugacu   1140
gaauuccaac cgcuguacua uguggcugag uccuucaacg acgcgaagga aaaaguccga   1200
aacuucgcgg cgacuauccc ccggcccuuc uccgugcgcu acgacccgua cacucagcgc   1260
auugaagugc ucgacaacac ccagcagcug aagauccugg ccgauucaau caacuccgaa   1320
auuggaaucc ugugcagcgc auugcagaag auuaaguaa                          1359
```

<210> SEQ ID NO 37
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 37

```
auguccaccg ccgugcugga gaaccccggc uugggcagga agcuguccga cuucggccag     60
gagaccagcu acaucgagga caacugcaac cagaacggcg ccaucucccu gaucuucucc    120
cugaaggagg aggugggcgc cuuggccaag guguugcggu uguucgagga gaacgacgug    180
aaccugaccc acaucgaguc caggcccucc cgguugaaga aggacgagua cgaguucuuc    240
acccacuugg acaagcggag ccugcccgcc cugaccaaca ucaucaagau cuugaggcac    300
gacaucggcg ccaccgugca cgagcugucc cgggacaaga agaaggacac cgugcccugg    360
uuccccagga ccauccagga gcuggacagg uucgccaacc agauccugag cuacggcgcc    420
gagcuggacg ccgaccaccc cggcuucaag gaccccgugu accgggccag gcggaagcag    480
uucgccgaca ucgccuacaa cuaccggcac ggccagccca ucccccgggu ggaguacaug    540
gaggaggaga agaagaccug ggcaccgug uucaagaccc ugaaguccuu guacaagacc     600
cacgccugcu acgaguacaa ccacaucuuc cccugcugg agaaguacug cggcuuccac     660
```

```
gaggacaaca ucccccagcu ggaggacgug ucccaguucc ugcagaccug caccggcuuc    720

cggcugcggc ccguggccgg ccugcugucc ucccgggacu ucuugggcgg ccuggccuuc    780

cggguguucc acugcaccca guacaucagg cacggcucca agcccaugua cacccccgag    840

cccgacaucu gccacgagcu guugggccac gugcccuugu ucuccgaccg gagcuucgcc    900

caguucuccc aggagaucgg ccuggccucc cugggcgccc ccgacgagua caucgagaag    960

cuggccacca ucuacugguu caccguggag uucggccugu gcaagcaggg cgacuccauc   1020

aaggccuacg gcgccggccu gcuguccucc uucggcgagu ugcaguacug cuuguccgag   1080

aagcccaagc ugcugccccu ggagcuggag aagaccgcca uccagaacua caccgugacc   1140

gaguuccagc cccuguacua cguggccgag agcuucaacg acgccaagga gaaggugagg   1200

aacuucgccg ccaccauccc ccggcccuuc uccgugcggu acgaccccua cacccagagg   1260

aucgaggugu uggacaacac ccagcagcug aagaucuugg ccgacuccau caacagcgag   1320

aucggcaucc ugugcagcgc ccugcagaag aucaaguaa                          1359
```

<210> SEQ ID NO 38
<211> LENGTH: 158
<212> TYPE: RNA
<213> ORGANISM: Artificial Sequence
<220> FEATURE:
<223> OTHER INFORMATION: Modified Xenopus beta-globin 3UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 38

```
cnagugacug acuaggaucu gguuaccacu aaaccagccu caagaacacc cgaauggagu     60

cucuaagcua cauaauacca acuuacacuu acaaaauguu gucccccaaa auguagccau    120

ucguaucugc uccuaauaaa aagaaaguuu cuucacnu                            158
```

<210> SEQ ID NO 39
<211> LENGTH: 158
<212> TYPE: RNA
<213> ORGANISM: Artificial Sequence
<220> FEATURE:
<223> OTHER INFORMATION: Modified Xenopus beta-globin 3UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (3)..(3)
<223> OTHER INFORMATION: n is unlocked nucleomonomer UNA-A
<220> FEATURE:
<221> NAME/KEY: misc_feature
<222> LOCATION: (4)..(4)
<223> OTHER INFORMATION: n is unlocked nucleomonomer UNA-G
<220> FEATURE:
<221> NAME/KEY: misc_feature
<222> LOCATION: (155)..(155)
<223> OTHER INFORMATION: n is unlocked nucleomonomer UNA-A
<220> FEATURE:
<221> NAME/KEY: misc_feature
<222> LOCATION: (156)..(156)
<223> OTHER INFORMATION: n is unlocked nucleomonomer UNA-C
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 39
cnnnugacug acuaggaucu gguuaccacu aaaccagccu caagaacacc cgaauggagu 60
cucuaagcua cauaauacca acuuacacuu acaaaauguu gucccccaaa auguagccau 120
ucguaucugc uccuaauaaa aagaaaguuu cuucnnnu 158

<210> SEQ ID NO 40
<211> LENGTH: 158
<212> TYPE: RNA
<213> ORGANISM: Artificial Sequence
<220> FEATURE:
<223> OTHER INFORMATION: Modified Xenopus beta-globin 3UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (8)..(8)
<223> OTHER INFORMATION: n is unlocked nucleomonomer UNA-C
<220> FEATURE:
<221> NAME/KEY: misc_feature
<222> LOCATION: (14)..(14)
<223> OTHER INFORMATION: n is unlocked nucleomonomer UNA-A
<220> FEATURE:
<221> NAME/KEY: misc_feature
<222> LOCATION: (20)..(20)
<223> OTHER INFORMATION: n is unlocked nucleomonomer UNA-U
<220> FEATURE:
<221> NAME/KEY: misc_feature
<222> LOCATION: (26)..(26)
<223> OTHER INFORMATION: n is unlocked nucleomonomer UNA-C
<220> FEATURE:
<221> NAME/KEY: misc_feature
<222> LOCATION: (32)..(32)
<223> OTHER INFORMATION: n is unlocked nucleomonomer UNA-A
<220> FEATURE:
<221> NAME/KEY: misc_feature
<222> LOCATION: (38)..(38)
<223> OTHER INFORMATION: n is unlocked nucleomonomer UNA-C
<220> FEATURE:
<221> NAME/KEY: misc_feature
<222> LOCATION: (44)..(44)
<223> OTHER INFORMATION: n is unlocked nucleomonomer UNA-G
<220> FEATURE:
<221> NAME/KEY: misc_feature
<222> LOCATION: (50)..(50)
<223> OTHER INFORMATION: n is unlocked nucleomonomer UNA-C
<220> FEATURE:
<221> NAME/KEY: misc_feature
<222> LOCATION: (56)..(56)
<223> OTHER INFORMATION: n is unlocked nucleomonomer UNA-G
<220> FEATURE:
<221> NAME/KEY: misc_feature
<222> LOCATION: (62)..(62)
<223> OTHER INFORMATION: n is unlocked nucleomonomer UNA-U
<220> FEATURE:
<221> NAME/KEY: misc_feature
<222> LOCATION: (68)..(68)
<223> OTHER INFORMATION: n is unlocked nucleomonomer UNA-C
<220> FEATURE:
<221> NAME/KEY: misc_feature
<222> LOCATION: (74)..(74)
<223> OTHER INFORMATION: n is unlocked nucleomonomer UNA-A
<220> FEATURE:
<221> NAME/KEY: misc_feature
<222> LOCATION: (80)..(80)
<223> OTHER INFORMATION: n is unlocked nucleomonomer UNA-A
<220> FEATURE:
<221> NAME/KEY: misc_feature
<222> LOCATION: (86)..(86)
<223> OTHER INFORMATION: n is unlocked nucleomonomer UNA-C
<220> FEATURE:
<221> NAME/KEY: misc_feature
<222> LOCATION: (92)..(92)
<223> OTHER INFORMATION: n is unlocked nucleomonomer UNA-C
<220> FEATURE:
<221> NAME/KEY: misc_feature
<222> LOCATION: (98)..(98)
<223> OTHER INFORMATION: n is unlocked nucleomonomer UNA-G
<220> FEATURE:
<221> NAME/KEY: misc_feature
<222> LOCATION: (104)..(104)
<223> OTHER INFORMATION: n is unlocked nucleomonomer UNA-C
<220> FEATURE:
<221> NAME/KEY: misc_feature
<222> LOCATION: (110)..(110)
<223> OTHER INFORMATION: n is unlocked nucleomonomer UNA-A
<220> FEATURE:
<221> NAME/KEY: misc_feature
<222> LOCATION: (116)..(116)
<223> OTHER INFORMATION: n is unlocked nucleomonomer UNA-G
<220> FEATURE:
<221> NAME/KEY: misc_feature
<222> LOCATION: (122)..(122)
<223> OTHER INFORMATION: n is unlocked nucleomonomer UNA-C
<220> FEATURE:
<221> NAME/KEY: misc_feature
<222> LOCATION: (128)..(128)
<223> OTHER INFORMATION: n is unlocked nucleomonomer UNA-U
<220> FEATURE:
<221> NAME/KEY: misc_feature
<222> LOCATION: (134)..(134)
<223> OTHER INFORMATION: n is unlocked nucleomonomer UNA-U
<220> FEATURE:
<221> NAME/KEY: misc_feature
<222> LOCATION: (140)..(140)
<223> OTHER INFORMATION: n is unlocked nucleomonomer UNA-A
<220> FEATURE:
<221> NAME/KEY: misc_feature
<222> LOCATION: (146)..(146)
<223> OTHER INFORMATION: n is unlocked nucleomonomer UNA-A
<220> FEATURE:
<221> NAME/KEY: misc_feature
<222> LOCATION: (152)..(152)
<223> OTHER INFORMATION: n is unlocked nucleomonomer UNA-U
<220> FEATURE:
<221> NAME/KEY: misc_feature
<222> LOCATION: (157)..(157)
<223> OTHER INFORMATION: n is unlocked nucleomonomer UNA-A

<400> SEQUENCE: 40
cnaguganug acunggaucn gguuancacu anaccagncu caanaacacn cgaaungagu 60
cncuaagnua caunauaccn acuuanacuu anaaaaunuu gucncccaan auguanccau 120
unguaucngc uccnaauaan aagaanguuu cnucacnu 158

<210> SEQ ID NO 41
<211> LENGTH: 158
<212> TYPE: RNA
<213> ORGANISM: Artificial Sequence
<220> FEATURE:
<223> OTHER INFORMATION: Modified Xenopus beta-globin 3UTR
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (3)..(3)
<223> OTHER INFORMATION: n is unlocked nucleomonomer UNA-A
<220> FEATURE:
<221> NAME/KEY: misc_feature
<222> LOCATION: (8)..(8)
<223> OTHER INFORMATION: n is unlocked nucleomonomer UNA-C
<220> FEATURE:
<221> NAME/KEY: misc_feature
<222> LOCATION: (9)..(9)
<223> OTHER INFORMATION: n is unlocked nucleomonomer UNA-U -continued
<220> FEATURE:
<221> NAME/KEY: misc_feature
<222> LOCATION: (14)..(14)
<223> OTHER INFORMATION: n is unlocked nucleomonomer UNA-A
<220> FEATURE:
<221> NAME/KEY: misc_feature
<222> LOCATION: (15)..(15)
<223> OTHER INFORMATION: n is unlocked nucleomonomer UNA-G
<220> FEATURE:
<221> NAME/KEY: misc_feature
<222> LOCATION: (20)..(20)
<223> OTHER INFORMATION: n is unlocked nucleomonomer UNA-U
<220> FEATURE:
<221> NAME/KEY: misc_feature
<222> LOCATION: (21)..(21)
<223> OTHER INFORMATION: n is unlocked nucleomonomer UNA-G
<220> FEATURE:
<221> NAME/KEY: misc_feature
<222> LOCATION: (26)..(27)
<223> OTHER INFORMATION: n is unlocked nucleomonomer UNA-C
<220> FEATURE:
<221> NAME/KEY: misc_feature
<222> LOCATION: (32)..(33)
<223> OTHER INFORMATION: n is unlocked nucleomonomer UNA-A
<220> FEATURE:
<221> NAME/KEY: misc_feature
<222> LOCATION: (38)..(39)
<223> OTHER INFORMATION: n is unlocked nucleomonomer UNA-C
<220> FEATURE:
<221> NAME/KEY: misc_feature
<222> LOCATION: (44)..(44)
<223> OTHER INFORMATION: n is unlocked nucleomonomer UNA-G
<220> FEATURE:
<221> NAME/KEY: misc_feature
<222> LOCATION: (45)..(45)
<223> OTHER INFORMATION: n is unlocked nucleomonomer UNA-A
<220> FEATURE:
<221> NAME/KEY: misc_feature
<222> LOCATION: (50)..(51)
<223> OTHER INFORMATION: n is unlocked nucleomonomer UNA-C
<220> FEATURE:
<221> NAME/KEY: misc_feature
<222> LOCATION: (56)..(57)
<223> OTHER INFORMATION: n is unlocked nucleomonomer UNA-G
<220> FEATURE:
<221> NAME/KEY: misc_feature
<222> LOCATION: (62)..(62)
<223> OTHER INFORMATION: n is unlocked nucleomonomer UNA-U
<220> FEATURE:
<221> NAME/KEY: misc_feature
<222> LOCATION: (63)..(63)
<223> OTHER INFORMATION: n is unlocked nucleomonomer UNA-C
<220> FEATURE:
<221> NAME/KEY: misc_feature
<222> LOCATION: (68)..(68)
<223> OTHER INFORMATION: n is unlocked nucleomonomer UNA-C
<220> FEATURE:
<221> NAME/KEY: misc_feature
<222> LOCATION: (69)..(69)
<223> OTHER INFORMATION: n is unlocked nucleomonomer UNA-U
<220> FEATURE:
<221> NAME/KEY: misc_feature
<222> LOCATION: (74)..(75)
<223> OTHER INFORMATION: n is unlocked nucleomonomer UNA-A
<220> FEATURE:
<221> NAME/KEY: misc_feature
<222> LOCATION: (80)..(81)
<223> OTHER INFORMATION: n is unlocked nucleomonomer UNA-A
<220> FEATURE:
<221> NAME/KEY: misc_feature
<222> LOCATION: (86)..(86)
<223> OTHER INFORMATION: n is unlocked nucleomonomer UNA-C
<220> FEATURE:
<221> NAME/KEY: misc_feature
<222> LOCATION: (87)..(87)
<223> OTHER INFORMATION: n is unlocked nucleomonomer UNA-A -continued
<220> FEATURE:
<221> NAME/KEY: misc_feature
<222> LOCATION: (92)..(92)
<223> OTHER INFORMATION: n is unlocked nucleomonomer UNA-C
<220> FEATURE:
<221> NAME/KEY: misc_feature
<222> LOCATION: (93)..(93)
<223> OTHER INFORMATION: n is unlocked nucleomonomer UNA-A
<220> FEATURE:
<221> NAME/KEY: misc_feature
<222> LOCATION: (98)..(98)
<223> OTHER INFORMATION: n is unlocked nucleomonomer UNA-G
<220> FEATURE:
<221> NAME/KEY: misc_feature
<222> LOCATION: (99)..(99)
<223> OTHER INFORMATION: n is unlocked nucleomonomer UNA-U
<220> FEATURE:
<221> NAME/KEY: misc_feature
<222> LOCATION: (104)..(105)
<223> OTHER INFORMATION: n is unlocked nucleomonomer UNA-C
<220> FEATURE:
<221> NAME/KEY: misc_feature
<222> LOCATION: (110)..(111)
<223> OTHER INFORMATION: n is unlocked nucleomonomer UNA-A
<220> FEATURE:
<221> NAME/KEY: misc_feature
<222> LOCATION: (116)..(116)
<223> OTHER INFORMATION: n is unlocked nucleomonomer UNA-G
<220> FEATURE:
<221> NAME/KEY: misc_feature
<222> LOCATION: (117)..(117)
<223> OTHER INFORMATION: n is unlocked nucleomonomer UNA-C
<220> FEATURE:
<221> NAME/KEY: misc_feature
<222> LOCATION: (122)..(122)
<223> OTHER INFORMATION: n is unlocked nucleomonomer UNA-C
<220> FEATURE:
<221> NAME/KEY: misc_feature
<222> LOCATION: (123)..(123)
<223> OTHER INFORMATION: n is unlocked nucleomonomer UNA-G
<220> FEATURE:
<221> NAME/KEY: misc_feature
<222> LOCATION: (128)..(128)
<223> OTHER INFORMATION: n is unlocked nucleomonomer UNA-U
<220> FEATURE:
<221> NAME/KEY: misc_feature
<222> LOCATION: (129)..(129)
<223> OTHER INFORMATION: n is unlocked nucleomonomer UNA-G
<220> FEATURE:
<221> NAME/KEY: misc_feature
<222> LOCATION: (134)..(134)
<223> OTHER INFORMATION: n is unlocked nucleomonomer UNA-U
<220> FEATURE:
<221> NAME/KEY: misc_feature
<222> LOCATION: (135)..(135)
<223> OTHER INFORMATION: n is unlocked nucleomonomer UNA-A
<220> FEATURE:
<221> NAME/KEY: misc_feature
<222> LOCATION: (140)..(141)
<223> OTHER INFORMATION: n is unlocked nucleomonomer UNA-A
<220> FEATURE:
<221> NAME/KEY: misc_feature
<222> LOCATION: (146)..(146)
<223> OTHER INFORMATION: n is unlocked nucleomonomer UNA-A
<220> FEATURE:
<221> NAME/KEY: misc_feature
<222> LOCATION: (147)..(147)
<223> OTHER INFORMATION: n is unlocked nucleomonomer UNA-G
<220> FEATURE:
<221> NAME/KEY: misc_feature
<222> LOCATION: (152)..(153)
<223> OTHER INFORMATION: n is unlocked nucleomonomer UNA-U
<220> FEATURE:
<221> NAME/KEY: misc_feature
<222> LOCATION: (157)..(157)
<223> OTHER INFORMATION: n is unlocked nucleomonomer UNA-A -continued

<400> SEQUENCE: 41
cnnguganng acunngaucn nguuannacu annccagnnu caannacacn ngaaunnagu 60
cnnuaagnna caunnuaccn ncuuanncuu annaaaunnu gucnnccaan nuguanncau 120
unnuaucnnc uccnnauaan nagaannuuu cnncacnu 158

<210> SEQ ID NO 42
<211> LENGTH: 158
<212> TYPE: RNA
<213> ORGANISM: Artificial Sequence
<220> FEATURE:
<223> OTHER INFORMATION: Modified Xenopus beta-globin 3UTR
<220> FEATURE:
<221> NAME/KEY: misc_feature
<222> LOCATION: (0)..(0)
<223> OTHER INFORMATION: n is unlocked nucleomonomer UNA-G
<220> FEATURE:
<221> NAME/KEY: misc_feature
<222> LOCATION: (1)..(1)
<223> OTHER INFORMATION: n is unlocked nucleomonomer UNA-C
<220> FEATURE:
<221> NAME/KEY: misc_feature
<222> LOCATION: (2)..(2)
<223> OTHER INFORMATION: n is unlocked nucleomonomer UNA-U
<220> FEATURE:
<221> NAME/KEY: misc_feature
<222> LOCATION: (3)..(3)
<223> OTHER INFORMATION: n is unlocked nucleomonomer UNA-A
<220> FEATURE:
<221> NAME/KEY: misc_feature
<222> LOCATION: (4)..(4)
<223> OTHER INFORMATION: n is unlocked nucleomonomer UNA-G
<220> FEATURE:
<221> NAME/KEY: misc_feature
<222> LOCATION: (5)..(5)
<223> OTHER INFORMATION: n is unlocked nucleomonomer UNA-U
<220> FEATURE:
<221> NAME/KEY: misc_feature
<222> LOCATION: (6)..(6)
<223> OTHER INFORMATION: n is unlocked nucleomonomer UNA-G
<220> FEATURE:
<221> NAME/KEY: misc_feature
<222> LOCATION: (7)..(7)
<223> OTHER INFORMATION: n is unlocked nucleomonomer UNA-A
<220> FEATURE:
<221> NAME/KEY: misc_feature
<222> LOCATION: (8)..(8)
<223> OTHER INFORMATION: n is unlocked nucleomonomer UNA-C
<220> FEATURE:
<221> NAME/KEY: misc_feature
<222> LOCATION: (9)..(9)
<223> OTHER INFORMATION: n is unlocked nucleomonomer UNA-U
<220> FEATURE:
<221> NAME/KEY: misc_feature
<222> LOCATION: (10)..(10)
<223> OTHER INFORMATION: n is unlocked nucleomonomer UNA-G
<220> FEATURE:
<221> NAME/KEY: misc_feature
<222> LOCATION: (11)..(11)
<223> OTHER INFORMATION: n is unlocked nucleomonomer UNA-A
<220> FEATURE:
<221> NAME/KEY: misc_feature
<222> LOCATION: (12)..(12)
<223> OTHER INFORMATION: n is unlocked nucleomonomer UNA-C
<220> FEATURE:
<221> NAME/KEY: misc_feature
<222> LOCATION: (13)..(13)
<223> OTHER INFORMATION: n is unlocked nucleomonomer UNA-U
<220> FEATURE:
<221> NAME/KEY: misc_feature
<222> LOCATION: (14)..(14)
<223> OTHER INFORMATION: n is unlocked nucleomonomer UNA-A
<220> FEATURE:
<221> NAME/KEY: misc_feature
<222> LOCATION: (15)..(16)
<223> OTHER INFORMATION: n is unlocked nucleomonomer UNA-G
<220> FEATURE:
<221> NAME/KEY: misc_feature
<222> LOCATION: (17)..(17)
<223> OTHER INFORMATION: n is unlocked nucleomonomer UNA-A
<220> FEATURE:
<221> NAME/KEY: misc_feature
<222> LOCATION: (18)..(18)
<223> OTHER INFORMATION: n is unlocked nucleomonomer UNA-U
<220> FEATURE:
<221> NAME/KEY: misc_feature
<222> LOCATION: (19)..(19)
<223> OTHER INFORMATION: n is unlocked nucleomonomer UNA-C
<220> FEATURE:
<221> NAME/KEY: misc_feature
<222> LOCATION: (20)..(20)
<223> OTHER INFORMATION: n is unlocked nucleomonomer UNA-U
<220> FEATURE:
<221> NAME/KEY: misc_feature
<222> LOCATION: (21)..(22)
<223> OTHER INFORMATION: n is unlocked nucleomonomer UNA-G
<220> FEATURE:
<221> NAME/KEY: misc_feature
<222> LOCATION: (23)..(24)
<223> OTHER INFORMATION: n is unlocked nucleomonomer UNA-U
<220> FEATURE:
<221> NAME/KEY: misc_feature
<222> LOCATION: (25)..(25)
<223> OTHER INFORMATION: n is unlocked nucleomonomer UNA-A
<220> FEATURE:
<221> NAME/KEY: misc_feature
<222> LOCATION: (26)..(27)
<223> OTHER INFORMATION: n is unlocked nucleomonomer UNA-C
<220> FEATURE:
<221> NAME/KEY: misc_feature
<222> LOCATION: (28)..(28)
<223> OTHER INFORMATION: n is unlocked nucleomonomer UNA-A
<220> FEATURE:
<221> NAME/KEY: misc_feature
<222> LOCATION: (29)..(29)
<223> OTHER INFORMATION: n is unlocked nucleomonomer UNA-C
<220> FEATURE:
<221> NAME/KEY: misc_feature
<222> LOCATION: (30)..(30)
<223> OTHER INFORMATION: n is unlocked nucleomonomer UNA-U
<220> FEATURE:
<221> NAME/KEY: misc_feature
<222> LOCATION: (31)..(33)
<223> OTHER INFORMATION: n is unlocked nucleomonomer UNA-A
<220> FEATURE:
<221> NAME/KEY: misc_feature
<222> LOCATION: (34)..(35)
<223> OTHER INFORMATION: n is unlocked nucleomonomer UNA-C
<220> FEATURE:
<221> NAME/KEY: misc_feature
<222> LOCATION: (36)..(36)
<223> OTHER INFORMATION: n is unlocked nucleomonomer UNA-A
<220> FEATURE:
<221> NAME/KEY: misc_feature
<222> LOCATION: (37)..(37)
<223> OTHER INFORMATION: n is unlocked nucleomonomer UNA-G
<220> FEATURE:
<221> NAME/KEY: misc_feature
<222> LOCATION: (38)..(39)
<223> OTHER INFORMATION: n is unlocked nucleomonomer UNA-C
<220> FEATURE:
<221> NAME/KEY: misc_feature
<222> LOCATION: (40)..(40)
<223> OTHER INFORMATION: n is unlocked nucleomonomer UNA-U
<220> FEATURE:
<221> NAME/KEY: misc_feature
<222> LOCATION: (41)..(41)
<223> OTHER INFORMATION: n is unlocked nucleomonomer UNA-C
<220> FEATURE:
<221> NAME/KEY: misc_feature
<222> LOCATION: (42)..(43)
<223> OTHER INFORMATION: n is unlocked nucleomonomer UNA-A -continued
<220> FEATURE:
<221> NAME/KEY: misc_feature
<222> LOCATION: (44)..(44)
<223> OTHER INFORMATION: n is unlocked nucleomonomer UNA-G
<220> FEATURE:
<221> NAME/KEY: misc_feature
<222> LOCATION: (45)..(46)
<223> OTHER INFORMATION: n is unlocked nucleomonomer UNA-A
<220> FEATURE:
<221> NAME/KEY: misc_feature
<222> LOCATION: (47)..(47)
<223> OTHER INFORMATION: n is unlocked nucleomonomer UNA-C
<220> FEATURE:
<221> NAME/KEY: misc_feature
<222> LOCATION: (48)..(48)
<223> OTHER INFORMATION: n is unlocked nucleomonomer UNA-A
<220> FEATURE:
<221> NAME/KEY: misc_feature
<222> LOCATION: (49)..(51)
<223> OTHER INFORMATION: n is unlocked nucleomonomer UNA-C
<220> FEATURE:
<221> NAME/KEY: misc_feature
<222> LOCATION: (52)..(52)
<223> OTHER INFORMATION: n is unlocked nucleomonomer UNA-G
<220> FEATURE:
<221> NAME/KEY: misc_feature
<222> LOCATION: (53)..(54)
<223> OTHER INFORMATION: n is unlocked nucleomonomer UNA-A
<220> FEATURE:
<221> NAME/KEY: misc_feature
<222> LOCATION: (55)..(55)
<223> OTHER INFORMATION: n is unlocked nucleomonomer UNA-U
<220> FEATURE:
<221> NAME/KEY: misc_feature
<222> LOCATION: (56)..(57)
<223> OTHER INFORMATION: n is unlocked nucleomonomer UNA-G
<220> FEATURE:
<221> NAME/KEY: misc_feature
<222> LOCATION: (58)..(58)
<223> OTHER INFORMATION: n is unlocked nucleomonomer UNA-A
<220> FEATURE:
<221> NAME/KEY: misc_feature
<222> LOCATION: (59)..(59)
<223> OTHER INFORMATION: n is unlocked nucleomonomer UNA-G
<220> FEATURE:
<221> NAME/KEY: misc_feature
<222> LOCATION: (60)..(60)
<223> OTHER INFORMATION: n is unlocked nucleomonomer UNA-U
<220> FEATURE:
<221> NAME/KEY: misc_feature
<222> LOCATION: (61)..(61)
<223> OTHER INFORMATION: n is unlocked nucleomonomer UNA-C
<220> FEATURE:
<221> NAME/KEY: misc_feature
<222> LOCATION: (62)..(62)
<223> OTHER INFORMATION: n is unlocked nucleomonomer UNA-U
<220> FEATURE:
<221> NAME/KEY: misc_feature
<222> LOCATION: (63)..(63)
<223> OTHER INFORMATION: n is unlocked nucleomonomer UNA-C
<220> FEATURE:
<221> NAME/KEY: misc_feature
<222> LOCATION: (64)..(64)
<223> OTHER INFORMATION: n is unlocked nucleomonomer UNA-U
<220> FEATURE:
<221> NAME/KEY: misc_feature
<222> LOCATION: (65)..(66)
<223> OTHER INFORMATION: n is unlocked nucleomonomer UNA-A
<220> FEATURE:
<221> NAME/KEY: misc_feature
<222> LOCATION: (67)..(67)
<223> OTHER INFORMATION: n is unlocked nucleomonomer UNA-G
<220> FEATURE:
<221> NAME/KEY: misc_feature
<222> LOCATION: (68)..(68)
<223> OTHER INFORMATION: n is unlocked nucleomonomer UNA-C
<220> FEATURE:
<221> NAME/KEY: misc_feature
<222> LOCATION: (69)..(69)
<223> OTHER INFORMATION: n is unlocked nucleomonomer UNA-U
<220> FEATURE:
<221> NAME/KEY: misc_feature
<222> LOCATION: (70)..(70)
<223> OTHER INFORMATION: n is unlocked nucleomonomer UNA-A
<220> FEATURE:
<221> NAME/KEY: misc_feature
<222> LOCATION: (71)..(71)
<223> OTHER INFORMATION: n is unlocked nucleomonomer UNA-C
<220> FEATURE:
<221> NAME/KEY: misc_feature
<222> LOCATION: (72)..(72)
<223> OTHER INFORMATION: n is unlocked nucleomonomer UNA-A
<220> FEATURE:
<221> NAME/KEY: misc_feature
<222> LOCATION: (73)..(73)
<223> OTHER INFORMATION: n is unlocked nucleomonomer UNA-U
<220> FEATURE:
<221> NAME/KEY: misc_feature
<222> LOCATION: (74)..(75)
<223> OTHER INFORMATION: n is unlocked nucleomonomer UNA-A
<220> FEATURE:
<221> NAME/KEY: misc_feature
<222> LOCATION: (76)..(76)
<223> OTHER INFORMATION: n is unlocked nucleomonomer UNA-U
<220> FEATURE:
<221> NAME/KEY: misc_feature
<222> LOCATION: (77)..(77)
<223> OTHER INFORMATION: n is unlocked nucleomonomer UNA-A
<220> FEATURE:
<221> NAME/KEY: misc_feature
<222> LOCATION: (78)..(79)
<223> OTHER INFORMATION: n is unlocked nucleomonomer UNA-C
<220> FEATURE:
<221> NAME/KEY: misc_feature
<222> LOCATION: (80)..(81)
<223> OTHER INFORMATION: n is unlocked nucleomonomer UNA-A
<220> FEATURE:
<221> NAME/KEY: misc_feature
<222> LOCATION: (82)..(82)
<223> OTHER INFORMATION: n is unlocked nucleomonomer UNA-C
<220> FEATURE:
<221> NAME/KEY: misc_feature
<222> LOCATION: (83)..(84)
<223> OTHER INFORMATION: n is unlocked nucleomonomer UNA-U
<220> FEATURE:
<221> NAME/KEY: misc_feature
<222> LOCATION: (85)..(85)
<223> OTHER INFORMATION: n is unlocked nucleomonomer UNA-A
<220> FEATURE:
<221> NAME/KEY: misc_feature
<222> LOCATION: (86)..(86)
<223> OTHER INFORMATION: n is unlocked nucleomonomer UNA-C
<220> FEATURE:
<221> NAME/KEY: misc_feature
<222> LOCATION: (87)..(87)
<223> OTHER INFORMATION: n is unlocked nucleomonomer UNA-A
<220> FEATURE:
<221> NAME/KEY: misc_feature
<222> LOCATION: (88)..(88)
<223> OTHER INFORMATION: n is unlocked nucleomonomer UNA-C
<220> FEATURE:
<221> NAME/KEY: misc_feature
<222> LOCATION: (89)..(90)
<223> OTHER INFORMATION: n is unlocked nucleomonomer UNA-U
<220> FEATURE:
<221> NAME/KEY: misc_feature
<222> LOCATION: (91)..(91)
<223> OTHER INFORMATION: n is unlocked nucleomonomer UNA-A
<220> FEATURE:
<221> NAME/KEY: misc_feature
<222> LOCATION: (92)..(92)
<223> OTHER INFORMATION: n is unlocked nucleomonomer UNA-C -continued
<220> FEATURE:
<221> NAME/KEY: misc_feature
<222> LOCATION: (93)..(96)
<223> OTHER INFORMATION: n is unlocked nucleomonomer UNA-A
<220> FEATURE:
<221> NAME/KEY: misc_feature
<222> LOCATION: (97)..(97)
<223> OTHER INFORMATION: n is unlocked nucleomonomer UNA-U
<220> FEATURE:
<221> NAME/KEY: misc_feature
<222> LOCATION: (98)..(98)
<223> OTHER INFORMATION: n is unlocked nucleomonomer UNA-G
<220> FEATURE:
<221> NAME/KEY: misc_feature
<222> LOCATION: (99)..(100)
<223> OTHER INFORMATION: n is unlocked nucleomonomer UNA-U
<220> FEATURE:
<221> NAME/KEY: misc_feature
<222> LOCATION: (101)..(101)
<223> OTHER INFORMATION: n is unlocked nucleomonomer UNA-G
<220> FEATURE:
<221> NAME/KEY: misc_feature
<222> LOCATION: (102)..(102)
<223> OTHER INFORMATION: n is unlocked nucleomonomer UNA-U
<220> FEATURE:
<221> NAME/KEY: misc_feature
<222> LOCATION: (103)..(107)
<223> OTHER INFORMATION: n is unlocked nucleomonomer UNA-C
<220> FEATURE:
<221> NAME/KEY: misc_feature
<222> LOCATION: (108)..(111)
<223> OTHER INFORMATION: n is unlocked nucleomonomer UNA-A
<220> FEATURE:
<221> NAME/KEY: misc_feature
<222> LOCATION: (112)..(112)
<223> OTHER INFORMATION: n is unlocked nucleomonomer UNA-U
<220> FEATURE:
<221> NAME/KEY: misc_feature
<222> LOCATION: (113)..(113)
<223> OTHER INFORMATION: n is unlocked nucleomonomer UNA-G
<220> FEATURE:
<221> NAME/KEY: misc_feature
<222> LOCATION: (114)..(114)
<223> OTHER INFORMATION: n is unlocked nucleomonomer UNA-U
<220> FEATURE:
<221> NAME/KEY: misc_feature
<222> LOCATION: (115)..(115)
<223> OTHER INFORMATION: n is unlocked nucleomonomer UNA-A
<220> FEATURE:
<221> NAME/KEY: misc_feature
<222> LOCATION: (116)..(116)
<223> OTHER INFORMATION: n is unlocked nucleomonomer UNA-G
<220> FEATURE:
<221> NAME/KEY: misc_feature
<222> LOCATION: (117)..(118)
<223> OTHER INFORMATION: n is unlocked nucleomonomer UNA-C
<220> FEATURE:
<221> NAME/KEY: misc_feature
<222> LOCATION: (119)..(119)
<223> OTHER INFORMATION: n is unlocked nucleomonomer UNA-A
<220> FEATURE:
<221> NAME/KEY: misc_feature
<222> LOCATION: (120)..(121)
<223> OTHER INFORMATION: n is unlocked nucleomonomer UNA-U
<220> FEATURE:
<221> NAME/KEY: misc_feature
<222> LOCATION: (122)..(122)
<223> OTHER INFORMATION: n is unlocked nucleomonomer UNA-C
<220> FEATURE:
<221> NAME/KEY: misc_feature
<222> LOCATION: (123)..(123)
<223> OTHER INFORMATION: n is unlocked nucleomonomer UNA-G
<220> FEATURE:
<221> NAME/KEY: misc_feature
<222> LOCATION: (124)..(124)
<223> OTHER INFORMATION: n is unlocked nucleomonomer UNA-U
<220> FEATURE:
<221> NAME/KEY: misc_feature
<222> LOCATION: (125)..(125)
<223> OTHER INFORMATION: n is unlocked nucleomonomer UNA-A
<220> FEATURE:
<221> NAME/KEY: misc_feature
<222> LOCATION: (126)..(126)
<223> OTHER INFORMATION: n is unlocked nucleomonomer UNA-U
<220> FEATURE:
<221> NAME/KEY: misc_feature
<222> LOCATION: (127)..(127)
<223> OTHER INFORMATION: n is unlocked nucleomonomer UNA-C
<220> FEATURE:
<221> NAME/KEY: misc_feature
<222> LOCATION: (128)..(128)
<223> OTHER INFORMATION: n is unlocked nucleomonomer UNA-U
<220> FEATURE:
<221> NAME/KEY: misc_feature
<222> LOCATION: (129)..(129)
<223> OTHER INFORMATION: n is unlocked nucleomonomer UNA-G
<220> FEATURE:
<221> NAME/KEY: misc_feature
<222> LOCATION: (130)..(130)
<223> OTHER INFORMATION: n is unlocked nucleomonomer UNA-C
<220> FEATURE:
<221> NAME/KEY: misc_feature
<222> LOCATION: (131)..(131)
<223> OTHER INFORMATION: n is unlocked nucleomonomer UNA-U
<220> FEATURE:
<221> NAME/KEY: misc_feature
<222> LOCATION: (132)..(133)
<223> OTHER INFORMATION: n is unlocked nucleomonomer UNA-C
<220> FEATURE:
<221> NAME/KEY: misc_feature
<222> LOCATION: (134)..(134)
<223> OTHER INFORMATION: n is unlocked nucleomonomer UNA-U
<220> FEATURE:
<221> NAME/KEY: misc_feature
<222> LOCATION: (135)..(136)
<223> OTHER INFORMATION: n is unlocked nucleomonomer UNA-A
<220> FEATURE:
<221> NAME/KEY: misc_feature
<222> LOCATION: (137)..(137)
<223> OTHER INFORMATION: n is unlocked nucleomonomer UNA-U
<220> FEATURE:
<221> NAME/KEY: misc_feature
<222> LOCATION: (138)..(142)
<223> OTHER INFORMATION: n is unlocked nucleomonomer UNA-A
<220> FEATURE:
<221> NAME/KEY: misc_feature
<222> LOCATION: (143)..(143)
<223> OTHER INFORMATION: n is unlocked nucleomonomer UNA-G
<220> FEATURE:
<221> NAME/KEY: misc_feature
<222> LOCATION: (144)..(146)
<223> OTHER INFORMATION: n is unlocked nucleomonomer UNA-A
<220> FEATURE:
<221> NAME/KEY: misc_feature
<222> LOCATION: (147)..(147)
<223> OTHER INFORMATION: n is unlocked nucleomonomer UNA-G
<220> FEATURE:
<221> NAME/KEY: misc_feature
<222> LOCATION: (148)..(149)
<223> OTHER INFORMATION: n is unlocked nucleomonomer UNA-U
<220> FEATURE:
<221> NAME/KEY: misc_feature
<222> LOCATION: (150)..(150)
<223> OTHER INFORMATION: n is unlocked nucleomonomer UNA-U
<220> FEATURE:
<221> NAME/KEY: misc_feature
<222> LOCATION: (151)..(151)
<223> OTHER INFORMATION: n is unlocked nucleomonomer UNA-C
<220> FEATURE:
<221> NAME/KEY: misc_feature
<222> LOCATION: (152)..(153)
<223> OTHER INFORMATION: n is unlocked nucleomonomer UNA-U
<220> FEATURE:
<221> NAME/KEY: misc_feature
<222> LOCATION: (154)..(154)
<223> OTHER INFORMATION: n is unlocked nucleomonomer UNA-C
<220> FEATURE:
<221> NAME/KEY: misc_feature
<222> LOCATION: (155)..(155)
<223> OTHER INFORMATION: n is unlocked nucleomonomer UNA-A
<220> FEATURE:
<221> NAME/KEY: misc_feature
<222> LOCATION: (156)..(156)
<223> OTHER INFORMATION: n is unlocked nucleomonomer UNA-C
<220> FEATURE:
<221> NAME/KEY: misc_feature
<222> LOCATION: (157)..(157)
<223> OTHER INFORMATION: n is unlocked nucleomonomer UNA-A
<220> FEATURE:
<221> NAME/KEY: misc_feature
<222> LOCATION: (158)..(158)
<223> OTHER INFORMATION: n is unlocked nucleomonomer UNA-U

<400> SEQUENCE: 42
nnnnnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnn 158

<210> SEQ ID NO 43
<211> LENGTH: 114
<212> TYPE: RNA
<213> ORGANISM: Unknown
<220> FEATURE:
<223> OTHER INFORMATION: Poly(A) 114 Tail

<400> SEQUENCE: 43
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaa 114

<210> SEQ ID NO 44
<211> LENGTH: 9
<212> TYPE: RNA
<213> ORGANISM: Unknown
<220> FEATURE:
<223> OTHER INFORMATION: Triple Stop Codon

<400> SEQUENCE: 44 auaagugaa 9

<210> SEQ ID NO 45
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 45
augagcaccg ccgugcugga gaaccccggc cugggccgga agcugagcga cuucggccag 60
gagaccagcu acaucgagga caacugcaac cagaacggcg ccaucagccu gaucuucagc 120
cugaaggagg aggugggcgc ccuggccaag gugcugcggc uguucgagga gaacgacgug 180
aaccugaccc acaucgagag ccggcccagc cggcugaaga aggacgagua cgaguucuuc 240
acccaccugg acaagcggag ccugcccgcc cugaccaaca ucaucaagau ccugcggcac 300
gacaucggcg ccaccgugca cgagcugagc cgggacaaga agaaggacac cgugcccugg 360
uucccccgga ccauccagga gcuggaccgg uucgccaacc agauccugag cuacggcgcc 420

-continued

```
gagcuggacg ccgaccaccc cggcuucaag gaccccgugu accgggcccg gcggaagcag    480

uucgccgaca ucgccuacaa cuaccggcac ggccagccca ucccccgggu ggaguacaug    540

gaggaggaga agaagaccug ggcaccgug uucaagaccc ugaagagccu guacaagacc    600

cacgccugcu acgaguacaa ccacaucuuc cccugcugg agaaguacug cggcuuccac    660

gaggacaaca ucccccagcu ggaggacgug agccaguucc ugcagaccug caccggcuuc    720

cggcugcggc ccguggccgg ccugcugagc agccgggacu uccugggcgg ccuggccuuc    780

cggguguucc acugcaccca guacauccgg cacggcagca agcccaugua cacccccgag    840

cccgacaucu gccacgagcu gcugggccac gugccccugu ucagcgaccg gagcuucgcc    900

caguucagcc aggagaucgg ccuggccagc cugggcgccc ccgacgagua caucgagaag    960

cuggccacca ucuacugguu caccguggag uucggccugu gcaagcaggg cgacagcauc   1020

aaggccuacg gcgccggccu gcugagcagc uucggcgagc ugcaguacug ccugagcgag   1080

aagcccaagc ugcugccccu ggagcuggag aagaccgcca uccagaacua caccgugacc   1140

gaguuccagc cccuguacua cguggccgag agcuucaacg acgccaagga gaaggugcgg   1200

aacuucgccg ccaccauccc ccggcccuuc agcgugcggu acgaccccua cacccagcgg   1260

aucgaggugc uggacaacac ccagcagcug aagauccugg ccgacagcau caacagcgag   1320

aucggcaucc ugugcagcgc ccugcagaag aucaaguaa                          1359


<210> SEQ ID NO 46
<211> LENGTH: 1359
<212> TYPE: RNA
<213> ORGANISM: Artificial Sequence
<220> FEATURE:
<223> OTHER INFORMATION: Codon-Optimized PAH Coding Sequence

<400> SEQUENCE: 46

auguccaccg ccguccugga gaaccccggc cucggcagaa aacucucuga cuucggccag     60

gagacaagcu auaucgagga caacugcaau cagaaugggg ccauuucccu gauuuuuucc    120

cucaaagagg aggugggggc ucucgccaaa guccuccggc ucuucgaaga aaaugauguc    180

aaccugaccc auaucgaguc uaggccuucu cgccucaaga aagaugaaua ugaguucuuu    240

acccaccucg auaaacgcag ccugccugcu cugacaaaca uuauuaagau ucucagacac    300

gacaucgggg ccaccgucca cgaacugucc cgggauaaga agaaagacac agugcccugg    360

uuucccagga ccauccagga acuggacagg uucgccaauc agauccucag cuauggcgcc    420

gagcuggaug cugaccaucc ugggguucaaa gauccugugu accgcgcuag gcgcaagcag    480

uucgcugaca ucgccuacaa cuaccggcac gggcagccca uuccucgggu ggaguacaug    540

gaagaggaga agaaaacaug ggcacagug uuuaagaccc ugaagucccu cuauaaaacc    600

cacgcuugcu augaauacaa ucauaucuuc cccugcugg agaaguacug cggcuuucac    660

gaggauaaca ucccccagcu ggaggacgug ucucaguuuc ugcagaccug caccggguuu    720

cggcuccggc cuguggcugg ccugcugucc ucucgcgauu uucucggggg ccuggccuuu    780

cgggucuuuc auugcacaca guacauuagg cacggcucca agcccaugua uacccccgag    840

ccugacauuu gccacgaacu gcucggccac gugccccucu ucuccgaucg gagcuucgcc    900

caguucuccc aggagaucgg ccuggccucu cugggggcuc cugaugagua caucgagaag    960

cucgccacaa ucuacugguu caccguggaa uucgggcucu gcaaacaggg cgacuccauu   1020

aaggcuuaug ggcugggcu ccuguccucc uucggggagc uccaguacug ccucuccgaa   1080

aagcccaagc ugcucccccu ggaacuggaa aagacagcca uucagaauua caccgucaca   1140
```

-continued

| | |
|---|---|
| gaauuucagc cccucuauua cguggcugaa aguuucaaug augccaagga aaaagucaga | 1200 |
| aacuucgcug ccacaauucc ucgccccuuu uccgugcggu acgaccccua cacccagaga | 1260 |
| aucgaagucc ucgacaauac ccagcagcug aagauccucg cugauuccau caacagugag | 1320 |
| aucggcauuc ugugcagugc ccuccagaaa auuaaguag | 1359 |